US010036075B2

(12) United States Patent
McLean et al.

(10) Patent No.: US 10,036,075 B2
(45) Date of Patent: Jul. 31, 2018

(54) RISK STRATIFICATION IN INFLUENZA

(71) Applicant: Nepean Blue Mountains Local Health District, Kingswood, NSW (AU)

(72) Inventors: Anthony McLean, Faulconbridge (AU); Benjamin Tang, Glebe (AU); Grant Peter Parnell, Summer Hill (AU); Maryam Shojaei, Westmead (AU)

(73) Assignee: Nepean Blue Mountains Local Health District, Kingswood, NSW (AU)

( * ) Notice: Subject to any disclaimer, the term of this patent is extended or adjusted under 35 U.S.C. 154(b) by 0 days.

(21) Appl. No.: 14/410,367

(22) PCT Filed: Jul. 10, 2013

(86) PCT No.: PCT/AU2013/000765
§ 371 (c)(1),
(2) Date: Dec. 22, 2014

(87) PCT Pub. No.: WO2014/008545
PCT Pub. Date: Jan. 16, 2014

(65) Prior Publication Data
US 2015/0322538 A1 Nov. 12, 2015

(30) Foreign Application Priority Data

Jul. 10, 2012 (AU) ................................ 2012902954

(51) Int. Cl.
G01N 33/68 (2006.01)
C12Q 1/68 (2018.01)
G01N 33/569 (2006.01)
C12Q 1/70 (2006.01)
C12Q 1/6883 (2018.01)

(52) U.S. Cl.
CPC ........... *C12Q 1/701* (2013.01); *C12Q 1/6883* (2013.01); *G01N 33/56983* (2013.01); *G01N 33/6866* (2013.01); *C12Q 2600/112* (2013.01); *C12Q 2600/158* (2013.01); *G01N 2333/11* (2013.01); *G01N 2333/46* (2013.01); *G01N 2333/52* (2013.01); *G01N 2469/00* (2013.01); *G01N 2800/50* (2013.01)

(58) Field of Classification Search
None
See application file for complete search history.

(56) References Cited

U.S. PATENT DOCUMENTS

| 5,792,626 A * | 8/1998 | Hillman | C07K 14/4718 |
| | | | 435/320.1 |
| 6,821,724 B1 * | 11/2004 | Mittman | C07H 21/02 |
| | | | 422/68.1 |
| 2005/0208496 A1 | 9/2005 | Ohtani et al. | |
| 2005/0244851 A1 | 11/2005 | Blume et al. | |
| 2006/0292572 A1 * | 12/2006 | Stuart | C12Q 1/6881 |
| | | | 435/6.14 |
| 2008/0171323 A1 * | 7/2008 | Banchereau | C12Q 1/6883 |
| | | | 435/6.16 |
| 2012/0009148 A1 * | 1/2012 | Smith | C12Q 1/6883 |
| | | | 424/85.4 |
| 2012/0114661 A1 | 5/2012 | Ginsburg et al. | |
| 2012/0214705 A1 * | 8/2012 | Bevins | C12Q 1/6883 |
| | | | 506/9 |

FOREIGN PATENT DOCUMENTS

| EP | 1394274 | 3/2004 | |
| WO | 2011/005793 | 1/2011 | |
| WO | WO 2011008349 A2 * | 1/2011 | ........... C12Q 1/6883 |
| WO | 2013/030841 | 3/2013 | |

OTHER PUBLICATIONS

Barber et al. GAPDH as a housekeeping gene: analysis of GAPDH mRNA expression in a panel of 72 human tissues. Physiological Genomics, vol. 21, No. 3, pp. 389-395, May 2005.*
Mailaparambil et al. Polymorphisms of interferons and their receptors in the genetics of severe RSV-associated diseases. Archives of Virology, vol. 153, No. 11, pp. 2133-2137, Oct. 2008.*
Platform GPL9188 (accessed from http://www.ncbi.nlm.nih.gov/geo/querry/acc.cgi?acc=GPL9188, publicly available Apr. 2010, printed as pp. 1/2-2/2, and including 120 pages of the GPL9188 gene table.*
Toukap et al. Identification of distinct gene expression profiles in the synovium of patients with system lupus erythematosus. Arthritis & Rheumatism, vol. 56, No. 5, pp. 1579-1588, May 2007.*
Rodríguez et al. Recommendations of the infectious diseases work group (GTEI) of the Spanish Society of Intensive and Critical Care Medicine and Coronary Units (SEMICYUC) and the Infections in Critically Ill Patients Study Group (GEIPC) . . . Medicina Intensiva, vol. 36, No. 2, pp. 103-137, Jan. 2012.*
Zaas et al. "Gene expression signatures diagnose influenza and other symptomatic respiratory viral infections in humans." Cell Host Microbe. Sep. 17, 2009;6(3)207-17.
Huang et al., "Temporal dynamics of host molecular responses differentiate symptomatic and asymptomatic influenza a infection." PLoS Genet. Aug. 2011;7(8):e1002234, printed as pp. 1/17-17/17.
International Preliminary Report on Patentability PCT Application No. PCT/AU2013/000765, dated Oct. 23, 2014, 31 pages.

(Continued)

*Primary Examiner* — Jennifer Dunston
(74) *Attorney, Agent, or Firm* — Casimir Jones, S.C.; Tanya A. Arenson

(57) ABSTRACT

The present invention relates to methods for the identification of clinical risk in patients having, or suspected of having, influenza. The invention also relates to methods for distinguishing between patients having influenza or viral pneumonia from patients having a symptomatically similar condition. The methods of the invention comprise determination of the level of expression of interferon alpha inducible protein 27 (IF127) in a biological sample from a patient having, or suspected of having, influenza. Kits comprising suitable components for the performance of the methods are also provided by the invention. The invention allows stratification of patients into groups defining clinical risk, for example groups based on the severity of risk to the long-term health of the subject.

11 Claims, 30 Drawing Sheets

(56) References Cited

OTHER PUBLICATIONS

International Search Report, International Patent Application No. PCT/AU2013/000765, dated Aug. 29, 2013, 5 pages.

Fjaerli, H. et al., "Whole blood gene expression in infants with respiratory syncytial virus bronchiolitis", BMC Infectious Diseases, 2006, vol. 6, Article 175, pp. 1-7.

Ioannidis, I et al., "Plasticity and Virus Specificity of the Airway Epithelial Cell Immune Response during Respiratory Virus Infection", Journal of Virology, 2012, vol. 86, pp. 5422-5436.

* cited by examiner

Day of Sample

Day of Sample

Figure 22

```
  1  gggaacacat ccaagcttaa gacggtgagg tcagcttcac attctcagga actctccttc
 61  tttgggtctg gctgaagttg aggatctctt actctctagg ccacggaatt aacccgagca
121  ggcatggagg cctctgctct cacctcatca gcagtgacca gtgtggccaa agtggtcagg
181  gtggcctctg gctctgccgt agttttgccc ctggccagga ttgctacagt tgtgattgga
241  ggagttgtgg ccatggcggc tgtgcccatg gtgctcagtg ccatgggctt cactgcggcg
301  ggaatcgcct cgtcctccat agcagccaag atgatgtccg cggcggccat tgccaatggg
361  ggtggagttg cctcgggcag ccttgtggct actctgcagt cactgggagc aactggactc
421  tccggattga ccaagttcat cctgggctcc attgggtctg ccattgcggc tgtcattgcg
481  aggttctact agctccctgc ccctcgccct gcagagaaga gaaccatgcc aggggagaag
541  gcacccagcc atcctgaccc agcgaggagc caactatccc aaatatacct ggggtgaaat
601  ataccaaatt ctgcatctcc agaggaaaat aagaaataaa gatgaattgt tgcaactctt
661  caaaa
```

Figure 23

```
  1  gggaacacat ccaagcttaa gacggtgagg tcagcttcac attctcagga actctccttc
 61  tttgggtctg gctgaagttg aggatctctt actctctagg ccacggaatt aacccgagca
121  ggcatggagg cctctgctct cacctcatca gcagtgacca gtgtggccaa agtggtcagg
181  gtggcctctg gctctgccgt agttttgccc ctggccagga ttgctacagt tgtgattgga
241  ggagttgtgg ctgtgcccat ggtgctcagt gccatgggct tcactgcggc gggaatcgcc
301  tcgtcctcca tagcagccaa gatgatgtcc gcggcggcca ttgccaatgg gggtggagtt
361  gcctcgggca gccttgtggc tactctgcag tcactgggag caactggact ctccggattg
421  accaagttca tcctgggctc cattgggtct gccattgcgg ctgtcattgc gaggttctac
481  tagctccctg cccctcgccc tgcagagaag agaaccatgc caggggagaa ggcacccagc
541  catcctgacc cagcgaggag ccaactatcc caaatatacc tggggtgaaa tataccaaat
601  tctgcatctc cagaggaaaa taagaaataa agatgaattg ttgcaactct tcaaaa
```

Figure 24

MEASALTSSAVTSVAKVVRVASGSAVVLPLARIATVVIGGVVAM
AAVPMVLSAMGFTAAGIASSSIAAKMMSAAAIANGGGVASGSLVATLQSLGATGLSG
LTKFILGSIGSAIAAVIARFY

Figure 25

MEASALTSSAVTSVAKVVRVASGSAVVLPLARIATVVIGGVVAV
PMVLSAMGFTAAGIASSSIAAKMMSAAAIANGGGVASGSLVATLQSLGATGLSGLTK
FILGSIGSAIAAVIARFY

Figure 26

Target region of IFI27

ACCTCATCAGCAGTGACCAGTgtggccaaagtggtcagggtggcctctgg ctctgccgtagttttgccctggccaggattgctacagttgtgattggag gagttgtggctgtgcccatggtgctcagtgccatgggcttcactgcggcg ggaatcgcctcgtcctCCATAGCAGCCAAGATGATGT

Figure 27

Target region of GAPDH (genomic sequence)

AAATTGAGCCCGCAGCCTCCCGCTTCGCTCTCTGCTCCTCCTGTTCGACA
GTCAGCCGCATCTTCTTTTGCGTCGCCAGgtgaagacgggcggagagaaa
cccggggaggctagggacggcctgaaggcggcaggggcgggcgcaggccgg
atgtgttcgcgccgctgcggggtgggcccgggcggcctccgcattgcagg
ggcgggcggaggacgtgatgcggcgcgggctgggcatggaggcctggtgg
gggaggggaggggaggcgtgtgtgtcggccggggccactaggcgctcact
gttctctcctccgcgcagCCGAGCCACATCGCTCAGACACCATGGGGAA
GGTGAAGGTCGGAGTCAACGGgtgagttcgcgggtggctgggggccctg
ggctgcgaccgcccccgaaccgcgtctacgagccttgcgggctccgggtc
tttgcagtcgtatggggcagggtagctgttccccgcaaggagagctcaa
ggtcagcgctcggacctggcggagcccgcacccaggctgtggcgccctg
tgcagctccgcccttgcggcgccatctgcccggagcctccttcccctagt
ccccagaaacaggaggtccctactcccgcccgagatcccgacccggaccc
ctaggtgggggacgctttctttcctttcgcgctctgcggggtcacgtgtc
gcagaggagcccctcccccacggcctccggcaccgcaggcccccgggatgc
tagtgcgcagcgggtgcatccctgtccggatgctgcgcctgcggtagagc
ggccgccatgttgcaaccgggaaggaaatgaatgggcagccgttaggaaa
gcctgccggtgactaaccctgcgctcctgcctcgatgggtggagtcgcgt
gtggcggggaagtcaggtggagcgaggctagctggcccgatttctcctcc
gggtgatgcttttcctagattattctctggtaaatcaaagaagtgggttt
atggaggtcctcttgtgtcccctcccgcagaggtgtggtggctgtggca
tggtgccaagccgggagaagctgagtcatgggtagttggaaaaggacatt
tccaccgcaaaatggcccctctggtggtggccccttcctgcagcgccggc
tcacctcacggccccgcccttcccctgccagcctagcgttgacccgaccc
caaaggccaggctgtaaatgtcaccgggaggattgggtgtctgggcgcct
cggggaacctgcccttctccccattccgtcttccggaaaccagatctccc
accgcaccctggtctgaggttaaatatagctgctgacctttctgtagctg
ggggcctgggctggggctctctcccatcccttctccccacacacatgcac
ttacctgtgctcccactcctgatttctggaaaagagctaggaaggacagg
caacttggcaaatcaaagccctgggactagggggttaaaatacagcttcc
cctcttcccacccgcccagtctctgtcccttttgtaggagggacttaga
gaagggtgggcttgccctgtccagttaatttctgacctttactcctgcc
ctttgagtttgatgatgctgagtgtacaagcgttttctccctaaagggtg
cagctgagctaggcagcagcaagcattcctggggtggcatagtggggtgg
tgaataccatgtacaaagcttgtcccagactgtgggtggcagtgcccca
catggccgcttctcctggaagggcttcgtatgactgggggtgttgggcag
ccctggagccttcagttgcagccatgccttaagccaggccagcctggcag

Figure 27 (continuation)

ggaagctcaagggagataaaattcaacctcttgggccctcctgggggtaa
ggagatgctgcattcgccctcttaatggggaggtggcctagggctgctca
catattctggaggagcctcccctcctcatgccttcttgcctcttgtctct
tag<u>ATTTGGTCGTATTGGG</u>CGCCTGGTCACCAGGGCTGCTTTTAACTCTG
GTAAAGTGGATATTGTTGCCATCAATGACCCCTTCATTGACCTCAACTAC
ATGgtgagtgctacatggtgagccccaaagctggtgtgggaggagccacc
tggctgatgggcagcccttcataccctcacgtattcccccagGTTTACA
TGTTCCAATATGATTCCACCCATGGCAAATTCCATGGCACCGTCAAGGCT
GAGAACGGGAAGCTTGTCATCAATGGAAATCCCATCACCATCTTCCAGGA
gtgagtggaagacagaatggaagaaatgtctttggggaggcaactagga
tggtgtggctcccttgggtatatggtaaccttgtgtccctcaatatggtc
ctgtccccatctcccccccaccccatag<u>GCGAGATCCCTCCAAAATCAA</u>
GTGGGGCGATGCTGGCGCTGAGTACGTCGTGGAGTCCACTGGCGTCTTCA
CCACCATGGAGAAGGCTGGGgtgagtgcaggagggcccgcgggagggaa
gctgactcagccctgcaaaggcaggacccgggttcataactgtctgcttc
tctgctgtagGCTCATTTGCAGGGGGGAGCCAAAAGGGTCATCATCTCTG
CCCCCTCTGCTGATGCCCCCATGTTCGTCATGGGTGTGAACCATGAGAAG
TATGACAACAGCCTCAAGATCATCAGgtgaggaaggcagggcccgtggag
aagcggccagcctggcacccatggacacgctccctgacttgcgccccg
ctccctctttctttgcagCAATGCCTCCTGCACCACCAACTGCTTAGCAC
CCCTGGCCAAGGTCATCCATGACAACTTTGGTATCGTGGAAGGACTCATG
gtatgagagctggggaatgggactgaggctcccacctttctcatccaaga
ctggctcctccctgccggggctgcgtgcaaccctggggttgggggttctg
gggactggctttcccataatttcctttcaaggtggggagggaggtagagg
ggtgatgtggggagtacgctgcagggcctcactccttttgcagACCACAG
TCCATGCCATCACTGCCACCCAGAAGACTGTGGATGGCCCCTCCGGGAAA
CTGTGGCGTGATGGCCGCGGGGCTCTCCAGAACATCATCCCTGCCTCTAC
TGGCGCTGCCAAGGCTGTGGGCAAGGTCATCCCTGAGCTGAACGGGAAGC
TCACTGGCATGGCCTTCCGTGTCCCCACTGCCAACGTGTCAGTGGTGGAC
CTGACCTGCCGTCTAGAAAAACCTGCCAAATATGATGACATCAAGAAGGT
GGTGAAGCAGGCGTCGGAGGGCCCCCTCAAGGGCATCCTGGGCTACACTG
AGCACCAGGTGGTCTCCTCTGACTTCAACAGCGACACCCACTCCTCCACC
TTTGACGCTGGGGCTGGCATTGCCCTCAACGACCACTTTGTCAAGCTCAT
TTCCTGgtatgtggctggggccagagactggctcttaaaaagtgcagggt
ctggcgccctctggtggctggctcagaaaaagggccctgacaactctttt
catcttctagGTATGACAACGAATTTGGCTACAGCAACAGGGTGGTGGAC
CTCATGGCCCACATGGCCTCCAAGGAGTAAGACCCCTGGACCACCAGCCC
CAGCAAGAGCACAAGAGGAAGAGAGAGACCCTCACTGCTGGGGAGTCCCT
GCCACACTCAGTCCCCCACCACACTGAATCTCCCCTCCTCACAGTTGCCA
TGTAGACCCCTTGAAGAGGGGAGGGGCCTAGGGAGCCGCACCTTGTCATG
TACCATCAATAAAGTACCCTGTGCTCAACC

Figure 28

```
   1  ggctgggact ggctgagcct ggcgggaggc ggggtccgag tcaccgcctg ccgccgcgcc
  61  cccggtttct ataaattgag cccgcagcct cccgcttcgc tctctgctcc tcctgttcga
 121  cagtcagccg catcttcttt tgcgtcgcca gccgagccac atcgctcaga caccatgggg
 181  aaggtgaagg tcggagtcaa cggatttggt cgtattgggc gcctggtcac cagggctgct
 241  tttaactctg gtaaagtgga tattgttgcc atcaatgacc ccttcattga cctcaactac
 301  atggtttaca tgttccaata tgattccacc catggcaaat tcatggcac cgtcaaggct
 361  gagaacggga agcttgtcat caatggaaat cccatcacca tcttccagga gcgagatccc
 421  tccaaaatca gtgggcga tgctggcgct gagtacgtcg tggagtccac tggcgtcttc
 481  accaccatgg agaaggctgg ggctcatttg caggggggag ccaaaagggt catcatctct
 541  gccccctctg ctgatgcccc catgttcgtc atgggtgtga accatgagaa gtatgacaac
 601  agcctcaaga tcatcagcaa tgcctcctgc accaccaact gcttagcacc cctggccaag
 661  gtcatccatg acaactttgg tatcgtggaa ggactcatga ccacagtcca tgccatcact
 721  gccacccaga agactgtgga tggcccctcc gggaaactgt ggcgtgatgg ccgcggggct
 781  ctccagaaca tcatccctgc ctctactggc gctgccaagg ctgtgggcaa ggtcatccct
 841  gagctgaacg ggaagctcac tggcatggcc ttccgtgtcc ccactgccaa cgtgtcagtg
 901  gtggacctga cctgccgtct agaaaaacct gccaaatatg atgacatcaa gaaggtggtg
 961  aagcaggcgt cggagggccc cctcaagggc atcctgggct acactgagca ccaggtggtc
1021  tcctctgact caacagcga cacccactcc tccaccttg acgctgggc tggcattgcc
1081  ctcaacgacc actttgtcaa gctcatttcc tggtatgaca cgaatttgg ctacagcaac
1141  agggtggtgg acctcatggc ccacatggcc tccaaggagt aagaccctg gaccaccagc
1201  cccagcaaga gcacaagagg aagagagaga ccctcactgc tggggagtcc ctgccacact
1261  cagtccccca ccacactgaa tctcccctcc tcacagttgc catgtagacc ccttgaagag
1321  gggaggggcc tagggagccg caccttgtca tgtaccatca ataaagtacc ctgtgctcaa
1381  ccaaaaaaaa aaaaaaaaa a
```

Figure 29

```
   1  gtgcgcagcg ggtgcatccc tgtccggatg ctgcgcctgc ggtagagcgg ccgccatgtt
  61  gcaaccggga aggaaatgaa tgggcagccg ttaggaaagc ctgccggtga ctaaccctgc
 121  gctcctgcct cgatgggtgg agtcgcgtgt ggcggggaag tcaggtggag cgaggctagc
 181  tggcccgatt tctcctccgg gtgatgcttt cctagatta ttctctgatt tggtcgtatt
 241  gggcgcctgg tcaccagggc tgctttaac tctggtaaag tggatattgt tgccatcaat
 301  gaccccttca ttgacctcaa ctacatggtt tacatgttcc aatatgattc cacccatggc
 361  aaattccatg gcaccgtcaa ggctgagaac gggaagcttg tcatcaatgg aaatcccatc
 421  accatcttcc aggagcgaga tccctccaaa atcaagtggg gcgatgctgg cgctgagtac
 481  gtcgtggagt ccactggcgt cttcaccacc atggagaagg ctgggctca tttgcagggg
 541  ggagccaaaa gggtcatcat ctctgccccc tctgctgatg ccccatgtt cgtcatgggt
 601  gtgaaccatg agaagtatga caacagcctc aagatcatca gcaatgcctc ctgcaccacc
 661  aactgcttag cacccctggc caaggtcatc catgacaact tggtatcgt ggaaggactc
 721  atgaccacag tccatgccat cactgccacc cagaagactg tggatggccc ctccgggaaa
 781  ctgtggcgtg atggccgcgg ggctctccag aacatcatcc ctgcctctac tggcgctgcc
 841  aaggctgtgg gcaaggtcat ccctgagctg aacgggaagc tcactggcat ggccttccgt
 901  gtccccactg ccaacgtgtc agtggtggac ctgacctgcc gtctagaaaa acctgccaaa
 961  tatgatgaca tcaagaaggt ggtgaagcag gcgtcggagg ccccctcaa gggcatcctg
1021  ggctacactg agcaccaggt ggtctcctct gacttcaaca gcgacaccca ctcctccacc
1081  tttgacgctg gggctggcat tgccctcaac gaccactttg tcaagctcat ttcctggtat
1141  gacaacgaat tggctacag caacaggtg gtggacctca tggcccacat ggcctccaag
1201  gagtaagacc cctggaccac cagcccagc aagagcacaa gaggaagaga gagaccctca
1261  ctgctgggga gtccctgcca cactcagtcc cccaccacac tgaatctccc ctcctcacag
1321  ttgccatgta gacccttga agaggggagg ggcctaggga ccgcaccctt gtcatgtacc
1381  atcaataaag taccctgtgc tcaaccaaaa aaaaaaaaaa aaaaa
```

RISK STRATIFICATION IN INFLUENZA

CROSS-REFERENCE TO RELATED APPLICATIONS

The present application is a national phase application under 35 U.S.C. § 371 of PCT International Application No. PCT/AU2013/000765, international filing date Jul. 10, 2013, which claims priority to Australian provisional patent application number 2012902954 filed on Jul. 10, 2012, the entire contents of which are incorporated by reference in their entireties.

REFERENCE TO AN ELECTRONIC SEQUENCE LISTING

The contents of the Sequence Listing submitted electronically as an ASCII text file via EFS-Web with the Name: p017395C_ST25corrected.txt; Size: 13,000 bytes; and Date of Creation: Jan. 20, 2015 is incorporated herein by reference.

TECHNICAL FIELD

The present invention relates to methods for the identification of clinical risk in patients having, or suspected of having, influenza. The invention also relates to methods for distinguishing between patients having influenza or viral pneumonia from patients having a symptomatically similar condition. The methods of the invention comprise determination of the level of expression of interferon alpha inducible protein 27 (IFI27) in a biological sample from a patient having, or suspected of having, influenza. Kits comprising suitable components for the performance of the methods are also provided by the invention. The invention allows stratification of patients into groups defining clinical risk, for example groups based on the severity of risk to the long-term health of the subject.

BACKGROUND

Influenza/Pneumonia have been reported to rank eighth in the top ten causes of death in the USA. Influenza virus infection represents the most common infectious disease affecting the greatest number of people each year globally. Influenza rapidly spreads globally in seasonal epidemics and imposes considerable burden of hospitalization. Although difficult to assess globally, the World Health Organization (WHO) estimates annual epidemics morbidity of between 3 to 5 million cases of severe illness, and mortality between 250,000 to 500,000 deaths globally annually. In the US, influenza epidemics have been estimated by WHO to affect 5-15% of the US population with upper respiratory tract infections, with hospitalization and deaths mainly in high-risk groups (such as the elderly and the chronically ill), and a consequential cost of US$71-167 billion annually for the US economy. Most deaths from influenza in industrialized countries occur in elderly people over age 65. The prevalence of infections and their potential severity in terms of patient suffering, with consequential economic costs, has made their detection and treatment a priority for healthcare systems.

From the clinical perspective failure to identify patients with an influenza infection that have a higher risk of developing a severe disease delays the delivery of treatment appropriate for such high risk patients, and may have profound consequences for the recovery and long-term health of the patient. Among patients who progressed to severe disease, an average delay of 5-7 days has been consistently reported in the literature. Avoiding treatment delays in patients at risk of progressing to severe disease is critically important because timely administration of intensive care therapy is associated with a reduced risk of death from influenza. For example, it has recently been reported that a delay of one day from onset of symptom to hospital admission increased the risk of death from (H1N1) influenza by 5.5%[1].

Often, influenza infection is suspected on clinical grounds alone (e.g. history of flu-like symptoms) and the individual is treated with anti-viral medications without any formal laboratory testing. The clinical decision is therefore not necessarily about whether the individual has influenza virus, but whether the individual should be admitted to hospital, or safely return home. In this context, diagnostic testing for the presence of the influenza virus may be superfluous. Instead, clinicians need a test that can assist them to quantify how adequately a patient will respond to an influenza infection, which ultimately determines the severity of the disease. The greater the severity of disease, the more likely the infected subject will deteriorate, and hence need hospital admission.

Currently, there are some laboratory methods that can reliably assess the severity of the influenza infection. One example of a method that assesses the severity of influenza infection involves testing the viral load in the airway sample as the extent of viral replication in influenza has been thought to correlate with disease severity. However, study on airway and serum samples has shown that viral loads are the same regardless of disease severity[2,12]. This demonstrates that the severity of an influenza infection does not necessarily correlate with the severity of the disease that manifests as a result of the infection.

Hence, for various reasons, although diagnostic tests can determine the presence or absence of the influenza virus and therefore may assist the clinician, they can be inadequate in making an impact on the clinical decisions as the presence of the virus may not always equate to an abnormal immune response which may be the actual cause of the disease progression in an infected patient.

In order to provide timely and appropriate treatment of individuals with a confirmed influenza infection or who are symptomatic of an influenza infection, a specific test that assesses disease severity or potential disease severity due to the infection is needed. Such a severity stratification tool will assist the management of such patients. It allows clinicians to identify those patients who can be safely discharged home, whilst those identified with more severe disease or have a higher risk of developing a more severe disease are admitted to the hospital for further observation and treatment. It also gives doctors the opportunity to employ preventative measures to halt or slow disease progression in patients that may be only mildly symptomatic, but would be likely to develop a severe disease.

There is a need for improved methods for assessment of individuals having, or suspected of having, influenza in order to assist the provision of prognostic and diagnostic information to aid clinical decision-making.

SUMMARY

The present inventors have recognised that a method that could distinguish between influenza patients (whether or not they are confirmed and/or symptomatic) that would likely require medical intervention in a hospital or clinical environment and those that could likely safely return home, prior to the patient showing any indication of a severe disease, would greatly assist doctors in making better treatment decisions.

The present invention is based, at least in part, on the identification by the inventors that the expression level of interferon alpha induced protein 27 (IFI27) gene in a subject correlates with the severity of the disease caused by the influenza infection in that subject. The correlation may be used to predict the severity of disease arising from the infection in a subject prior to the subject being symptomatic of an influenza infection or of severe disease. The invention relates to methods for the detection of a particular aspect of the host response during influenza infection that may be indicative of an inadequate response by the patient and a likelihood of developing a severe disease that requires medical intervention in a hospital or clinical environment. In embodiments, the methods of the invention may be used to assess patients with influenza infection to determine which individuals have a clinical risk, being those more likely to develop a serious disease arising from the infection, characterised by the need for medical intervention such as hospital admission or even life-support therapy.

The invention has applications in healthcare, such as in the early management of influenza infection, in monitoring a patient's immune response to the infection, and in enabling life-saving intervention to at-risk individuals who may otherwise be missed by traditional diagnostic approaches. The inventors envisage that in patients presenting to a doctor's surgery or hospital with suspected influenza infection, IFI27 gene-expression level can assist the clinician to predict whether a patient can be safely discharged home or may need admission to hospital. In this scenario, a normal level of IFI27 expression may be indicative that a patient either does not have influenza or does have influenza but does not have a higher risk of developing a severe disease, in which case, they may be discharged. However, an upregulated level of IFI27 expression may be indicative of a patient with an influenza infection and a higher risk of developing a severe disease, in which case, the patient may require medical intervention in a hospital or clinical environment.

For example, a patient may present to a doctor's surgery with a suspected influenza infection, and relatively mild symptoms of the infection which would ordinarily result in the patient being sent home with minimal medication. However, the present invention may be used to determine if the patient has clinical risk, in which case the treating physician could intervene at this early stage and admit the patient to hospital for monitoring and treatment, prior to the infection manifesting into a serious disease.

In another example, a patient may present at a hospital and be confirmed to have an influenza infection, and may show some symptoms that are consistent with the development of a serious disease. Ordinarily, this may result in the patient being admitted to hospital for treatment. However, the present invention may be used to predict whether the patient is actually likely to develop a severe disease as a result of the influenza infection, which could assist clinicians in the appropriate allocation of staff and resources. Accordingly, the present invention may prevent over-management of said patient where it is predicted the patient does not have clinical risk and will not develop a severe disease as a result of the infection.

In a further example, the inventors envisage that the present invention may provide a useful screening tool in times of influenza epidemics or pandemics, when it may not be feasible to determine if individuals are infected with influenza, and clinical resources need to be reserved for patients at clinical risk. In these scenarios, the present invention may be used to screen individuals or groups of individuals that may or may not show any sign of an influenza infection to determine if they have a clinical risk of developing severe disease as a result of an influenza infection. During the screens, a normal level of IFI27 expression may be indicative that a patient either does not have influenza or does have influenza and is not at clinical risk of developing a severe disease, in which case, their monitoring or treatment can be deprioritised. However, an upregulated level of IFI27 expression may be indicative of a patient with an influenza infection and a higher risk of developing a severe disease, hence a patient with clinical risk, in which case the patient can be further monitored and treated.

Similarly, the inventors envisage that in patients who are admitted to hospital due to an influenza infection, IFI27 gene-expression level can assist the clinician to predict the adequacy of the patient's immune response and whether a patient will deteriorate further or recover. In the instance where it is predicted that the patient will deteriorate further, appropriate therapeutic protocols can be implemented for the patient, such as admission to an intensive care unit. Alternatively, a determination that the patient is likely to recover will allow for the patient to remain in a standard hospital ward, as opposed to potentially occupying useful resources in the intensive care unit. The inventors envisage that IFI27 gene-expression level may also be used to assist the clinician in the ongoing monitoring of a patient, for example after anti-viral therapy or other care associated with the treatment of the patient's condition.

In embodiments, the invention provides a gene-expression assay to measure the level of mRNA expression of IFI27 in individuals suspected of influenza infection. High level of IFI27 gene expression indicates a significantly increased risk of immune decompensating and hence warns physicians of impending deterioration in the patient's clinical status. Measurement of IFI27 gene expression assists physicians in their clinical decision-making by accurately distinguishing individuals who present a clinical risk of developing severe disease and need admission to hospital from those who can be safely discharged home (i.e. risk stratification). This invention therefore has practical use also in the initial triage of patients during influenza epidemics and pandemics.

In one aspect the invention provides a method for identifying clinical risk in a patient having or suspected of having an influenza infection, the method comprising determining the expression level of interferon alpha inducible protein 27 (IFI27) gene in a biological sample from said patient and comparing the determined level of IFI27 gene product to a standard level.

In an embodiment, the patient has or is suspected of having an influenza A or influenza B infection, or a sub-type thereof. In an embodiment, the sub-type is a seasonal strain of influenza A. In an embodiment, the sub-type is a seasonal strain of influenza B.

In an embodiment, standard level of IFI27 gene product is indicative of no clinical risk, and an elevated level of IFI27 gene product in said patient sample compared to said standard level is indicative of clinical risk in said patient.

In an embodiment the standard level indicative of no clinical risk is based on the level of IFI27 in healthy subjects.

In an embodiment the standard level is based on the level of IFI27 in subjects infected with influenza virus who are asymptomatic and an elevated level of IFI27 in said patient sample compared to said standard level is indicative of clinical risk in said patient.

In an embodiment, the standard level of IFI27 gene product is indicative of clinical risk, and an equal or elevated level of IFI27 gene product in said patient sample compared to said standard level is indicative of clinical risk in said patient.

In an embodiment the standard level is prepared at the same time as determining the expression level of IFI27 gene in the biological sample from said patient.

In an embodiment, a level of IFI27 gene product that is at least 40 to 60 times higher than the standard level based on healthy subjects or subjects infected with influenza who are asymptomatic, is indicative of clinical risk.

In an embodiment, a level of IFI27 gene product that is at least 60 times higher than the standard level based on healthy subjects or subjects infected with influenza who are asymptomatic, is indicative of clinical risk.

In an embodiment the standard level is prepared by subjecting one or more known sample(s) of an IFI27 gene product to the same methods for determining IFI27 gene expression level as the biological sample from said patient, wherein the one or more known sample(s) of an IFI27 gene product are of a pre-determined amount or amounts indicative of clinical risk, and an equal or elevated level of IFI27 gene product in said patient sample compared to said standard level is indicative of clinical risk in said patient.

In an embodiment the standard level is prepared by subjecting one or more known sample(s) of an IFI27 gene product to the same methods for determining IFI27 gene expression level as the biological sample from said patient, wherein the one or more known sample(s) of an IFI27 gene product are of a pre-determined amount or amounts indicative of no clinical risk, and an elevated level of IFI27 in said patient sample compared to said standard level is indicative of clinical risk in said patient.

In an embodiment the invention provides a method of monitoring the progress of a patient having influenza, the method comprising determining the expression level of IFI27 gene in a first biological sample from said patient and determining the expression level of IFI27 gene in a second biological sample from said patient, wherein the first and second samples are obtained from the patient at different times, and assessing the patient status on the basis of the relative expression levels of IFI27 in the first and second samples. In an embodiment, an increase in the expression level of IFI27 gene in said second biological sample compared to said first biological sample is indicative of an increased clinical risk in said patient. In an embodiment, a decrease in the expression level of IFI27, gene in said second biological sample compared to said first biological sample is indicative of a decreased clinical risk in said patient.

In another aspect the invention provides a method for identifying influenza or viral pneumonia in a patient, the method comprising determining the expression level of interferon alpha inducible protein 27 (IFI27) gene in a biological sample from said patient and comparing the determined level of IFI27 gene product to a standard level of IFI27 gene product.

In an embodiment the standard level of IFI27 gene product is based on the level of IFI27 in healthy subjects and an elevated expression level of IFI27 in said patient sample compared to said standard level is indicative of influenza or viral pneumonia in said patient.

In an embodiment the patient is suspected of having viral pneumonia or bacterial pneumonia.

In an embodiment the invention provides a method for the identification of influenza or viral pneumonia, wherein the standard level is based on the level of IFI27 gene product in subjects with bacterial pneumonia, and an elevated level of IFI27 gene product in said patient sample compared to said standard level is indicative of a patient with influenza or viral pneumonia.

In an embodiment, a level of IFI27 gene product that is at least 10 times higher than a standard level based on healthy subjects or subjects with bacterial pneumonia is indicative of influenza or viral pneumonia.

In an embodiment, a level of IFI27 gene product that is at least 40 to 60 times higher than a standard level based on healthy subjects or subjects with bacterial pneumonia is indicative of a patient with influenza or viral pneumonia, and clinical risk.

In an embodiment, a level of IFI27 gene product that is at least 60 times higher than a standard level based on healthy subjects or subjects with bacterial pneumonia is indicative of a patient with influenza or viral pneumonia, and clinical risk.

The following embodiments apply to all aspects of the invention described herein.

In an embodiment the method further comprises determining the expression level of at least one additional gene(s) in said biological sample. In an embodiment the at least one additional gene(s) is a gene the expression of which is constitutive. In an embodiment the at least one additional gene is a gene the expression of which is unaffected by influenza infection. In an embodiment the at least one additional gene(s) is GAPDH gene.

In an embodiment the biological sample is blood, or a component thereof such as blood cell subsets. In an embodiment the biological sample comprises a subset of white blood cells.

In an embodiment the method comprises processing a blood sample from said patient to enrich for the presence of plasmacytoid dendritic cells (pCDs).

In an embodiment the method comprises contacting the biological sample with an agent capable of binding to an IFI27 gene product and detecting binding between the agent and the IFI27 gene product.

In an embodiment the biological sample is RNA, mRNA, or protein.

In an embodiment the IFI27 gene product is an IFI27 mRNA or fragment thereof. In an embodiment the IFI27 gene product comprises a nucleic acid sequence of SEQ ID NO:1 or a fragment or variant thereof. In an embodiment the IFI27 gene product comprises a nucleic acid sequence of SEQ ID NO:2 or a fragment or variant thereof. In an embodiment the IFI27 gene product is the isoform 1 transcript variant. In an embodiment the IFI27 gene product is the isoform 2 transcript variant.

In an embodiment the IFI27 gene product is an IFI27 polypeptide or a fragment or variant thereof. In an embodiment the IFI27 gene product comprises an amino acid sequence comprising the sequence of SEQ ID NO:3 or a fragment or variant thereof. In an embodiment the IFI27 gene product comprises an amino acid sequence comprising the sequence of SEQ ID NO:4 or a fragment or variant thereof.

In an embodiment the method comprises reverse transcription of mRNA to cDNA. In an embodiment the IFI27 cDNA sequence comprises a sequence of SEQ ID NO:5 or a fragment or variant thereof. In an embodiment the IFI27 cDNA sequence comprises a sequence of SEQ ID NO:6 or a fragment or variant thereof. In an embodiment the method comprises amplification of an IFI27 nucleic acid sequence, such as cDNA sequence, of the sample and detecting an amplified sequence. In an embodiment the amplification comprises polymerase chain reaction (PCR). In an embodiment the polymerase chain reaction comprises quantitative polymerase chain reaction (qPCR). In an embodiment the polymerase chain reaction may utilise one or more primers capable of amplifying a nucleic acid sequence selected from the sequences of (i) SEQ ID NO:1, (ii) SEQ ID NO:2, (iii) SEQ ID NO:5, (iv) SEQ ID NO:6, and (v) or a fragment or variant of any of SEQ ID NO: 1, SEQ ID NO:2, SEQ ID NO:5, SEQ ID NO:6.

In an embodiment the polymerase chain reaction may utilize one or both of the primer sequences of SEQ ID NO:7 (acctcatcagcagtgaccagt) and SEQ ID NO:8 (acatcatcttggctgctatgg), or a sequence variant thereof capable of amplifying the same target sequence. In an embodiment the polymerase chain reaction may utilize one or both of the primer sequences of SEQ ID NO:9 (TGCCTCGGGCAGCCT) and SEQ ID NO:10 (TTGGTCAATCCGGAGAGTCC), or a sequence variant thereof capable of amplifying the same target sequence.

In an embodiment the method comprises contacting the sample with one or more probe(s) capable of specifically binding to an IFI27 gene product or fragment or variant thereof. In an embodiment the one or more probe(s) is a nucleic acid comprising (i) a sequence complementary to the sequence shown in SEQ ID NO:1 or (ii) a sequence complementary to the sequence shown in SEQ ID NO:2, or a fragment or variant of (i) or (ii). In an embodiment the one or more probe(s) is a nucleic acid comprising (i) a sequence complementary to the sequence shown in SEQ ID NO:5 or (ii) a sequence complementary to the sequence shown in SEQ ID NO:6 or a fragment or variant of (i) or (ii). In an embodiment the nucleic acid probe comprises 10 to 50 bases. In an embodiment the nucleic acid probe comprises 30 to 600 bases.

In an embodiment the method comprises the steps of (i) obtaining a blood sample from a patient having or suspected of having an influenza infection; (ii) preparing an isolate of total RNA from said blood sample; (iii) preparing cDNA by reverse transcription of said total RNA isolate; (iv) amplifying an IFI27 nucleic acid sequence by polymerase chain reaction; (v) comparing the level of said amplified IFI27 nucleic acid sequence to a standard; (vi) determining if said patient has clinical risk on the basis of said comparing. In an embodiment the polymerase chain reaction is quantitative polymerase chain reaction. In an embodiment, the standard may be based on a standard level of IFI27 gene product that is indicative of clinical risk or is indicative of no clinical risk.

In an embodiment the method comprises determining the level of an IFI27 polypeptide, or fragment thereof. In an embodiment the method comprises determining the level of an IFI27 polypeptide comprising (i) the amino acid sequence of SEQ ID NO:3 or (ii) the amino acid sequence of SEQ ID NO:4, or an antigenic fragment or variant of (i) or (ii). In an embodiment the method comprises contacting the sample with an antibody capable of selectively binding to an IFI27 polypeptide comprising an amino acid sequence shown in SEQ ID NO:3 or SEQ ID NO:4, or an antigenic fragment or variant thereof.

In an embodiment the method comprises one or more of gel electrophoresis, nucleic acid sequencing and amino acid sequencing.

In an embodiment the method is performed entirely ex vivo. In an embodiment comparing the level of determined IFI27 gene product in a biological sample to a standard level is done with the assistance of a computer program. In an embodiment allocating a clinical risk to a patient on the basis of the comparison is done with the assistance of a computer program.

In a second aspect, there is provided a kit for determining the level of an interferon alpha inducible protein 27 (IFI27) gene product in a biological sample, the kit comprising at least one agent for detecting the presence of an IFI27 gene product.

In an embodiment the at least one agent is a primer, antibody or probe. In an embodiment the primer or probe is specific for a nucleic acid sequence selected from the sequences shown in SEQ ID NO:1, SEQ ID NO:2, SEQ ID NO:5, SEQ ID NO:6, or a variant or fragment thereof. In an embodiment the kit comprises a forward and a reverse primer capable of selectively amplifying a nucleic acid sequence selected from the sequences shown in SEQ ID NO:1, SEQ ID NO:2, SEQ ID NO:5, SEQ ID NO:6, or a variant or fragment thereof.

In an embodiment the kit comprises one or more nucleic acid sequences selected from the group consisting of SEQ ID NO:7 (acctcatcagcagtgaccagt), SEQ ID NO:8 (acatcatcttggctgctatgg), SEQ ID NO:9 (TGCCTCGGGCAGCCT) and SEQ ID NO:10 (TTGGTCAATCCGGAGAGTCC), or a sequence variant thereof capable of specifically binding the same target sequence.

In one embodiment the kit comprises multiple agents capable of detecting the presence of an interferon alpha inducible protein 27 (IFI27) gene product in a biological sample.

In an embodiment the kit comprises an antibody capable of specifically binding to a polypeptide, or fragment or variant thereof, encoded by an IFI27 gene sequence. In an embodiment the antibody is a conjugated antibody specific for IFI27. In one embodiment the antibody is a polyclonal antibody. In an embodiment the polyclonal antibody is a rabbit polyclonal antibody. In one embodiment the antibody is a monoclonal antibody. In an embodiment the antibody binds to the epitope sequence:

MEASALTSSAVTSVAKVVRVASGSAVVLPLARIATVVIGGVVAVPMVLSA

MGFTAAGIASSSIAAKMMSAAAIANGGGVASGSLVATLQSLGATGLSGLT

KFILGSIGSAIAAVIARFY (SEQ ID NO:4).

In one embodiment the antibody is capable of selectively binding to (i) an IFI27 polypeptide comprising an amino acid sequence shown in SEQ ID NO:3 or (ii) an IFI27 polypeptide comprising an amino acid sequence shown in SEQ ID NO:4, or (iii) an antigenic fragment or variant of (i) or (ii).

In an embodiment the kit comprises one or more agents for normalisation of said method. In one embodiment the agent(s) for normalisation are selected from the group consisting of an agent or agents for the detection of a constitutively expressed gene product. In one embodiment the constitutively expressed gene product is GAPDH.

In one embodiment the kit comprises one or more calibrated standards wherein the standard comprises a known concentration of IFI27 gene product. In an embodiment, the known concentration of IFI27 gene product is an amount indicative of an individual having negligible clinical risk of severe disease from influenza infection, or an amount indicative of an individual at clinical risk of severe disease from influenza infection.

In an embodiment, the calibrated standards encompass a range of indicative amounts of IFI27 gene product, such as an amount indicative of negligible clinical risk, an amount indicative of about 5 to 10 fold more than that which is typical of a healthy individual, an amount indicative of about 10 to 20 fold more than that which is typical of a healthy individual, an amount indicative of about 20 to 40 fold more than that which is typical of a healthy individual, an amount indicative of about 30 to 60 fold more than that which is typical of a healthy individual, an amount indicative of about 50 to 60 fold more than that which is typical of a healthy individual, an amount indicative of about 50 to 100 fold more than that which is typical of a healthy individual an amount indicative of about 100 to 200 fold more than that which is typical of a healthy individual, an amount indicative of about 150 to 600 fold more than that which is typical of a healthy individual, or an amount indicative of about 500 to 1000 fold more than that which is typical of a healthy individual.

In an embodiment, the calibrated standards encompass a range of indicative amounts of IFI27 gene product, such as an amount indicative of clinical risk, an amount indicative of about 1 to 2 fold more than that which is typical of an individual with influenza infection and clinical risk, an amount indicative of about 2 to 4 fold more than that which is typical of an individual with influenza infection and clinical risk, an amount indicative of about 3 to 6 fold more than that which is typical of an individual with influenza infection and clinical risk, an amount indicative of about 5 to 10 fold more than that which is typical of an individual with influenza infection and clinical risk, or an amount indicative of about 10 to 20 fold more than that which is typical of an individual with influenza infection and clinical risk.

In one embodiment the kit comprises one or more additional components selected from the group consisting of (i) one or more reference sample(s); (ii) one or more detectable moieties; (iii) one or more substance(s) for immobilising an agent for detecting an IFI27 gene product on a solid support; (iv) a solid support material; (v) one or more container(s) for collection and/or storage of a biological sample; (vi) one or more reagent(s) for use in preparation of a biological sample; (vii) one or more agents for the amplification of a nucleic acid sequence; and (viii) instructions for use of the kit or a component(s) thereof in a method for determining the level of an IFI27 gene product in a biological sample.

In a further aspect there is provided a method for assessing the efficacy of an agent for treatment of influenza, the method comprising administering said agent to an individual having an influenza infection and determining the level of an IFI27 gene product in a biological sample from said individual and comparing said determined level of IFI27 gene product to a standard level.

In a further aspect there is provided a method for assessing the efficacy of an agent for reducing clinical risk in an individual exposed to an influenza virus, the method comprising administering said agent to said individual, determining the level of an IFI27 gene product in a biological sample from said individual- and comparing said determined level to a standard level.

In an embodiment the individual is exposed to an influenza virus prior to administration of said agent. In an embodiment the individual has an influenza infection when administered said agent. In an embodiment the individual is exposed to an influenza virus after said administration of said agent.

In an embodiment the standard level indicative of clinical risk comprises a standard curve defining clinical risk. In an embodiment, the methods of the invention comprise the use of a standard curve encompassing a range of amounts of IFI27, such as a range from negligible clinical risk to clinical risk of severe disease.

In an embodiment the standard level is prepared by subjecting one or more known sample(s) of an IFI27 gene product to the same methods for determining IFI27 gene expression level as the biological sample from said individual, wherein the one or more known sample(s) of an IFI27 gene product are of a pre-determined amount or amounts indicative of clinical risk.

In an embodiment the method further comprises determining the level of IFI27 gene product in a biological sample obtained from said individual prior to administration of said agent. In an embodiment a decrease in the level of an IFI27 gene product in a biological sample from said individual after administration of said agent compared to the level prior to said administration is indicative of an agent capable of reducing disease severity in a patient exposed to an influenza virus or having an influenza infection.

In an embodiment the method is conducted as part of a research trail or clinical trial of a candidate anti-viral agent for the prevention or treatment of influenza.

ABBREVIATIONS

The abbreviation RSV is used herein for respiratory syncytial virus.

The abbreviation IFI27 is used herein for interferon alpha inducible protein 27. The abbreviation p27 may also be used herein for interferon alpha inducible protein 27.

The abbreviation GAPDH is used herein for glyceraldehyde phosphate dehydrogenase.

The abbreviation LPS is used herein for lipopolysaccharide.

DEFINITIONS

As used in this application, the singular form "a", "an" and "the" include plural references unless the context clearly dictates otherwise.

Unless the context requires otherwise or it is specifically stated to the contrary, integers, steps, or elements of the invention recited herein as singular integers; steps or elements clearly encompass both singular and plural forms of the recited integers, steps or elements.

The term "at least one" when used in the context of a group of selectable elements includes any and all members of the group individually selected and includes any combination of the members of the group. Similarly, the term "at least two" when used in the context of a group of selectable elements includes any selection of two or more members of the group in any combination.

As used herein, the term "comprising" means "including." Variations of the word "comprising", such as "comprise" and "comprises," have correspondingly varied meanings. Thus, for example, a polynucleotide "comprising" a sequence encoding a protein may consist exclusively of that sequence or may include one or more additional sequences. Similarly a method "comprising" one or more stated activities may consist exclusively of those activities or may include one or more additional activities. Similarly a kit "comprising" one or more stated components may consist exclusively of those components or may include one or more additional components.

As used herein, the terms "antibody" and "antibodies" are used in their broadest meaning and include IgG (including IgG1, IgG2, IgG3, and IgG4), IgA (including IgA1 and IgA2), IgD, IgE, or IgM, and IgY, whole antibodies, including single-chain whole antibodies, and antigen-binding fragments thereof. Antigen-binding antibody fragments include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin. Antigen-binding antibody fragments, including single-chain antibodies, may comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies may be monoclonal, polyclonal, chimeric, multispecific, humanized, and human monoclonal and polyclonal antibodies that specifically bind the biological molecule.

As used herein, the terms "polypeptide" and "protein" are used interchangeably and are taken to have the same meaning.

As used herein, the terms "nucleotide sequence" and "polynucleotide sequence" and "nucleic acid sequence" are used interchangeably and are taken to have the same meaning.

As used herein, the term "kit" refers to any delivery system for delivering materials. In the context of the detection assays and methods described herein, such delivery systems include systems that allow for the storage, transport, or delivery of reaction reagents (for example labels, reference samples, supporting material, etc. in the appropriate containers) and/or supporting materials (for example, buffers, written instructions for performing the assay, etc.) from one location to another. For example, kits include one or more enclosures, such as boxes, containing the relevant reaction reagents and/or supporting materials.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention before the priority date of this application.

For the purposes of description all documents referred to herein are incorporated by reference in their entirety unless otherwise stated.

BRIEF DESCRIPTION OF THE DRAWINGS

A preferred embodiment of the present invention will now be described, by way of an example only, with reference to the accompanying drawings wherein:

FIG. 22 shows the nucleotide sequence of IFI27 mRNA sequence, isoform 1 (SEQ ID NO:1). *Homo sapiens* interferon, alpha-inducible protein 27 (IFI27), mRNA. NCBI Reference Sequence: NM_001130080.1. Sites of primer annealing (SEQ ID NO.: 7 and SEQ ID NO.:8) are highlighted and underlined.

FIG. 23 shows the nucleotide sequence of IFI27 mRNA sequence, isoform 2 (SEQ ID NO:2). Sites of primer annealing (SEQ ID NO.: 7 and SEQ ID NO.:8) are highlighted and underlined.

FIG. 24 shows the amino acid sequence of IFI27, isoform 1 (SEQ ID NO:3). Interferon alpha-inducible protein 27, [*Homo sapiens*]. NCBI Reference Sequence: NP_001123552.1

FIG. 25 shows the amino acid sequence of IFI27, isoform 2 (SEQ ID NO:4).

FIG. 26 shows the target region of IFI27 (SEQ ID NO:11) in the examples herein. Nucleotide sequence positions by reference to uc021sba.1_IFI27. Sites of primer annealing (SEQ ID NO.: 7 and SEQ ID NO.:8) are highlighted and underlined.

FIG. 27 shows the target region of GAPDH in the examples herein. Nucleotide sequence amplified by reference to uc001qop.1_GAPDH (SEQ ID NO.:13). Exons are indicated in uppercase font. Sites of primer annealing (SEQ ID NO.: 14 and SEQ ID NO.: 15) are highlighted and underlined.

FIG. 28 shows the nucleotide sequence of *Homo sapiens* glyceraldehyde-3-phosphate dehydrogenase (GAPDH), transcript variant 1, mRNA. NCBI Reference Sequence: NM_002046.4 (SEQ ID NO.: 12). Sites of primer annealing (SEQ ID NO.: 14 and SEQ ID NO.:15) are highlighted and underlined.

FIG. 29 shows the nucleotide sequence of *Homo sapiens* glyceraldehyde-3-phosphate dehydrogenase (GAPDH), transcript variant 2, mRNA. NCBI Reference Sequence: NM_001256799.1 (SEQ ID NO.:18). Sites of primer annealing (SEQ ID NO.: 14 and SEQ ID NO.:15) are highlighted and underlined.

SEQUENCES REFERRED TO HEREIN

Figure 1:
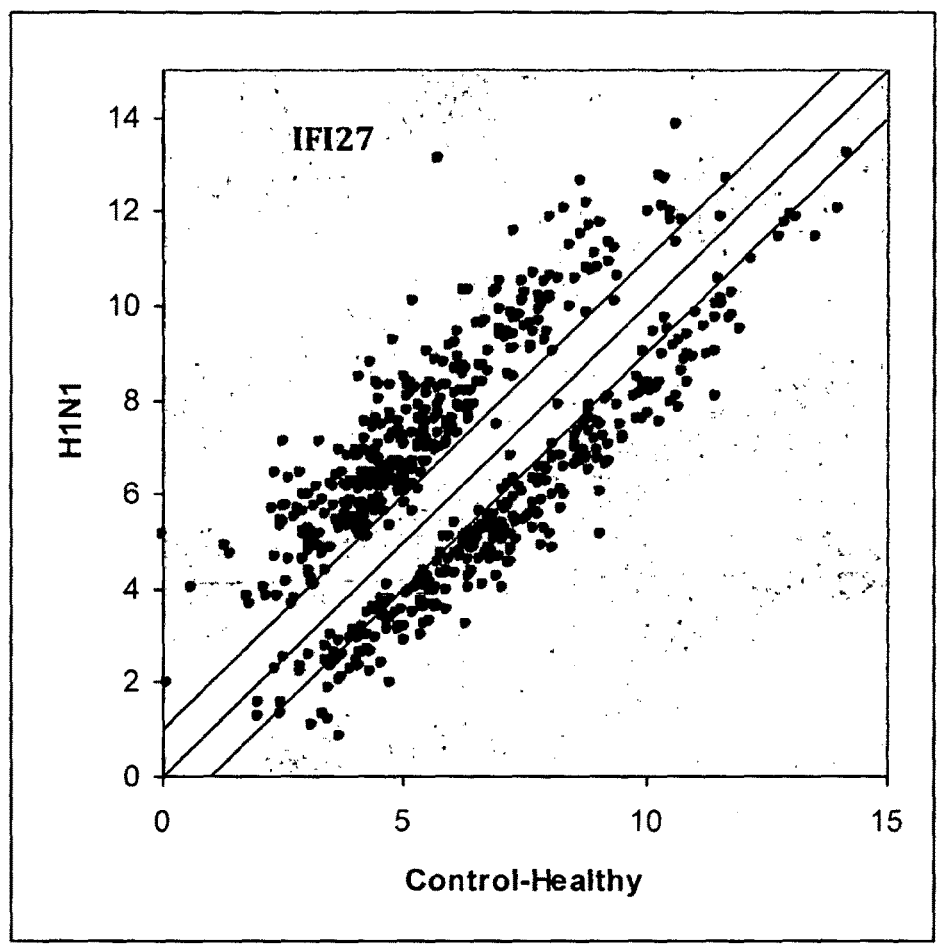
FIG. 1 shows a screen of candidate genes using genome-wide microarray analysis. Peripheral blood was sampled from individuals with confirmed influenza infection. RNA was extracted for microarray analysis covering 48,804 probes (Illumina Sentrix HT-12_v3_BeadChip arrays). Gene expression signals were represented by log 2 of expression intensity on each axis. Diagonal line represents no change in expression when two groups were compared (H1N1 influenza vs. healthy controls). Line above the diagonal line represents at least two fold increases in gene upregulation. Line below the diagonal line represents at least two fold increases in gene down-regulation. Each dot denotes individual probe on the microarray. IFI27 denotes alpha-inducible protein 27.

SEQ ID NO:1: IFI27 mRNA sequence, isoform 1; 665 base; from NM_001130080.1.

SEQ ID NO:2: IFI27 mRNA sequence, isoform 2, 656 base.

SEQ ID NO:3: IFI27 polypeptide amino acid sequence, isoform 1; from NP_001123552.1

SEQ ID NO:4: IFI27 polypeptide amino acid sequence, isoform 2.

SEQ ID NO:5: IFI27 cDNA sequence, isoform 1; as would be synthesized from isoform 1 mRNA (SEQ ID NO: 1) from NM_001130080.1.

SEQ ID NO:6: IFI27 cDNA sequence, as would be synthesized from isoform 2 mRNA (SEQ ID NO:2).

SEQ ID NO:7: acctcatcagcagtgaccagt (IFI27 forward primer 59.8C).

SEQ ID NO:8: acatcatcttggctgctatgg (IFI27 reverse primer 60.1C).

SEQ ID NO:9: TGCCTCGGGCAGCCT (IFI27 forward primer).

SEQ ID NO:10: TTGGTCAATCCGGAGAGTCC (IFI27 reverse primer).

SEQ ID NO:11: IFI27 target nucleic acid sequence as per the examples herein. Sequence and coordinates from UCSC Genes, uc021sba.1_IFI27, positions 142-328. 187 bp target region.

SEQ ID NO:12: GAPDH full length mRNA sequence; transcript variant 1, mRNA; NCBI Reference Sequence: NM_002046.4.

SEQ ID NO:18: GAPDH full length mRNA sequence; transcript variant 2, mRNA; NCBI Reference Sequence: NM_001256799.1

SEQ ID NO:13: GAPDH target nucleic acid sequence as per the examples herein. Sequence and coordinates from UCSC Genes, uc001qop.1_GAPDH.

SEQ ID NO:14: ACGCATTTGGTCGTATTGGG (GAPDH forward primer).

SEQ ID NO:15' TGATTTTGGAGGGATCTCGC (GAPDH reverse primer).

SEQ ID NO:16: cag gaa ttc atA TGG AGG CCT CTG CTC TCA (IFI27 forward primer from Gjermandsen et al, 1999 (ISG12f)).

SEQ ID NO:17: cgc gaa ttc agC TAG TAG AAC CTC GCA ATG (IFI27 reverse primer from Gjermandsen et al, 1999 (ISG12r)).

DETAILED DESCRIPTION

The present invention is based, at least in part, on the identification by the inventors that the expression level of IFI27 in a subject correlates with the severity of disease caused by influenza infection in that subject. The invention may be used to assess' patients infected with influenza by determining which individuals have a clinical risk, as defined by being more likely to develop serious disease and require medical intervention in a hospital or clinical environment. This determination may be made prior to a patient being symptomatic of an influenza infection, and prior to a patient showing symptoms indicative of a severe disease. The medical intervention may include, but is not limited to, hospital admission or life-support therapy. The invention has applications in healthcare, for example in the early management of influenza infection, in monitoring a patient's immune response to the disease, and in enabling life-saving intervention to at-risk individuals who may otherwise be missed by traditional diagnostic approaches.

In one aspect of the invention there is provided a method for identifying clinical risk in a patient having or suspected of having an influenza infection, the method comprising determining the expression level of interferon alpha inducible protein 27 (IFI27) gene in a biological sample from said patient and comparing the determined level of IFI27 gene product to a standard level. The standard level of IFI27 gene product may be one that is indicative of clinical risk, or no clinical risk.

When comparing the level of IFI27 gene products in patients with those of standard levels, an elevated level of IFI27 gene product in a patient may be expressed as a fold increase over the standard level. In one aspect of the present invention, a level of IF 27 gene product in a patient that is at least 40 to 60 times the level of IFI27 gene product typical of healthy subjects or subject with influenza that are asymptomatic is indicative of clinical risk. In another aspect of the invention, a level of IFI27 gene product in a patient that is at least 40 times the level of IFI27 gene product typical of healthy subjects or subject with influenza that are asymptomatic is indicative of clinical risk. In a further aspect, a level of IFI27 gene product in a patient that is at least 50 times the level of IFI27 gene product typical of healthy subjects or subject with influenza that are asymptomatic is indicative of clinical risk. In yet another aspect of the present invention, a level of IFI27 gene product in a patient that is at least 60 times the level of IFI27 gene product typical of healthy subjects or subject with influenza that are asymptomatic is indicative of clinical risk.

In another aspect of the invention there is provided use of an agent capable of detecting an IFI27 gene product in a biological sample for the manufacture of a diagnostic for identifying clinical risk in a patient having or suspected of having an influenza infection.

In another aspect of the invention there is provided an agent capable of detecting an IFI27 gene product in a biological sample for use in a method of identifying clinical risk in a patient having or suspected of having an influenza infection.

It will be understood that determining the level of IFI27 gene product, for example in a biological sample, may alternatively be referred to herein as determining the expression level of IFI27 gene, for example in a biological sample. Hence, determining the expression level of IFI27 gene product is meant in its broadest sense, such that the "level" may include any IFI27 transcript or downstream product, such as IFI27 protein or fragment thereof.

The interferon alpha induced protein 27 (IFI27) gene product may be any appropriate gene product, including, but not limited to, nucleic acids, for example RNA transcripts, cDNA derivatives of such transcripts, and the like, proteins and polypeptides. Typically the gene product is an mRNA or fragment thereof or a polypeptide, protein or fragment thereof.

The present invention addresses a lack of risk stratification tools in infectious disease medicine which compounds the morbidity, mortality and social and financial cost of an infectious disease, especially during an epidemic (e.g. annual seasonal influenza) or a pandemic (e.g. H1N1 2009 influenza virus), because the capacity to effectively manage factors which mitigate against spread and severity of the disease is diminished or unavailable. Such mitigating factors include determination and prioritization of (1) patients requiring quarantine, to control against disease spread; (2) patients' susceptibility to deterioration, to reduce severity of disease and length of infection; and (3) patients' pre-disposal to co-morbidity, to neutralize high-risk or difficult cases early.

Risk stratification by an IFI27 biomarker as described herein may minimize delays for hospital admission and hence potentially save lives. By providing a risk stratification tool for influenza infection that can be employed prior to patients becoming symptomatic of an infection or of severe disease, high risk patients can be identified early ensuring prompt delivery of appropriate medical care to these patients.

The methods of the invention also permit a clinician to monitor the progress of a patient having influenza. This allows the clinician to monitor a patient for possible deterioration from a relatively mild manifestation of disease to clinical risk, or to monitor the improvement of a patient from a state of clinical risk to recovery.

Typically this type of monitoring would be done, in the methods of the invention, by determining the level of IFI27 gene product in a first biological sample from the patient and determining the level of IFI27 gene product in a second biological sample from the patient, where the first and second samples have been obtained from the patient at different times. For example, the first may have been obtained prior to treatment being commenced, and the second may have been obtained after a given period of time during which the patient was undergoing treatment or observation.

Any number of subsequent samples may of course be used in order to further monitor the patient, as may be desirable. Samples may be obtained from the patient at appropriate intervals, such as intervals of one or several hours, or daily or weekly. Samples may be obtained after a certain treatment has been undertaken, such as the administration of a therapeutic agent to treat the disease cause by the influenza infection.

In this manner an increase in the level of IFI27 gene product in the second (or subsequent) biological sample compared to said first biological sample is indicative of an increased clinical risk in said patient, whereas a decrease is indicative of a reduced clinical risk. An increased clinical risk may be defined as an increased likelihood that the patient will need or continue to need medical intervention, while a decreased clinical risk is a decreased likelihood that the patient will need or continue to need medical intervention. Depending on the results of such monitoring, the clinician may adjust the treatment of the patient. The method thus assists clinicians in the treatment and management of patients.

The inventors have also demonstrated through in vitro testing that the elevated expression of IFI27 is specific to influenza infection and is not increased in bacterial infection. As a result the invention also provides methods to distinguish patients having influenza and related conditions, such as viral pneumonia, from patients having other conditions, Which may present with similar symptoms, such as bacterial pneumonia. This ability is advantageous for the treating clinician in a number of circumstances, and can assist in avoiding the over-management of patients that may have symptoms that could be indicative of both influenza and bacterial infections. Consequently, the present invention may alleviate one or more issues typical of influenza infection management, particularly at general practice level, such as the "over-treatment" of influenza patients with antibiotics on precautionary rather than stratified diagnosis. So extensive is this practice that antibiotic resistant bacteria are emerging. The present invention may alleviate situations of gross under-management or over-management of the disease, respectively leading to either large-scale unnecessary morbidity, often compounded to produce mortality, or to over-prescription of antibiotics, encouraging development of resistant bacterium.

In another scenario, a patient may be admitted to hospital first with viral pneumonia. The patient may subsequently develop a complication, such as bacterial pneumonia. The clinicians need to know whether the patient is not getting better because (1) the viral pneumonia persists, or (2) a bacterial infection has superimposed. The present invention provides the capability of distinguishing between the two on the basis of expression of IFI27 gene product, which will be elevated in the patient, as determined by analysis of a biological sample from the patient, if the viral pneumonia persists and or clinically significant influenza persists but will be at or near basal levels if the patient has bacterial pneumonia instead.

A further scenario is that the patient first presents to an emergency department with atypical or unusual symptoms such that the physician cannot diagnose with confidence whether it is bacterial or viral pneumonia in the first instance. This is a more common clinical dilemma and so far, traditional tests have not been helpful in resolving this issue. As a precautionary measure, such patients would often be treated with antibiotics. By providing the capability of distinguishing between a patient having viral pneumonia, in which it is expected that IFI27 expression determined in a biological sample from the patient will be elevated, from a patient having only bacterial pneumonia in which it is expected that IFI27 expression levels will not be elevated, the present invention offers the physician an improved diagnostic tool thereby allowing clinically relevant treatment to be commenced at an earlier time.

In another aspect, the invention thus provides a method for identifying influenza or viral pneumonia in a patient, the method comprising determining the expression level of IFI27 gene in a biological sample from said patient and comparing the determined level of IFI27 gene product to a standard level. The standard level may be based the level of IFI27 gene products in healthy patients, or patients that have a bacterial pneumonia, wherein an elevated level of IFI27 gene product in said patient is indicative of a patient with influenza or viral pneumonia.

In one aspect of the present invention, a level of IFI27 gene product in a biological sample from a patient that is at least 10 times higher than the standard level is indicative of influenza or viral pneumonia.

In another aspect of the invention there is provided use of an agent capable of detecting an IFI27 gene product in a biological sample for the manufacture of a diagnostic for identifying influenza or viral pneumonia in a patient, In another aspect of the invention there is provided an agent capable of detecting an IFI27 gene product in a biological sample for use in a method of identifying influenza or viral pneumonia in a patient.

In another aspect of the invention there is provided a kit for use in a method of identifying influenza or viral pneumonia in a patient, the kit comprising at least one agent capable of detecting an IFI27 gene product in a biological sample.

The identification by the inventors that IFI27 expression correlates with the severity of disease cause by influenza infection also has benefits in testing of, and for, agents that may be useful in the treatment or prevention of influenza. This may be, for example, agents capable of reducing disease severity in subjects exposed to an influenza virus. Anti-viral (influenza virus) is a major area of research and clinical trials are conducted to investigate the efficacy of potential or putative anti-viral medication or agents. Typically, these trials use clinical parameters such as heart rate, oxygen level in the blood, blood pressure, death rate (mortality), etc. There are significant limitations with these parameters. This is because they are not measuring disease severity (e.g. heart rate and blood pressure are non-specific for infection severity). In addition, events such as death are a rare event in influenza infection. This means the clinical trial needs to recruit thousands of patients in order to have adequate statistical power to detect a difference between treatment and control groups. An alternative to overcome or ameliorate limitations in clinical trials is to use a surrogate marker. Ideally, a surrogate marker reflects the biological activity of the disease and correlates with treatment effect (i.e. its level decreases with the success of the treatment). As demonstrated herein, IFI27 has the potential to be such a surrogate marker. It can help monitor treatment response during clinical trials of anti-viral drugs.

Interferon Alpha Induced Protein 27 (IFI27)

IFI27 is one member of a family of small interferon alpha inducible genes of unknown function. IFI27 is alternatively known as interferon alpha-induced 11.5 kDa protein, interferon-stimulated gene 12a protein and by the alternative abbreviations ISG12, ISG12(a), FAM14D, and P27. The cDNA for IFI27 was originally cloned as an estrogen-inducible gene in the human epithelial cell line MCF-7 and designated p27[3]. IFI27 has been reported to be upregulated in lesional and non-lesional psoriatic skin[4] in lesional psoriatic epidermis as well as being detectable in non-lesional keratinocytes in a quantitative RT-PCR study[5]. The same study also reported expression in other skin conditions, such as lichen planus, chronic eczema, cutaneous squamous cell cancers and showed upregulated expression when keratinocytes were stimulated with IFN-γ, TNF-α or TGF-β1. As a result, it has been postulated that IFI27 is a marker of epithelial proliferation and cancer. IFI27 has also been reported as being significantly over-expressed in systemic lupus erythematosus synovial tissue as compared with osteoarthritis and rheumatoid arthritis synovial tissue[6].

The instant application provides the first description of a correlation between an increased expression level of IFI27 and clinical risk in subjects having influenza.

The human IFI27 gene is 11,852 bp in length, located at 14q32. There are reports of splice variants giving rise to different protein isoforms7. There are two known transcript variants of IFI27, referred to as isoform 1 (665 nucleotides) and isoform 2 (656 nucleotides). NM_001130080.1 is the NCBI Reference Sequence for isoform 1. This variant represents an allele commonly found in the human population. The complete polypeptide sequence is 119 amino acids. NM_005532.3 is the NCBI Reference Sequence for isoform 2. This variant (2) represents an alternate allele that lacks a 9-nt segment in the CDS, as compared to variant 1. The resulting isoform (2) lacks an internal 3 amino acid segment and differs at two adjacent amino acid, as compared to isoform 1. This variant represents a second allele commonly found in the human population. The IFI27 polypeptide is alternately known as interferon alpha-induced 11.5 kDa protein.

Expression of IFI27 has been investigated in various reports, primarily utilizing investigation at the nucleotide level, for example by RT-PCRs[5,6,8], and by Northern analysis[5]. Expression of IFI27 gene product has also been reported on the basis of detection and or quantitative analysis of the level of IFI27 polypeptide, for example utilizing immunoassay or western blotting[6]. Methods for the detection and or determination of expression of IFI27 gene product described in prior publications are appropriate for the working of the methods of the present invention and the methods and agents described therein are incorporated herein by reference.

Patients

Methods of the invention comprise analysis of a patient sample for the presence and quantification of an IFI27 gene product. In this manner the level of IFI27 gene product in the sample may be determined, thereby allowing identification of clinical risk in a patient. Similarly, the methods of the invention permit an assessment of a patient for the presence of influenza or viral pneumonia as distinct from conditions, which may have similar clinical presentation, such as bacterial pneumonia.

It will be understood that the use herein of the term "patient" is intended to have broad meaning. The patient is any individual in respect of which the method is performed. Typically, the patient is an individual having or suspected of having an influenza infection. By way of non-limiting example, the patient may be a hospitalised individual, an individual who presents at a hospital outpatient or emergency department, an individual who presents at a doctor's clinic or surgery or medical practice or at any health assessment or health testing facility. The patient may be an individual who is a member of a population presenting with or without one or more symptoms of influenza infection. The patient may be a member of a group or population considered to be "at-risk" of potentially developing severe disease due to influenza infection, for example, the elderly, the chronically ill, the immune compromised, those with a history of severe disease from influenza virus, those with a history of flu-like symptoms. Members of such groups or populations may be subject to screening as part of a broad health objective, such as during an influenza outbreak, pandemic or epidemic.

Biological Sample

In embodiments the method of the invention comprises obtaining a biological sample from the patient. The biological sample is typically a blood sample. The biological sample may be a selected component of blood, such as blood cell subsets, a protein fraction or a nucleic acid fraction, such as total RNA or mRNA. The biological sample may be processed to fractionate or enrich it for the presence of one or more components, such as white blood cells, or a specific component thereof such as pDCs.

The step of obtaining a biological sample, such as a blood sample, from a patient may be undertaken as part of a consecutive series of steps in the performance of the method of the invention. The step of obtaining a blood sample from a patient may be undertaken as a distinct step or steps separate from one or more remaining steps of the method of the invention, for example separate in time, location or operator. Accordingly, in the performance of the method of the invention obtaining the blood sample may or may not involve extraction of blood from said patient. Performance of the method of the invention may, for example, comprise receiving a blood sample in a container, the blood having previously been extracted from the patient as an exercise separate from the performance of the method of the invention. As a further example, obtaining a blood sample may comprise retrieving from temporary storage a blood sample extracted from the patient as an exercise separate from the performance of the method of the invention. It will be understood that the performance of the method of the invention may thus be conducted entirely ex vivo.

A biological sample obtained from a patient may undergo one or more transformation steps either as part of the working of the invention or as a separate step or series of steps. For example, where a blood sample is obtained from a patient, the sample may be further processed to produce a more convenient form of biological sample that is used in methods of the invention. This may be, for example, processing of the blood to isolate different cell subsets, which is used in the assessment of IFI27 gene product. Alternatively, or in addition it may simply be the processing of the blood to remove components that might interfere with the efficient operation of the methods, such as red blood cells, or anticoagulant, which may have been used in the collection of the sample.

As a further alternative or additive step or steps, the sample may be processed to create a fraction that is used in the determination of IFI27 gene product and a fraction or fractions that is not. This processing or fractionation may include, for example, the isolation of total RNA from the sample, or the isolation of messenger RNA (mRNA) from the sample, or the isolation of protein or polypeptides from the sample, any of which may be suitable for use in determining IFI27 gene product. The skilled addressee will be aware that methods exist for the processing of blood samples in this manner, for example RNEASY mini kit, Qiagen and FOCUS membrane protein kit, GBiosciences protocols).

Polynucleotides and Polypeptides

The inventors have identified that the level of expression of IFI27 gene in subjects having influenza correlates with disease severity, and therefore can be utilized as an indicator of clinical risk. Accordingly, in the working of the invention, a sample may be tested for the presence of an IFI27 gene product. The gene product may be an IFI27 mRNA or transcript. The full polynucleotide sequence of the IFI27 mRNA has been determined and is reported, for example at Ensembl/Havana merge: ENSG00000165949. As noted herein there are variants of the IFI27 transcript previously described. In an embodiment analyzing the sample for the presence of an IFI27 gene comprises analyzing the sample for the presence of an IFI27 mRNA sequence, such as a sequence shown in SEQ ID NO:1 or SEQ ID NO:2, or a fragment or variant thereof.

The gene product may be the IFI27 polypeptide, ISG12, and two isoforms of the ISG12 polypeptide have been reported and the sequences determined, for example, NP_001123552.1. In an embodiment analyzing the sample for the presence of an IFI27 gene product comprises analyzing the sample for the presence of an IFI27 polypeptide, such as those shown in SEQ ID NO:3 or SEQ ID NO:4, or a fragments or variants thereof In addition to the polynucleotides and polypeptide sequences set forth herein, also included within the scope of the present invention and the methods of the invention are variants and fragments thereof. Hence, where it is stated that a sample may be tested for the presence of a given polynucleotide sequence it will be understood that the statement also means that the sample may be tested for the presence of a fragment or variant of that polynucleotide sequence.

As used in the methods of the invention the polynucleotides disclosed herein may be deoxyribonucleic acids (DNA), ribonucleic acids (RNA) or complementary deoxyribonucleic acids (cDNA).

RNA may be derived from RNA polymerase-catalyzed transcription of a DNA sequence. The RNA may be a primary transcript derived from transcription of a corresponding DNA sequence. RNA may also undergo post-transcriptional processing. For example, a primary RNA transcript may undergo post-transcriptional processing to form a mature RNA. As described herein it is known that there are at least two isoforms of IFI27 transcript, one of 665 nucleotides and one of 656 nucleotides (see SEQ ID NO: 1 and 2, respectively). Messenger RNA (mRNA) refers to RNA derived from a corresponding open reading frame that may be translated into protein by the cell. cDNA refers to a single-stranded DNA that is complementary to and derived from mRNA. cDNA corresponding to the isoform 1 and isoform 2 IFI27 sequences referred to herein as SEQ ID NO:5 and 6, respectively. Sense RNA refers to RNA transcript that includes the mRNA and so can be translated into protein by the cell. Antisense RNA refers to an RNA transcript that is complementary to all or part of a target primary transcript or mRNA and may be used to block the expression of a target gene.

The skilled addressee will recognise that RNA and cDNA sequences encoded by the DNA sequences disclosed herein may be derived using the genetic code. An RNA sequence may be derived from a given DNA sequence by generating a sequence that is complementary the particular DNA sequence. The complementary sequence may be generated by converting each cytosine ('C') base in the DNA sequence to a guanine ('G') base, each guanine ('G') base in the DNA sequence to a cytosine ('C') base, each thymidine ('T') base in the DNA sequence to an adenine ('A') base, and each adenine ('A') base in the DNA sequence to a uracil ('U') base.

A complementary DNA (cDNA) sequence may be derived from a DNA sequence by deriving an RNA sequence from the DNA sequence as above, then converting the RNA sequence into a cDNA sequence. An RNA sequence can be converted into a cDNA sequence by converting each cytosine ('C') base in the RNA sequence to a guanine ('G') base, each guanine ('G') base in the RNA sequence to a cytosine ('C') base, each uracil ('U') base in the RNA sequence to an adenine ('A') base, and each adeneine ('A') base in the RNA sequence to a thymidine ('T') base.

In general, polypeptide sequence variants possess qualitative biological activity in common. Polynucleotide sequence variants generally encode polypeptides, which generally possess qualitative biological activity in common. Accordingly, the inventors envisage that variation in the specific sequence of IFI27 is likely to exist in nature, without causing significant alteration in the biological activity of the encoded gene, by comparison to the sequences provided herein. As a result, the present invention is not limited to the IFI27 sequence as specifically stated herein but is also applicable to variant sequences of IFI27 as may exist in nature. Such sequences herein would be expected to retain the characteristic expression of gene product demonstrated herein and thus are equally applicable as indicative markers of clinical risk in a patient or subject having or suspected of having an influenza infection.

As a consequence, variant sequences of those explicitly stated herein are also included within the invention. The term "variant" as used herein refers to a substantially similar sequence. In general, two sequences are "substantially similar" if the two sequences have a specified percentage of amino acid residues or nucleotides that are the same (percentage of "sequence identity"), over a specified region, or, when not specified, over the entire sequence. Accordingly, a "variant" of a polynucleotide and polypeptide sequence disclosed herein may share at least 40%, 45%, 50%, 55%, 60%, 65%, 70%, 75%, 80%, 83% 85%, 88%, 90%, 93%, 95%, 96%, 97%, 98% or 99% sequence identity with the reference sequence.

Further, the term "variant" also includes analogues of the polypeptides of the invention. A polypeptide "analogue" is a polypeptide, which is a derivative of a polypeptide of the invention, which derivative comprises addition, deletion, substitution of one or more amino acids, such that the polypeptide retains substantially the same function. The term "conservative amino acid substitution" refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution.

In general, the percentage of sequence identity between two sequences may be determined by comparing two optimally aligned sequences over a comparison window. The portion of the sequence in the comparison window may, for example, comprise deletions or additions (i.e. gaps) in comparison to the reference sequence (for example, a polynucleotide or polypeptide sequence disclosed herein), which does not comprise deletions or additions, in order to align the two sequences optimally. A percentage of sequence identity may then be calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

In the context of two or more nucleic acid or polypeptide sequences, the percentage of sequence identity refers to the specified percentage of amino acid residues or nucleotides that are the same over a specified region, (or, when not specified, over the entire sequence), when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be determined conventionally using known computer programs, including, but not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA).

The BESTFIT program (Wisconsin Sequence Analysis Package, for Unix, Genetics Computer Group, University Research Park, 575 Science Drive, Madison. Wis. 53711) uses the local homology algorithm of Smith and Waterman to find the best segment of homology between two sequences (Smith and Waterman, Advances in Applied Mathematics 2:482-489 (1981)). When using BESTFIT or any other sequence alignment program to determine the degree of homology between sequences, the parameters may be set such that the percentage of identity is calculated over the full length of the reference nucleotide sequence and that gaps in homology of up to 5% of the total number of nucleotides in the reference sequence are allowed.

GAP uses the algorithm described in Needleman and Wunsch (1970) J. Mol. Biol. 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP presents one member of the family of best alignments.

Another method for determining the best overall match between a query sequence and a subject sequence, also referred to as a global sequence alignment, can be determined using the FASTDB computer program based on the algorithm of Brutlag and colleagues (Comp. App. Biosci. 6:237-245 (1990)). In a sequence alignment the query and subject sequences are both DNA sequences. An RNA sequence can be compared by converting U's to T's. The result of said global sequence alignment is in percent identity.

The BLAST and BLAST 2.0 algorithms may be used for determining percent sequence identity and sequence similarity. These are described in Altschul et al. (1977) Nuc. Acids Res. 25:3389-3402, and Altschul et al (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl, Acad. Sci USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Also contemplated are fragments of the polynucleotides disclosed herein. A polynucleotide "fragment" is a polynucleotide molecule that encodes a constituent or is a constituent of a polynucleotide of the invention or variant thereof. Fragments of a polynucleotide do not necessarily need to encode polypeptides which retain biological activity. The fragment may, for example, be useful as a hybridization probe or PCR primer. The fragment may be derived from a polynucleotide of the invention or alternatively may be synthesized by some other means, for example by chemical synthesis. The fragment may, for example, be that which is detected in the determination of the level of IFI27 gene product in a biological sample, such that, for example, the probe or primer(s) are specific to a region of the IFI27 gene product and it is that region that is detected in the working of the invention. This is typical, for example, in methods where PCR is used such that the target region of the IFI27 gene product, typically mRNA or cDNA, will constitute less than the complete IFI27 mRNA or cDNA sequence length. For example, it may be a target region of about 50 to 100 bases or base pairs, or about 75 to 150 bases or base pairs, or about 120 to 250 bases or base pairs, or about 200 to 300 bases or base pairs, or about 250 to 350 bases or base pairs, or about 300 to 400 bases or base pairs, or about 350 to 450 bases or base pairs, or about 400 to 500 bases or base pairs.

The sequences of the invention may comprise discrete sequences in which the entire sequence comprises only the sequence, or a fragment thereof, of the IFI27 gene identified herein. The sequences of the invention may instead be non-discrete sequences, in that they comprise the sequence, or part thereof, of the IFI27 gene identified herein or a variant thereof together with sequence, which is not part of that gene. In a similar fashion, the sequences may also include unrelated sequence, such as sequence associated with vectors, tags, such as for assisting purification or detection, and hybridisation aids.

A polynucleotide may be cloned into a vector. The vector may comprise, for example, a DNA, RNA or complementary DNA (cDNA) sequence. The vector may be a plasmid vector, a viral vector, or any other suitable vehicle adapted for the insertion of foreign sequences, their introduction into cells and the expression of the introduced sequences. Typically the vector is an expression vector and may include expression control and processing sequences such as a promoter, an enhancer, ribosome binding sites, polyadenylation signals and transcription termination sequences. The invention also contemplates host cells transformed by such vectors. For example, the polynucleotides of the invention may be cloned into a vector, which is transformed into a bacterial host cell, for example *E. coli*. Methods for the construction of vectors and their transformation into host cells are generally known in the art, and described in, for example, *Molecular Cloning: A Laboratory Manual*. 4th ed., Green and Sambrook, 2012, Cold Spring Harbor Laboratory Press, Plainview, N.Y., and, Ausubel F. M. et al. (Eds) *Current Protocols in Molecular Biology*, John Wiley and Sons, Inc.

Nucleotide Probes, Primers and Antibodies

The present invention is based, at least in part, on the identification by the inventors that the expression level of interferon alpha induced protein 27 (IFI27) gene in a subject correlates with the severity of influenza in that subject. The invention thus relates to methods for the detection of host response during influenza infection through the detection and determination of the level of expression of an interferon alpha induced protein 27 (IFI27) gene in a sample obtained from a subject of interest. In the working of the method nucleotides and fragments based on the sequence of the IFI27 polynucleotide, or fragments or variants thereof, may be used as primers and probes for the detection and determination of the level of an interferon alpha induced protein 27 (IFI27) gene product.

The nucleotides and fragments may be in the form of oligonucleotides. Oligonucleotides are short stretches of nucleotide residues suitable for use in nucleic acid amplification reactions such as PCR, typically being at least about 5 nucleotides to about 80 nucleotides in length, more typically about 10 nucleotides in length to about 50 nucleotides in length, and even more typically about 15 nucleotides in length to about 30 nucleotides in length. The skilled addressee will understand that any appropriate length of sequence may be used such as 10, 11, 12, 13, 14, 15, 16, 17, 18, 19, 20, 21, 22, 23, 24, 25, 26, 27, 28, 29, or 30 nucleotides or more.

Probes are nucleotide sequences of variable length, for example between about 10 nucleotides and several thousand nucleotides, for use in detection of homologous sequences, typically by hybridization. For example, a probe for use in hybridization may be about 10 to 25 bases or base pairs, or about 20 to 40 bases or base pairs, or about 30 to 50 bases or base pairs, or about 50 to 100 bases or base pairs, or about 75 to 150 bases or base pairs, or about 120 to 250 bases or base pairs, or about 200 to 300 bases or base pairs, or about 250 to 350 bases or base pairs, or about 300 to 400 bases or base pairs, or about 350 to 450 bases or base pairs, or about 400 to 500 bases or base pairs. Hybridization probes may be genomic DNA fragments, cDNA fragments, RNA fragments, or other oligonucleotides.

Methods for the design and/or production of nucleotide probes and/or primers are generally known in the art, and are described in *Molecular Cloning: A Laboratory Manual*, 4th ed., Green and Sambrook, 2012; Itakura K. et al. (1984) *Annu. Rev. Biochem.* 53:323; Innis et al., (Eds) (1990) *PCR Protocols: A Guide to Methods and Applications* (Academic Press, New York); Innis and Gelfand, (Eds) (1995) *PCR Strategies* (Academic Press, New York); and Innis and Gelfand, (Eds) (1999) *PCR Methods Manual* (Academic Press, New York). Nucleotide primers and probes may be prepared, for example, by chemical synthesis techniques for example, the phosphodiester and phosphotriester methods (see for example Narang S. A. et al. (1979) Meth. Enzymol. 68:90; Brown, E. L. (1979) et al. Meth. Enzymol. 68:109; and U.S. Pat. No. 4,356,270), the diethylphosphoraniidite method (see Beaucage S. L et al. (1981) Tetrahedron Letters, 22:1859-1862). A method for synthesizing oligonucleotides on a modified solid support is described in U.S. Pat. No. 4,458,066.

The nucleic acids of the invention, including those mentioned herein, may be labelled by incorporation of a marker to facilitate their detection. Techniques for labelling and detecting nucleic acids are described, for example, in Ausubel F. M. et al. (Eds) *Current Protocols in Molecular Biology* (2007), John Wiley and Sons, Inc. and in *Molecular Cloning: A Laboratory Manual*, 4th ed., Green and Sambrook, 2012. Examples of suitable markers include fluorescent molecules (e.g. acetylaminofluorene, 5-bromodeoxyuridine, digoxigenin, fluorescein) and radioactive isotopes (e.g. 32P, 35S, 3H, 33P). Detection of the marker may be achieved, for example, by chemical, photochemical, immunochemical, biochemical, or spectroscopic techniques.

In hybridization techniques, all or part of a known nucleotide sequence is used to generate a probe that selectively hybridizes to other corresponding nucleic acid sequences present in a given sample. The hybridization probes may be genomic DNA fragments, cDNA fragments, RNA fragments, or other oligonucleotides, and may be labelled with a detectable marker. Thus, for example, probes for hybridization can be made by labelling synthetic oligonucleotides based on the sequences of the invention.

The level of homology (sequence identity) between probe and the target sequence will largely be determined by the stringency of hybridization conditions. In particular the nucleotide sequence used as a probe may hybridize to a homologue or other variant of a polynucleotide disclosed herein under conditions of low stringency, medium stringency or high stringency. There are numerous conditions and factors, well known to those skilled in the art, which may be employed to alter the stringency of hybridization. For instance, the length and nature (DNA, RNA, base composition) of the nucleic acid to be hybridized to a specified nucleic acid; concentration of salts and other components, such as the presence or absence of formamide, dextran sulfate, polyethylene glycol etc; and altering the temperature of the hybridization and/or washing steps.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37 C, and a wash in 1× to 2×SSC (20×SSC=3.0 M NaCl/0.3 M trisodium citrate) at 50° C. to 55 C. Exemplary moderate stringency conditions include hybridization in 40% to 45% formamide, 1.0 M NaCl, 1% SDS at 37 C, and a wash in 0.5× to 1×SSC at 55° C. to 60 C. Exemplary high stringency conditions include hybridization in 50% formamide, 1 M NaCl, 1% SDS at 37 C, and a final wash in 0. IX SSC at 60° C. to 65° C. for at least about 20 minutes. Optionally, wash buffers may comprise about 0.1% to about 1% SDS. The duration of hybridization is generally less than about 24 hours, usually about 4 to about 12 hours.

Under a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2nd ed., Cold Spring Harbor Laboratory Press, Plainview, N.Y.); Ausubel F. M. et al. (Eds) *Current Protocols in Molecular Biology* (2007), John Wiley and Sons, Inc; *Molecular Cloning: A Laboratory Manual*, 4th ed., Green and Sambrook, 2012; Maniatis et al. *Molecular Cloning* (1982), 280-281; Innis et al. (Eds) (1990) *PCR Protocols: A Guide to Methods and Applications* (Academic Press, New York): Innis and Gelfand, (Eds) (1995) *PCR Strategies* (Academic Press, New York); and Innis and Gelfand, (Eds) (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

The skilled addressee will recognise that the primers described herein for use in PCR or RT-PCR may also be used as probes for the detection of sequences of interest, such as for the detection of interferon alpha induced protein 27 (IFI27) gene product.

In a particular embodiment a fragment or probe is a fragment of the IFI27 gene, for example a fragment that may be used in hybridisation analysis, such as northern analysis. As a specific example, Suomela et al (2004) describe that a 482 bp fragment of human IFI27 cDNA used to detect IFI27 RNA transcripts in total RNA isolates from cultured human cells. Any appropriate length fragment of IFI27 nucleic acid sequence, or a variant thereof, may be used in the methods of the invention. The skilled addressee will be able to determine an appropriate sequence on the basis of the information provided herein and according to methods known in the art, for example methods for the selection of a sequence, which selectively binds to the target sequence under desired conditions.

In a particular embodiment a fragment, probe or primer is a fragment of the IFI27 gene, for example the sequence ACCTCATCAGCAGTGACCAGT (forward primer; SEQ ID NO:7) or the sequence ACATCATCTTGGCTGCTATGG (reverse primer; SEQ ID NO:8). In a specific embodiment of the method of the invention PCR may be performed using the primer pair ACCTCATCAGCAGTGACCAGT (SEQ ID NO:7) and the sequence ACATCATCTTGGCTGCTATGG (SEQ ID NO:8), which amplifies a sequence of 187 bp (SEQ ID NO: 11).

In a particular embodiment a fragment, probe or primer is a fragment of the IFI27 gene, for example a sequence known in the art as specific for an IFI27 gene or fragment or variant thereof. The skilled addressee will be able to determine appropriate conditions for the use of such nucleic acid sequences in the methods of the invention.

In a particular embodiment a fragment, probe or primer is a fragment of the IFI27 gene, for example the sequence TGC CTC GGG CAG CCT (SEQ ID NO:9) or the sequence TTG GTC AAT CCG GAG AGT CC (SEQ ID NO:10). In a specific embodiment of the method of the invention PCR may be performed using the primer pair TGC CTC GGG CAG CCT (forward primer; SEQ ID NO:9) and the sequence TTG GTC AAT CCG GAG AGT CC (reverse primer; SEQ ID NO:10)[5]. The skilled addressee will be able to determine appropriate conditions for the use of such nucleic acid sequences in the methods of the invention. The skilled addressee will also find guidance on the use of such nucleic acid sequences for the amplification and detection of IFI27 gene product in Suomela et al[5], the contents of which are incorporated herein by reference.

In a particular embodiment a fragment, probe or primer is a fragment of the IFI27 gene, for example the sequence cag gaa ttc atA TGG AGG CCT CTG CTC TCA (ISG12f; SEQ ID NO:16) or the sequence cgc gaa ttc agC TAG TAG AAC CTC GCA ATG (ISG12r; SEQ ID NO:17). In a specific embodiment of the method of the invention PCR may be performed using the primer pair cag gaa ttc atA TGG AGG CCT CTG CTC TCA (ISG12f; SEQ ID NO:16) and the sequence cgc gaa ttc agC TAG TAG AAC CTC GCA ATG (ISG12r; SEQ ID NO:17)[8]. In the sequences stated as ISG12f and ISG12r the uppercase letters correspond to cDNA sequences. The skilled addressee will be able to determine appropriate conditions for the use of such teleic acid sequences in the methods of the invention. The skilled addressee will also find guidance on the use of such nucleic acid sequences for the amplification and detection of IFI27 gene product in Gjermandsen et al (1999)[8], the contents of which are incorporated herein by reference.

Antibodies

Also contemplated by the methods of the invention are antibodies, which are capable of binding specifically to a polypeptide, encoded by IFI27 gene, or a fragment or variant thereof. An antibody or antibodies may be used to qualitatively or quantitatively detect and analyse one or more polypeptides in a given sample, specifically polypeptides or fragments encoded by an IFI27 gene. Antibody detection and quantitation of additional polypeptides for the purpose of control or standardization of an assay may also be conducted. By "binding specifically" it will be understood that the antibody is capable of binding to the target polypeptide or fragment thereof with a higher affinity than it binds to an unrelated protein. For example, the antibody may bind to the polypeptide or fragment thereof with a binding constant in the range of at least about $10^4$M to about $10^{-10}$M. Preferably the binding constant is at least about $10^{-5}$M, or at least about $10^{-6}$M, more preferably the binding constant of the antibody to the polypeptide or fragment thereof of interest is at least about $10^{-7}$M, at least about $10^{-8}$M, or at least about $10^{-9}$M or more.

The antibodies may exist in a variety of forms, including for example as a whole antibody, or as an antibody fragment, or other immunologically active fragment thereof, such as complementarity determining regions. Similarly, the antibody may exist as an antibody fragment having functional antigen-binding domains, that is, heavy and light chain variable domains. Also, the antibody fragment may exist in a form selected from the group consisting of, but not limited to: Fv, Fab, F(ab)$_2$, scFv (single chain Fv), dAb (single domain antibody), chimeric antibodies, bi-specific antibodies, diabodies and triabodies.

An antibody 'fragment' may be produced by modification of a whole antibody or by synthesis of the desired antibody fragment. Methods of generating antibodies, including antibody fragments, are known in the art and include, for example, synthesis by recombinant DNA technology. The skilled addressee will be aware of methods of synthesising antibodies, such as those described in, for example, U.S. Pat. No. 5,296,348 and Ausubel F. M. et al. (Eds) *Current Protocols in Molecular Biology* (2007), John Wiley and Sons, Inc.

Preferably antibodies are prepared from discrete regions or fragments of the polypeptide of interest. An antigenic portion of a polypeptide of interest may be of any appropriate length, such as from about 5 to about 15 amino acids. Preferably, an antigenic portion contains at least about 5, 6, 7, 8, 9, 10, 11, 12, 13 or 14 amino acid residues.

In the context of this specification reference to an antibody specific to a polypeptide encoded by an IFI27 gene also includes an antibody that is specific to a fragment or variant of the polypeptide of interest.

Antibodies that specifically bind to a polypeptide of the invention can be prepared, for example, using a purified polypeptide encoded by an IFI27 gene using any suitable methods known in the art. For example, a monoclonal antibody, typically containing Fab portions, may be prepared using hybridoma technology described in Harlow and Lane (Eds) *Antibodies—A Laboratory Manual*, (1988), Cold Spring Harbor Laboratory, N.Y; Coligan, *Current Protocols in Immunology* (1991); Goding, *Monoclonal Antibodies: Principles and Practice* (1986) 2nd ed; and Kohler & Milstein, (1975) Nature 256: 495-497. Such techniques include, but are not limited to, antibody preparation by selection of antibodies from libraries of recombinant antibodies in phage or similar vectors, as well as preparation of polyclonal and monoclonal antibodies by immunizing rabbits or mice (see, for example, Huse et al. (1989) Science 246: 1275-1281; Ward et al. (1989) Nature 341: 544-546).

It will also be understood that antibodies of the invention include humanised antibodies, chimeric antibodies and fully human antibodies. An antibody of the invention may be a bi-specific antibody, having binding specificity to more than one antigen or epitope. Methods for the preparation of humanised antibodies, chimeric antibodies, fully human antibodies, and bispecific antibodies are known in the art and include, for example as described in U.S. Pat. No. 6,995,243 issued Feb. 7, 2006 to Garabedian, et al. and entitled "Antibodies that recognize and bind phosphorylated human glucocorticoid receptor and methods of using same".

Generally, a sample potentially comprising a polypeptide encoded by an IFI27 gene can be contacted with an antibody that specifically binds the polypeptide or fragment thereof. Optionally, the antibody can be fixed to a solid support to facilitate washing and subsequent isolation of the complex, prior to contacting the antibody with a sample. Examples of solid supports include, for example, microtitre plates, beads, ticks, or microbeads. Antibodies can also be attached to a ProteinChip array or a probe substrate as described above.

Detectable labels for the identification of antibodies bound to the polypeptide of interest include, but are not limited to fluorochromes, fluorescent dyes, radiolabels, enzymes such as horse radish peroxide, alkaline phosphatase and others commonly used in the art, and colorimetric labels including colloidal gold or coloured glass or plastic beads. Alternatively, the marker in the sample can be detected using an indirect assay, wherein, for example, a second, labelled antibody is used to detect bound marker-specific antibody.

Methods for detecting the presence of or measuring the amount of, an antibody-marker complex include, for example, detection of fluorescence, chemiluminescence, luminescence, absorbance, birefringence, transmittance, reflectance, or refractive index such as surface plasmon resonance, biosensor, ellipsometry, a resonant mirror method, a grating coupler wave guide method or interferometry. Radio frequency methods include multipolar resonance spectroscopy. Electrochemical methods include amperometry and voltametry methods. Optical methods include imaging methods and non-imaging methods and microscopy.

Useful assays for detecting the presence of or measuring the amount of, an antibody-marker complex include, include, for example, enzyme-linked immunosorbent assay (ELISA), a radioimmune assay (RIA), or a Western blot assay. Such methods are described in, for example, Clinical Immunology (Stites & Terr, eds., 7th ed. 1991); *Methods in Cell Biology*: Antibodies in Cell Biology, volume 37 (Asai, ed. 1993); and Harlow & Lane, supra.

In a particular embodiment the method of the invention may utilise one or more antibodies known in the art. Antibodies capable of binding to IFI27 polypeptides are known in the art and include anti-IFI27 polyclonal antibody catalogue number: LS-C70809, LSBio; IFI27 polyclonal antibody (A01) catalogue number: H00003429-A01, Abnova Corporation; IFI27 polyclonal antibody catalogue number: PAB8961, Abnova Corporation; IFI27 Antibody catalogue number: H00003429-A01, Novus Biologicals; IFI27 Antibody catalogue number: H00003429-D01P, Novus Biologicals; IFI27 rabbit polyclonal antibody (Sapphire Bioscience, USA), IFI27 MaxPab rabbit polyclonal antibody.

As noted herein, investigation of IFI27 expression by immunoassay and related methods has been reported in the literature, such as by Nzeusseu Toukap et al (2007; the contents of which are incorporated herein by reference), and it will be appreciated that the methods, reagents, devices and kits of the present invention may incorporate the use of antibodies previously reported for the investigation of IFI27. It will be appreciated that the invention and therefore the methods, reagents, devices and kits of the invention include any suitable antibody according to the description herein, and is not limited only to those antibodies specifically mentioned herein. The skilled addressee will be aware that suitable antibodies may be identified through literature searches, routine testing and may be listed in online databases, such as www.antibodies-online.com.

Methods and Kits for Detection

As used herein, determining the level of the interferon alpha inducible protein 27 (IFI27) gene product may in various embodiments include determining the presence, absence, or amount of a gene product in a sample, and may include quantifying the amount of gene product in a sample. In preferred embodiments all steps of the method of the invention occur outside the subject body, such as a subject human body or animal body, such that the method is not practiced on the body. As such, in preferred embodiments the invention does not involve any physical intervention practiced on the human or animal body.

Determining the level of the IFI27 gene product includes relative quantification, such as where a given sample is assessed for the presence of an IFI27 gene product by comparison to another sample or reference, for example where the test sample is found to be more than, less than or about the same amount of gene product as the reference.

Quantifying, and hence determining the level may also include normalization of the sample or the method to account for differences within the assay specific to the sample. Typically this includes determining the level of another component detectable in the sample. For example, where determining the level of an IFI27 gene product comprises determination of the level of an IFI27 mRNA transcript, samples may be normalized to account for inter-sample differences in performance of the invention. The internal reference marker may be any appropriate component in the sample, such as a gene product and would typically be a component the presence of which is uniform in samples from healthy subjects and in unhealthy subjects, or a component the presence of which is uniform in samples from subjects not infected with influenza and in subjects infected with influenza. As a specific example, a glyceraldehyde 3-phosphate dehydrogenase (GAPDH) gene product is used as an internal reference.

Thus the methods of the invention include comparison of the level of the IFI27 gene product in a biological sample from the patient to a reference standard indicative of clinical risk. Any appropriate reference standard may be used. For example the reference standard may be a sample from a healthy subject or may be an amount of an IFI27 gene product typical of that found in a healthy subject. In this case an elevated level of IFI27 in the patient sample compared to the standard is indicative of clinical risk in the patient. As a further example the reference standard may be a sample from a subject infected with influenza virus who is symptomatic or may be an amount of an IFI27 gene product typical of that found in a subject infected with influenza virus who does not develop severe disease; an elevated level of IFI27 in a patient sample compared to such a reference standard is indicative of clinical risk in the patient.

The reference standard may be indicative of clinical risk, in which case an equal or elevated level of IFI27 gene product in a patient sample compared to such a reference is indicative of clinical risk in a subject.

As a further example the reference standard may be a standard curve defining clinical risk. In this case, the reference standard may be independent of the determination of the level of IFI27 gene product in the patient sample, for example the standard curve may be in the form of a supplied reference curve defining clinical risk.

The reference standard may be prepared at the same time as determining the level of IFI27 gene product in the biological sample from the patient. For example, this may comprise the preparation of the standard by subjecting one or more known sample(s) of an IFI27 gene product to the same methods for determining IFI27 gene product level as the biological sample from said patient, wherein the one or more known sample(s) of an IFI27 gene product are of a pre-determined amount or amounts indicative of clinical risk, or no clinical risk or of selected fold increase over an amount typical of a subject having no or negligible clinical risk, such as 5 fold, 10 fold, 20 fold, 30 fold, 40 fold, 50 fold, 60 fold, 100 fold, 200 fold, 300 fold, 500 fold or 1000 fold.

As illustrated in specific embodiments of the invention herein, and particularly in the examples, where quantitative detection of an IFI27 gene product was undertaken, there was at least an approximate 40-fold to 60-fold increase in the detected IFI27 gene product in samples from patients having developed a severe disease from influenza infection, compared to that seen in healthy or asymptomatic individuals. By comparison to healthy or asymptomatic individuals there was an increase of at least approximately 10-fold in the detected IFI27 gene product in samples from patients with influenza or viral pneumonia.

Determining the level of an IFI27 gene product may also include absolute quantification such as where the amount of an IFI27 gene product in a sample is determined such as may be expressed in appropriate units, for example an amount may be expressed as fold change, units/volume of sample, such as grams, micrograms, nanograms, picograms, femtograms, and the like, per milliliter, microliter, nanoliter and the like.

A cut-off value may be implemented in a variety of embodiments of the invention. For example, in one embodiment a cut-off value may be implemented by quantitative measurement of an actual amount of the IFI27 gene product in a sample, such as measurement in terms of amount/ml of sample. In another embodiment a cut-off value may be implemented by setting a lower limit or threshold of detectability at the desired cut-off value. In this manner detection of the IFI27 gene product in a sample (which, in this context, may be referred to as a positive signal) is indicative of a severe disease due to influenza infection in the subject providing the sample whilst no detectable IFI27 gene product in a sample (which in this context may be referred to as a negative signal) is indicative of the subject providing the sample not having influenza or being asymptomatic. Such an embodiment, at any suitable positive/negative cut-off value may find particular use in situations where a relatively rapid diagnosis is desirable or where relatively sophisticated testing equipment is not always available. This may be, for example, at point of care or in a medical practitioner's consulting rooms.

Detection of polynucleotides and polypeptides disclosed herein may be performed using any suitable method. For example, methods for the detection of an IFI27 gene product, such as a polynucleotide and/or polypeptide may involve the use of a primer, probe or antibody specific for the IFI27 gene product. Suitable techniques and assays in which the skilled addressee may utilise a primer, probe or antibody include, for example, the polymerase chain reaction (and related variations of this technique), antibody based assays such as ELISA and flow cytometry, and fluorescent microscopy. Methods by which the characteristic polypeptides disclosed herein may be identified are generally known in the art, and are described for example in Coligan J. E. et al. (Eds) *Current Protocols in Protein Science* (2007), John Wiley and Sons, Inc; Walker, J. M., (Ed) (1988) *New Protein Techniques: Methods in Molecular Biology*, Humana Press, Clifton, N.J.; and Scopes, R. K. (1987) *Protein Purification: Principles and Practice.* 3rd. Ed., Springer-Verlag, New York, N.Y. For example, polypeptides encoded by IFI27 may be detected by western blot or spectrophotometric analysis. Other examples of suitable methods for the detection of polypeptides are described, for example, in U.S. Pat. No. 4,683,195, U.S. Pat. No. 6,228,578, U.S. Pat. No. 7,282,355, U.S. Pat. No. 7,348,147 and PCT publication No. WO/2007/056723.

In a preferred embodiment of the invention, the detection of and determination of the level of an IFI27 gene product is achieved by amplification of nucleotide sequence from the sample of interest by polymerase chain reaction, using primers that hybridise specifically to a sequence, or a variant or fragment thereof, of the IFI27 gene product and detecting the amplified sequence. In this case a typical target sequence is an IFI27 mRNA such as having a sequence shown in SEQ ID NO:1 or SEQ ID NO:2, or a cDNA sequence of IFI27 such as having a sequence shown in SEQ ID NO:5 or SEQ ID NO:6, or a fragment or variant of any thereof. In embodiments of the invention multiple target sequences, fragments or variants thereof may be employed.

The method may include detection of multiple sequences, fragments or variants thereof. The method may also further comprise the inclusion of controls, such as for the correct or consistent performance of the method or to permit mRNA expression levels to be normalised between samples. For example, the method may include the detection of one or more polynucleotide or polypeptides, or fragment or variant thereof, known to be expressed constitutively, such as GAPDH, or known to be expressed at a consistent level in subjects infected with influenza and in subjects not infected with influenza.

Suitable methods for the extraction and purification, to the extent necessary or desired, of nucleic acids for analysis using the methods and kits invention are generally known in the art and are described, for example, in Ausubel F. M. et al. (Eds) *Current Protocols in Molecular Biology* (2007), John Wiley and Sons, Inc; *Molecular Cloning: A Laboratory Manual,* 4th ed., Green and Sambrook, 2012. The skilled addressee will readily appreciate that the invention is not limited to the specific methods for nucleic acid isolation described therein and other suitable methods are encompassed by the invention. The invention may be performed without nucleic acid isolation prior to analysis of the nucleic acid.

Suitable methods for the extraction and purification, to the extent necessary or desired, of polypeptides for the purposes of the invention are generally known in the art and are described, for example, in Coligan J. E. et al. (Eds) *Current Protocols in Protein Science* (2007), John Wiley and Sons, Inc; Walker, J. M., (Ed) (1988) *New Protein Techniques: Methods in Molecular Biology*, Humana Press, Clifton, N.J.; and Scopes, R. K. (1987) *Protein Purification: Principles and Practice,* 3rd. Ed., Springer-Verlag, New York, N.Y. Examples of suitable techniques for protein extraction include, but are not limited to, dialysis, ultrafiltration, and precipitation. Protein purification techniques suitable for use include, but are not limited to, reverse-phase chromatography, hydrophobic interaction chromatography, centrifugation, gel filtration, ammonium sulfate precipitation, and ion exchange.

In accordance with the methods and kits of the invention, polynucleotides or variants or fragments thereof may be detected by any suitable means known in the art. In a preferred embodiment of the invention, the polynucleotides are detected by PCR amplification. Under the PCR approach, oligonucleotide primers can be designed for use in PCR reactions to amplify a polynucleotide representative of an IFI27 gene product. Typically the PCR comprises quantitative amplification of complementary DNA (cDNA) prepared from messenger RNA (mRNA) by reverse-transcription of relevant sequences (RT-PCR). Known methods of PCR include, but are not limited to, methods using paired primers, nested primers, single specific primers, degenerate primers, gene-specific primers, vector-specific primers, partially-mismatched primers, and the like. Methods for designing PCR and RT-PCR primers are generally known in the art and are disclosed, for example, in Ausubel F. M. et al. (Eds) *Current Protocols in Molecular Biology* (2007), John Wiley and Sons, Inc; Maniatis et al. *Molecular Cloning* (1982), 280-281; Innis et al. (Eds) (1990) *PCR Protocols. A Guide to Methods and Applications* (Academic Press, New York); Innis and Gelfand, (Eds) (1995) *PCR Strategies* (Academic Press, New York); Innis and Gelfand, (Eds) (1999) *PCR Methods Manual* (Academic Press, New York); and Sambrook et al. (1989) *Molecular Cloning: A Laboratory Manual* (2nd ed., Cold Spring Harbor Laboratory Press, Plainview, N.Y.; *Molecular Cloning: A Laboratory Manual.* 4th ed., Green and Sambrook, 2012.

The skilled addressee will readily appreciate that various parameters of PCR and RT-PCR procedures may be altered without affecting the ability to achieve the desired product. For example, the salt concentration may be varied or the time and/or temperature of one or more of the denaturation, annealing and extension steps may be varied. Similarly, the amount of DNA, cDNA, or RNA template may also be varied depending on the amount of nucleic acid available or the optimal amount of template required for efficient amplification. The primers for use in the methods and kits of the present invention are typically oligonucleotides typically being at least about 5 nucleotides to about 80 nucleotides in length, more typically about 10, 11, 12, 13, or 14 nucleotides in length to about 50 nucleotides in length, and even more typically about 15 nucleotides in length to about 30 nucleotides in length, such as any of 15, 16, 17, 18, 19, 20, 21, 22, 23, 24, 25, 26, 27, 28, 29, or 30 nucleotides in length. The skilled addressee will recognise that the primers described herein may be useful for a number of different applications, including but not limited to PCR, RT-PCR, and use of probes for the detection of sequences identified herein as characteristic of the highly invasive strains.

Such primers can be prepared by any suitable method, including, for example, direct chemical synthesis or cloning and restriction of appropriate sequences. Not all bases in the primer need reflect the sequence of the template molecule to which the primer will hybridize, the primer need only contain sufficient complementary bases to enable the primer to hybridize to the template. A primer may also include mismatch bases at one or more positions, being bases that are not complementary to bases in the template, but rather are designed to incorporate changes into the DNA upon base extension or amplification. A primer may include additional bases, for example in the form of a restriction enzyme recognition sequence at the 5' end, to facilitate cloning of the amplified DNA.

The skilled addressee will recognise that any primers capable of the amplifying a sequence representative of an IFI27 mRNA sequence, or fragment thereof, are suitable for use in the methods of the invention. An IFI27 mRNA sequence is shown in SEQ ID NO:1 and 2. Any oligonucleotide primer pairs suitable for amplification of a nucleic acid comprising the sequence of SEQ ID NO:1 and 2 or a fragment or variant thereof may be used. The skilled addressee will be aware that suitable primers and primer pairs can be chosen through routine methods for the detection, such as through PCR amplification, of a sequence representative of an IFI27 mRNA transcript.

As specific examples, the PCR amplification may utilise a primer pair selected from the group consisting of (i) ACCTCATCAGCAGTGACCAGT (forward primer; SEQ ID NO:7) and ACATCATCTTGGCTGCTATGG (reverse primer; SEQ ID NO:8); (ii) TGC CTC GGG CAG CCT (forward primer; SEQ ID NO:9) and TTG GTC AAT CCG GAG AGT CC (reverse primer; SEQ ID NO:10); (iii) cag gaa ttc atA TGG AGG CCT CTG CTC TCA (ISG12f; SEQ ID NO:16) and cgc gaa ttc agC TAG TAG AAC CTC GCA ATG (ISG12r; SEQ ID NO:17).

Also included within the scope of the present invention are variants and fragments of the exemplified oligonucleotide primers. The skilled addressee will also recognise that the invention is not limited to the use of the specific primers exemplified, and alternative primer sequences may also be used, provided the primers are designed appropriately so as to enable the amplification of characteristic sequences of interest. Suitable primer sequences can be determined by those skilled in the art using routine procedures without undue experimentation. The location of suitable primers for the amplification of desired sequences may be determined by such factors as G+C content and the ability for a sequence to form unwanted secondary structures.

Suitable methods of analysis of the amplified nucleic acids are well known to those skilled in the art and are described for example, in, Sambrook et al. (1989) *Molecular Cloning: A Laboratory Manual* (2nd ed., Cold Spring Harbor Laboratory Press, Plainview, N.Y.); Ausubel F. M. et al. (Eds) *Current Protocols in Molecular Biology* (2007), John Wiley and Sons, Inc; and Maniatis et al. *Molecular Cloning* (1982), 280-281. Suitable methods of analysis of the amplified nucleic acids include, for example, gel electrophoresis which may or may not be preceded by restriction enzyme digestion, and/or nucleic acid sequencing. Gel electrophoresis may comprise agarose gel electrophoresis or polyacrylamide gel electrophoresis, techniques commonly used by those skilled in the art for separation of DNA fragments on the basis of size. The concentration of agarose or polyacrylamide in the gel in large part determines the resolution ability of the gel and the appropriate concentration of agarose or polyacrylamide will therefore depend on the size of the DNA fragments to be distinguished.

In other embodiments of the invention, an IFI27 gene product, which is a polynucleotide and variants or fragments thereof may be detected by the use of suitable probes. A probe may be any suitable probe capable of selective hybridization to an IFI27 gene product, such as mRNA or an amplified derivative thereof. Probes are nucleotide sequences of variable length, for example between about 10 nucleotides and several thousand nucleotides, for use in detection of homologous sequences, typically by hybridization. For the detection of a sequence representative of an IFI27 mRNA transcript a probe would typically be of a size less than or equal to the length of the transcript. Hybridization probes of the invention may be genomic DNA fragments, cDNA fragments, RNA fragments, or other oligonucleotides.

Methods for the design and/or production of nucleotide probes are generally known in the art, and are described, for example, in Robinson P. J. et al. (Eds) *Current Protocols in Cvytometry* (2007), John Wiley and Sons, Inc; Ausubel F. M. et al. (Eds) *Current Protocols in Molecular Biology* (2007), John Wiley and Sons, Inc; Sambrook et al. (1989) *Molecular Cloning: A Laboratory Manual* (2nd ed., Cold Spring Harbor Laboratory Press, Plainview, N.Y.; and Maniatis et al. *Molecular Cloning* (1982), 280-281. Nucleotide probes may be prepared, for example, by chemical synthesis techniques, for example, the phosphodiester and phosphotriester methods (see for example Narang S. A. et al. (1979) Meth. Enzymol. 68:90; Brown, E. L. (1979) et al. Meth. Enzymol. 68:109; and U.S. Pat. No. 4,356,270), the diethylphosphoramidite method (see Beaucage S. L et al. (1981) Tetrahedron Letters, 22:1859-1862). A method for synthesizing oligonucleotides on a modified solid support is described in U.S. Pat. No. 4,458,066.

Probes of the invention or for use in methods and kits of the invention may be labelled by incorporation of a marker to facilitate their detection. Techniques for labelling and detecting nucleic acids are described, for example, in Ausubel F. M. et al. (Eds) *Current Protocols in Molecular Biology* (2007), John Wiley and Sons, Inc. Examples of suitable markers include fluorescent molecules (e.g. acetylaminofluorene, 5-bromodeoxyuridine, digoxigenin, fluorescein) and radioactive isotopes (e.g. 32P, 35S, 3H, 33P). Detection of the marker may be achieved, for example, by chemical, photochemical, immunochemical, biochemical, or spectroscopic techniques.

The methods and kits of the invention also encompass the use of antibodies, which are capable of binding specifically to the polypeptides of the invention. The antibodies may be used to qualitatively or quantitatively detect and analyse one or more polypeptides in a given sample. Methods for the generation and use of antibodies are generally known in the art and described in, for example, Harlow and Lane (Eds) *Antibodies—A Laboratory Manual*, (1988), Cold Spring Harbor Laboratory, N.Y: Coligan, *Current Protocols in Immunology* (1991); Goding, *Monoclonal Antibodies: Principles and Practice* (1986) 2nd ed; and Kohler & Milstein, (1975) Nature 256: 495-497. The antibodies may be conjugated to a fluorochrome allowing detection, for example, by flow cytometry, immunohistochemistry or other means known in the art. Alternatively, the antibody may be bound to a substrate allowing colorimetric or chemiluminescent detection. The invention also contemplates the use of secondary antibodies capable of binding to one or more antibodies capable of binding specifically to the polypeptides of the invention.

In the methods of the invention it will be understood that the description of the use of a sample or preparation, for example, includes the use of less than the total amount available as may determined by the skilled addressee as appropriate in the circumstances. For example, in the description of preparing an isolate of total RNA from a blood sample obtained from a patient, the entire blood sample need not be used if the skilled addressee deems appropriate, an aliquot of the sample may instead be used. As another example, in the preparation of cDNA by reverse transcription of a total RNA isolate, the entire total RNA isolate need not be used if the skilled addressee deems appropriate, an aliquot of the total RNA isolate may instead be used.

Kits

The invention also provides kits for determining the level of an interferon alpha inducible protein 27 (IFI27) gene product in a biological sample, the kit comprising at least one agent for detecting the presence of an IFI27 gene product. The agent may be an agent capable of detecting an IFI27 gene product, where the gene product may be a polynucleotide or polypeptide. Any suitable agent capable of detecting sequences described herein may be included in the kit. Non-limiting examples include primers, probes and antibodies.

The kit may comprise at least one agent, which is a primer, antibody or probe. The primer or probe may be specific for a nucleic acid sequence as shown in SEQ ID NO:1 or SEQ ID NO:2, or a variant or fragment thereof. The primer or probe may be selected from SEQ ID NO:7 and SEQ ID NO:8. The primer or probe may be selected from any of the sequences of the group consisting of (i) ACCT-CATCAGCAGTGACCAGT (forward primer; SEQ ID NO:7) and ACATCATCTTGGCTGCTATGG (reverse primer; SEQ ID NO:8); (ii) TGC CTC GGG CAG CCT (forward primer; SEQ ID NO:9) and TTG GTC AAT CCG GAG AGT CC (reverse primer; SEQ ID NO: 10); (iii) cag gaa ttc atA TGG AGG CCT CTG CTC TCA (ISG12f; SEQ ID NO:16) and cgc gaa ttc agC TAG TAG AAC CTC GCA ATG (ISG12r; SEQ ID NO:17).

The kit may comprise multiple agents capable of detecting the presence of an IFI27 gene product in a biological sample.

The kit may comprise an antibody capable of specifically binding to a polypeptide, or an antigenic fragment or variant thereof, encoded by an IFI27 gene sequence. The kit may comprise an antibody capable of selectively binding to an IFI27 polypeptide comprising an amino acid sequence shown in SEQ ID NO:3 or SEQ ID NO:4, or an antigenic fragment or variant thereof.

The kit may comprise one or more agents for normalisation of the method of the invention. The agent(s) for normalisation may be selected from the group consisting of an agent for the detection of a constitutively expressed gene product, such as GAPDH. For example the kit may comprise one or more nucleic acid sequences capable of selectively binding to a GAPDH nucleotide sequence. The one or more nucleic acid sequences capable of selectively binding to a GAPDH nucleotide sequence may be one or more of the sequences shown in SEQ ID NO:13, SEQ ID NO:14, SEQ ID NO:15 or SEQ ID NO:16, or a fragment or variant of any thereof.

The kit may comprise one or more calibrated standards wherein the standard comprises a known concentration of IFI27 gene product.

The kit may comprise one or more additional components selected from the group consisting of (i) one or more reference sample(s); (ii) one or more detectable moieties; (iii) one or more substance(s) for immobilising an agent for detecting an IFI27 gene product on a solid support; (iv) a solid support material; (v) one or more container(s) for collection and/or storage of a biological sample; (vi) one or more reagent(s) for use in preparation of a biological sample; (vii) one or more agents for the amplification of a nucleic acid sequence; and (viii) instructions for use of the kit or a component(s) thereof in a method for determining the level of an IFI27 gene product in a biological sample.

In general, the kits of the invention may comprise any number of additional components.

By way of non-limiting examples the additional components may include, reagents for cell culture, reference samples, buffers, labels, and written instructions for performing the detection assay.

EXAMPLES

The invention will now be described with reference to specific examples, which should not be construed as in any way limiting the scope of the invention.

Example 1: Materials and Methods

Study Participants

Experiments were performed based on a study sample consisting of a development set and a validation set. The development set (n=54) was used to identify the candidate biomarker for influenza infection. It included several cohorts of patients; influenza infection (n=8), bacterial infection (n=16), critically ill patients with non-infectious conditions (n=12) and healthy volunteers (n=18). The validation set (n=33) was used to test the biomarker generated from the development set. All study participants gave informed written consent and details of study participants are available in Table 1.

TABLE 1

Demographic and clinical characteristics of individuals in development and validation sets.

| | Development Set | | | Validation Set | Control Set |
| --- | --- | --- | --- | --- | --- |
| | Severe Influenza Pneumonia | Severe Bacterial Pneumonia | Patients with SIRS | Severe Influenza Pneumonia | Healthy Volunteers |
| Demographics | | | | | |
| Number | 8 | 16 | 12 | 33 | 18 |
| Age (years) | 34.875 ± 13.2 | 61.4 ± 13.4 | 61.5 ± 15.6 | 48 ± 15 | 43 ± 16 |
| Male/female | 3/5 | 7/9 | 10/2 | 9/24 | 6/12 |
| Severity (%) | | | | | |
| APACHE | 18.5 ± 6.5 | 19 ± 6.2 | 16.66 ± 4.5 | 23 ± 7.9 | NA |
| Mortality | 0 | 31.3 | 0 | 15.2 | NA |
| Ventilation | 100 | 93.8 | 75 | 90.9 | NA |

TABLE 1-continued

Demographic and clinical characteristics of individuals in development and validation sets.

|  | Development Set | | | Validation Set | Control Set |
| --- | --- | --- | --- | --- | --- |
|  | Severe Influenza Pneumonia | Severe Bacterial Pneumonia | Patients with SIRS | Severe Influenza Pneumonia | Healthy Volunteers |
| Dialysis | 12.5 | 6.3 | 8.3 | 6.1 | NA |
| Inotropes | 62.5 | 56.3 | 16.7 | 3.0 | NA |
| Comorbidity (%) | | | | | |
| Hypertension | 12.5 | 31.3 | 58.3 | 36.3 | 16.6 |
| Heart Disease | 0 | 37.5 | 33.3 | 6.1 | 0 |
| Diabetes | 12.5 | 12.5 | 25.0 | 18.2 | 0 |
| COPD | 25.0 | 37.5 | 16.7 | 15.2 | 0 |
| Cancer | 0 | 12.5 | 0 | 0 | 0 |
|  | | | Total = 87 | | |

(COPD, chronic obstructive pulmonary disease; APACHE II, acute physiology and chronic health evaluation score; SIRS, systemic inflammatory response syndrome. Plus-minus values are means ± standard deviation)

Gene Expression Analysis

To screen for potential candidate markers, transcriptome microarray analysis was performed on whole blood from individuals with confirmed influenza infection. RNA extraction was performed using the standard protocol (PAXgene™ Blood RNA kit—Qiagen, Germany). RNA quality was analyzed using Agilent Bioanalyser and all samples had RNA integrity numbers greater than 6.5, indicating high quality of samples. Sample amplification and labelling was carried out on 200 ng of total RNA using an Illumina TotalPrep Amplification kit, in batches of 24 samples at a time (Ambion, Austin, Tex.). Amplified cRNA was assessed using the Agilent Bioanalyser, to ensure satisfactory amplification.

The samples (750 ng of each sample) were immediately hybridized onto HT-12_v3_BeadChips. The hybridization and washing procedure was identical for each set of arrays processed and, after normalization, no significant batch effects were identified. To minimize experimental artifacts, RNA extraction, sample amplification and labelling, hybridization and washing, and scanning was carried out by the same operator, at the same time of day. All microarray data are available on the Gene Expression Omnibus (GEO) (GSE40012), in accordance with minimum information about a microarray experiment (MIAME) standards.

Prior to analysis, each probe on the array was passed through a filter requiring a detection p-value of less than 0.0050 in at least one sample to be included in any further analyses. Of the 48,804 probes present on the Illumina HT 12 array, 24840 probes (henceforth referred to as genes) passed this criterion. Genes which passed the filtering were loaded into BRB ArrayTools where quantile normalisation and log transformation of the data was applied. Validation of the microarray experiment was performed by measuring the expression relative to GAPDH for a subset of genes, using qRT-PCR. The R-squared values obtained when comparing qRT-PCR and microarray relative fold-changes ranged from 0.67 to 0.83, indicating strong concordance between the two gene-expression platforms.

Genes with low variance across all samples, defined to be less than the median, were removed from the dataset. P-values were adjusted for multiple testing using the Benjamani and Hochberg False Discovery Rate (FDR) method (R library multtest). A FDR of 5% was used as the cut-off for genes deemed to be differentially expressed between the two classes.

Quantitative Real-Time PCR

Quantitative real-time PCR was performed on all samples in the development and validation sample sets. Total RNAs were prepared with Qiagen RNEASY mini kit according to the manufacturer's instructions (Qiagen, Germany). RNA yield was determined by UV absorbance.

The first strand cDNAs were prepared using SUPERSCRIPT III RT-PCR system, RNaseOut, Oligo (dT) and random primer (Invitrogen) in a Mastercycler®gradient 5331 (Eppendorf AG, Hamburg, Germany). For RT-PCR reactions, samples were run in duplicate. The PCR reaction volume was 25 ul containing 5 ul cDNA sample, 1 ul of each primer, 12.5 ul of POWER SYBR green PCR master mix (Applied Biosystems) and 5.5 ul RNase free water. Oligonucleotide primers (Sigma Aldrich) were designed so that the PCR product spanned an intron and were verified on the UCSC in silico PCR website (http://genome.ucsc.edu/cgi-bin/hgPcr?command?command=start).

Primers used for the amplification of IFI27 were 5'-ACCTCATCAGCAGTGACCAGT-3' (forward) (SEQ ID NO.: 7) and 5'-ACATCATCTTGGCTGCTATGG-3' (reverse) (SEQ ID NO.: 8). PCR cycling conditions were: hold at 95° C. for 10 min, 5 cycles of 95° C. for 30 sec, 64° C. for 30 sec, then 72° C. for 30 sec 35 cycles of 95° C. for 30 sec, 59° C. for 30 sec, then 72° C. for 30 sec, melt from 75° C. to 99° C. Expression level of IFI27 was normalized using the human housekeeping gene, GAPDH 5'-ACGCATTTG-GTCGTATTGGG-3' (forward) (SEQ ID NO.: 14) and 5'-TGATTTTGGAGGGATCTCGC-3' (reverse) (SEQ ID NO.: 15). Assays were run on a Rotor-Gene 2000 real-time PCR machine (Corbett Research, NSW, Australia). Single PCR products were confirmed by both melt curve analysis and by observation of a single product when run on an ethidium bromide stained 2% agarose gel (Sigma-Aldrich), visualized by UV-transillumination. Visualization of gene expression data was generated using GRAPHPAD PRISM software (Version 6).

Cell Culture

For experiments performed in human immune cells, culture medium consisting of Gibco RPMI 1640 medium (Life Technologies, Australia Pty Ltd) supplemented with 10% fetal bovine serum (FBS; SAFC Biosciences, Victoria, Australia) 50 IU/ml penicillin, 50 µg/ml streptomycin, and 2 mM L-glutamine was used. All cultured cells were maintained at 37° C. in a humidified atmosphere of 5% $CO_2$.

Isolation of Immune Cell Subsets

Human cell types (monocytes, NK cells, B cells, pDCs, mDCs, $CD4^+$, $CD8^+$ T-cells, and Neutrophils) were purified from whole Peripheral blood mononuclear cells (PBMCs).

To isolate PBMCs, 35 ml of whole blood was loaded on 15 ml of Ficoll, in 50 ml Falcon tubes and centrifuged at 400×g for 30 min at 20° C., with brake off. The white layer located in the interface was extracted carefully into new Falcon tubes. The isolated PBMCs were washed twice with Dulbecco's Phosphate Buffer Saline without $Ca^{2+}$ or $Mg^{2+}$ (DPBS; Lonza, Walkersville, Md., USA). The number of nucleated cells was determined by staining with crystal violet.

Monocytes were isolated from fresh human PBMCs using EASYSEP Human Monocytes Enrichment Kit (negative selection-STEMCELL Technologies, Australia) by following the manufacturer's instructions. The kit depletes a small subset of CD+16 monocytes. Cells were fluorescently stained with CD14-FITC and analyzed by flow cytometry. The purity was always more than 92%.

Natural killer (NK) cells were isolated from human PBMCs using EASYSEP human NK cell enrichment kit (negative selection-STEMCELL Technologies, Australia). The kit enriches NK cells by depletion of non-NK cells. Purity of NK cells was measured by flow cytometry after staining with CD56-PE.Cy7 and CD3-FITC. The purity was always more than 94%.

B cells were enriched to >98% purity (CD19+) by magnetic cell separation (negative selection) using a Human B Cell Enrichment Kit (STEMCELL Technologies, Australia). The purity was always more than 90%.

Myeloid Dendritic Cells (mDCs) were isolated from human PBMCs using the Myeloid Dendritic Cell Isolation Kit (negative selection, Miltenyi Biotec. N.S.W., Australia). mDCs are isolated by depletion of non-mDCs. Non-mDCs were indirectly magnetically labelled with a cocktail of biotin-conjugated antibodies before addition of antibiotin-conjugated microbeads as a secondary labelling reagent. The magnetically labelled non-mDCs were depleted by retaining these cells on a MACS column. The unlabeled mDCs pass through the column. Cells were fluorescently stained with CD141 (BDCA-3)-FITC, CD1c (BDCA-1)-APC and analyzed by flow cytometry. The purity was always more than 90%.

Plasmacytoid Dendritic Cells (pDCs) were isolated from human PBMCs using EASYSEP Human plasmacytoid DC Enrichment Kit (negative selection-STEMCELL Technologies, Vic, Australia). The kit enriches pDCs from PBMCs by depletion of non-pDCs. Cells were fluorescently stained with CD304 (BDCA-4)-APC and HLA-DR-PerCP and analyzed by flow cytometry. The purity was always more than 92%.

Monocyte derived dendritic cells (MDDC) (>90% CD14+) were obtained either by collection of plastic-adherent cells or by treating PBMCs with RosetteSep CD14+ enrichment kit (STEMCELL Technologies, Australia). Isolated monocytes were then subsequently cultured for six days in complete media supplemented with suitable concentrations of recombinant human IL-4 and GM-CSF (eBioscience, San Diego, Calif., USA).

CD4+ T cells were freshly isolated by negative selection (STEMCELL Technologies, Australia) according to the protocol provided by the manufacturer. The purity of CD3+/CD4+ T cells was ≥96%.

CD8+ T cells were isolated by CD8 negative selection using the EASYSEP CD8 enrichment kit (STEMCELL Technologies, Australia). Purity of the CD3+/CD8+ T cells was verified by flow cytometry (>95%).

Neutrophils were isolated from a total of 10 to 20 mL human blood obtained from healthy donors, using heparin to prevent clotting. All subsequent steps were performed at 4° C. or on ice. The blood was diluted 1:1 with Hank's Balanced Salt Solution (HBSS; Life Technologies, Victoria, Australia) with 2% Dextran T500 (Pharmacia) and incubated 30 minutes to sediment red blood cells. The upper phase was transferred to a new tube and density fractionated using Ficoll-Paque™PLUS (GE HealthCare, Australia). Neutrophils were recovered from the pellet and mononuclear cells were recovered from the interface. The pellet was transferred to a new tube and re-suspended in RBC lysis buffer (150 mM Ammonium Chloride, 1 mM Potassium Bicarbonate, 0.1 mM EDTA, pH 7-2) and then washed with RPMI 1640 supplemented with 10% low-endotoxin fetal bovine serum (FBS) and antibiotics. Typical recovery was three to five million neutrophils per milliliter of collected blood. Purity was more than 92%. Neutrophils were isolated before each experiment and used immediately.

Macrophages were prepared from PBMCs from healthy blood donors that were purified as previously described. Macrophages were generated from purified monocytes with 10 ng/ml of macrophage-colony stimulating factor (M-CSF; R&D Systems in 96-well plates (Becton Dickinson, Franklin Lake, N.J., USA) at a density of $1.5 \times 10^6$ cells/well in RPMI 1640 medium supplemented with 10% fetal calf serum, 2 mM L-glutamine, and 50 IU/ml penicillin, and 50 µg/ml streptomycin. On days two and five, half of the medium was refreshed, and on day six monocyte-derived macrophages were harvested. The cell populations obtained contained >90% macrophages.

Immune Cell Separation and FACS Analysis

Cells were separated based on differential expression of surface markers as shown in Table 2. In each experiment, cells (>$10^4$ cells per sample) were suspended in the medium and the purity of freshly isolated cells (cell surface phenotype) was determined either immediately or fixed in 1% paraformaldehyde for later analysis by flow cytometry BD LSR-II (BD Biosciences). Analysis was performed using the FlowJo software program (Tree Star, USA).

TABLE 2

Antibodies used for flow cytometry to purify immune cell subsets

| Conjugated antibody | Clone name | Isotype | Company |
|---|---|---|---|
| CD1c (BDCA-1)-APC | L161 | ms IgG1, κ | Biolegend |
| HLA-DR-PerCP | L243 | ms IgG2a, κ | Biolegend |
| CD14-FITC | HCD14 | ms IgG1, κ | Biolegend |
| CD56-PECy7 | NCAM16.2 | ms IgG2b, κ | BD Bioscience |
| CD4-FITC | SK3 | ms IgG1, κ | BD Bioscience |
| CD8-PerCP | SK1 | ms IgG1, κ | BD Bioscience |
| CD304-APC | AC144 | ms IgG1 | Miltenyi Biotec |
| CD45-PE | HI30 | ms IgG1, κ | Biolegend |
| CD19-FITC | 4G7 | ms IgG1, κ | BD Bioscience |
| CD19-APC | HIB19 | ms IgG1, κ | Biolegend |
| CD16-Pacific Blue | eBioCB16 | ms IgG1, κ | eBioscience |
| CD3-Pacific Orange | UCHT1 | ms IgG1, κ | BD Pharmingen |

Cell Stimulation Assay

Isolated immune cells were stimulated by endogenous ligands, including interferon-alpha, interferon-beta, interferon-lambda, influenza viral antigen, agonists of toll-like receptors (TLR1, TLR2, TLR3, TLR4, TLR5, TLR6, TLR7, TLR8, and TLR9), as well as live influenza viruses (H1N1, H3N2, influenza B). Pure cell populations were re suspended in RPMI 1640 containing 10% FBS, 2 mM L-glutamine, 50 IU/ml penicillin, and 501 g/ml streptomycin at the density of $1-2\times10^6$ cells per ml. To determine the effect that different concentrations of stimulators have on IFI27 expression, cells were incubated for 6, 12, and 24 hours at 37° C. with the indicated concentrations of stimulators in media. For all treatments, a dose response was performed to define optimal stimulating conditions. Cell viability before and after stimulation was measured by the method of Trypan blue exclusion (Sigma-Aldrich, St Louis, Mo., USA).

Statistical Analysis

Comparisons between 2 groups were calculated using unpaired two-tailed Student's t-test or the non-parametric Mann-Whitney U test where appropriate. Comparison between multiple groups was calculated using a one-way ANOVA or the Kruskal-Wallis test where appropriate. Gene-expression data are represented as fold change relative to healthy controls (mean+/−SD). All statistical analysis was performed using GRAPHPAD PRISM software version 6 (GRAPHPAD Software, La Jolla, Calif.). All p values are two-sided with the significance threshold considered to be $p<0.05$.

Example 2: IFI27 is Highly Expressed in Severe Influenza Infection

Figure 2:
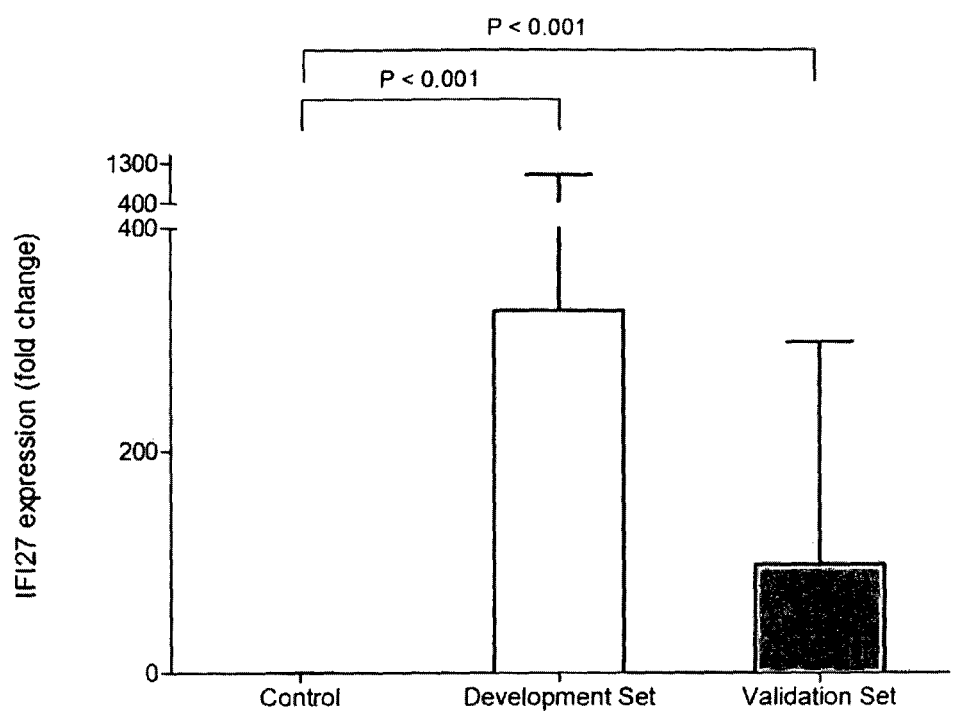
FIG. 2 shows IFI27 expression in severe influenza infection. The development set (n=8) and validation set (n=33) consist of individuals with severe influenza pneumonia, who developed respiratory failure and required admission to intensive care units. Control set (n=18) consists of healthy volunteers. Peripheral blood IFI27 gene expression was measured by PCR. Bar chart depicts mean fold change+/−SD. p values were calculated using non-parametric Mann-Whitney U test.

To screen for potential candidate markers, a transcriptome microarray analysis on whole blood of patients with confirmed influenza infection was performed. This analysis identified an interferon-stimulated gene, interferon alpha-inducible protein 27 (IFI27), as a marker of severe influenza infection (FIG. 1). In the development set, the IFI27 gene was highly expressed in individuals with severe disease from influenza infection. This finding was confirmed in the validation set (FIG. 2).

Figure 3:
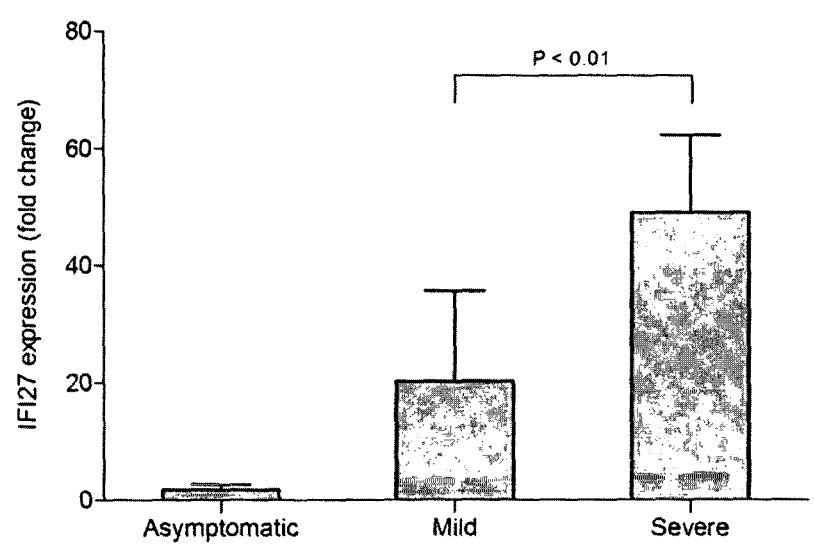
FIG. 3 shows IFI27 expression and severity of influenza infection. Validation of biomarker using independent datasets in individuals with mild disease and severe disease. Mild infection cohort includes asymptomatic (n=8) and symptomatic individuals (n=9). Severe infection cohort (n=10) includes individuals who developed respiratory failure and required admission to intensive care units. Gene expression omnibus (GEO) provides microarray datasets for calculation of IFI27 expression (GSE17156—mild influenza, GSE21802—severe influenza). Bar chart depicts mean fold change+/−SD. p values were calculated using non-parametric Mann-Whitney U test.

The correlation between IFI27 expression level and disease severity was further validated in two independent gene-expression datasets (GSE17156, GSE21802), where it was found IFI27 expression was minimal in individuals with asymptomatic infection, moderately increased in symptomatic infection and significantly increased in those with severe disease from the infection (FIG. 3). Among cohorts of individuals who developed severe disease, a higher mean IFI27 expression (>90 fold change) was associated with a higher proportion of individuals requiring mechanical ventilation (Table 3).

TABLE 3

IFI27 expression in patients with severe influenza pneumonia

| Cohorts | Number of Individuals | Mechanical Ventilation (%) | IFI27 expression (fold change - mean) |
|---|---|---|---|
| Development Set | n = 8 | 8 (100%) | 325 |
| Validation Set | n = 33 | 30 (91%) | 97 |
| Independent Set (GSE21802) | n = 10 | 4 (40%) | 58.7 |

Figure 4:
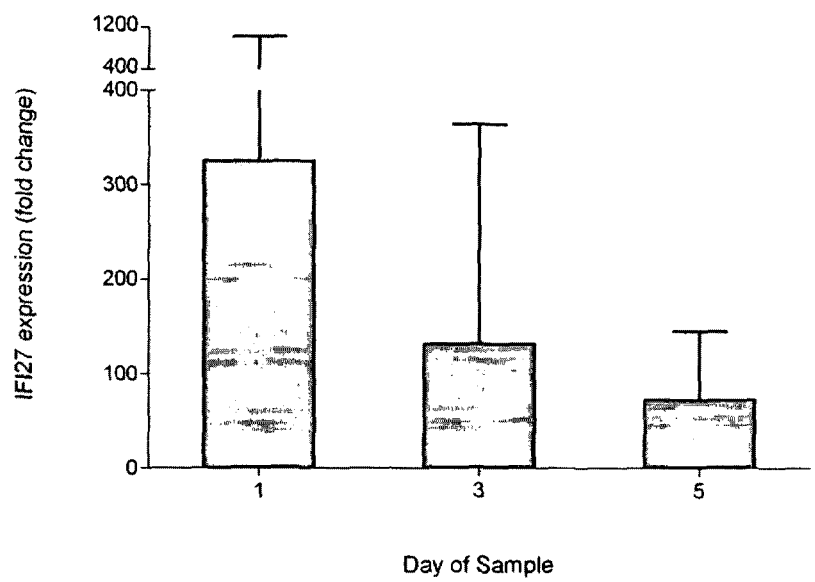
FIG. 4 shows IFI27 expression during recovery from influenza infection in the development set. Patients with severe disease from influenza infection in the development set (n=8) were followed up for five days and peripheral blood IFI27 expression was measured by quantitative PCR on day one, three and five. Bar chart depicts mean fold change+/−SD.
Figure 5:
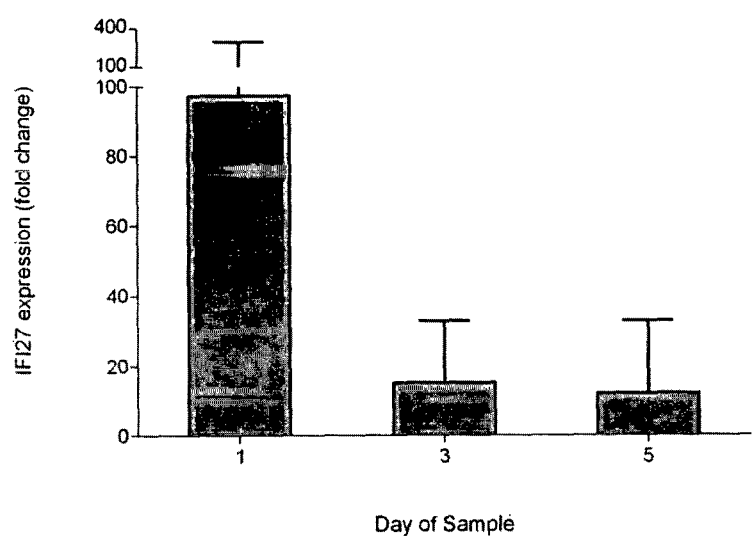
FIG. 5 shows IFI27 expression during recovery from influenza infection in the validation set. Patients with severe disease from influenza infection in the validation set (n=33) were followed up for five days and peripheral blood IFI27 expression was measured by quantitative PCR on day one, three and five. Bar chart depicts mean fold change+/−SD.
Figure 6:
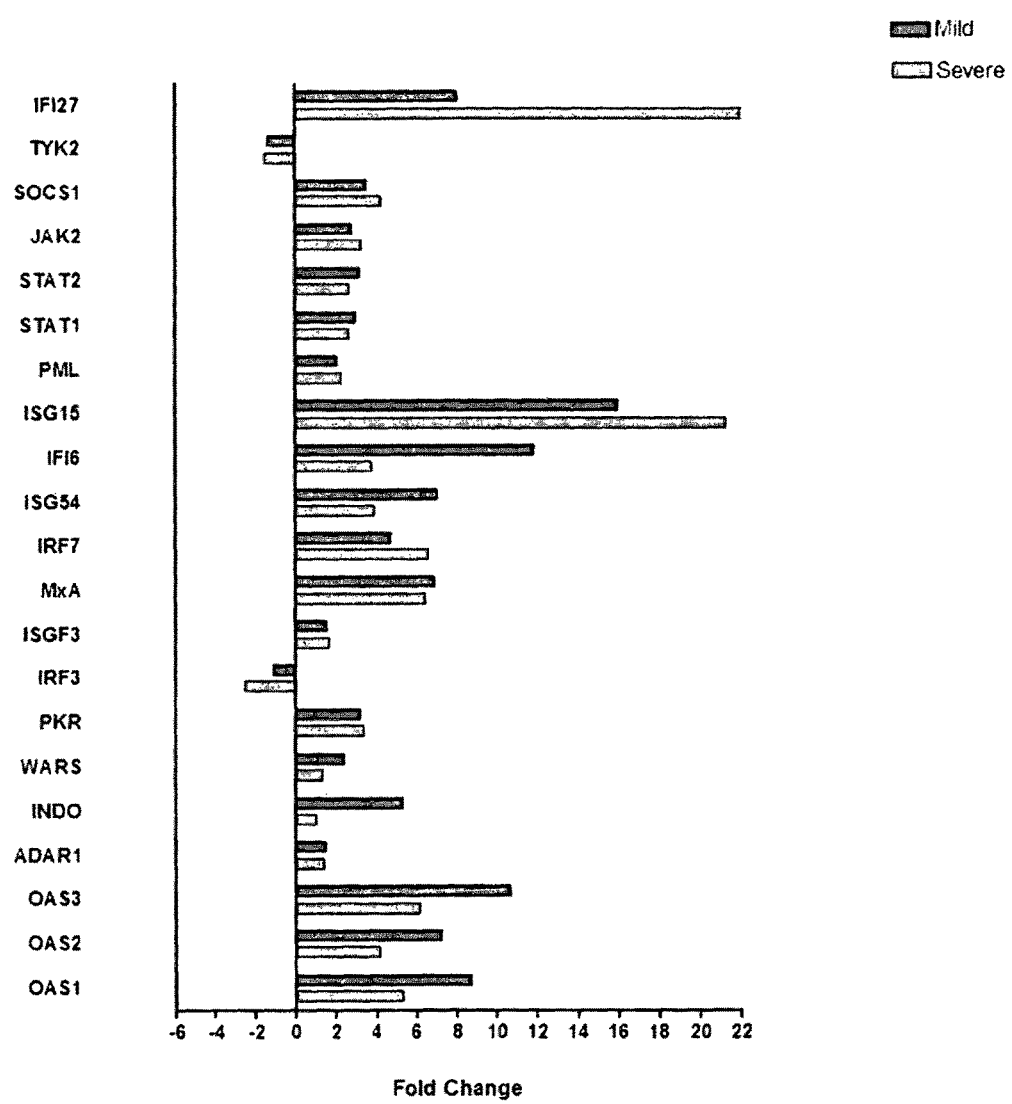
FIG. 6 shows Interferon derived genes in mild and severe disease from influenza infection. Dark coloured bar denotes gene expression in mild disease from influenza infection. Lighter coloured bars denote gene expression in severe disease from influenza infection.

As patients recovered from severe disease, IFI27 expression returned towards baseline levels (FIGS. 4 and 5). As a severity biomarker, IFI27 outperformed all other interferon-derived genes. Compared to other genes, IFI27 showed the greatest differential expression between mild and severe disease caused by influenza infection (FIG. 6).

Figure 7:
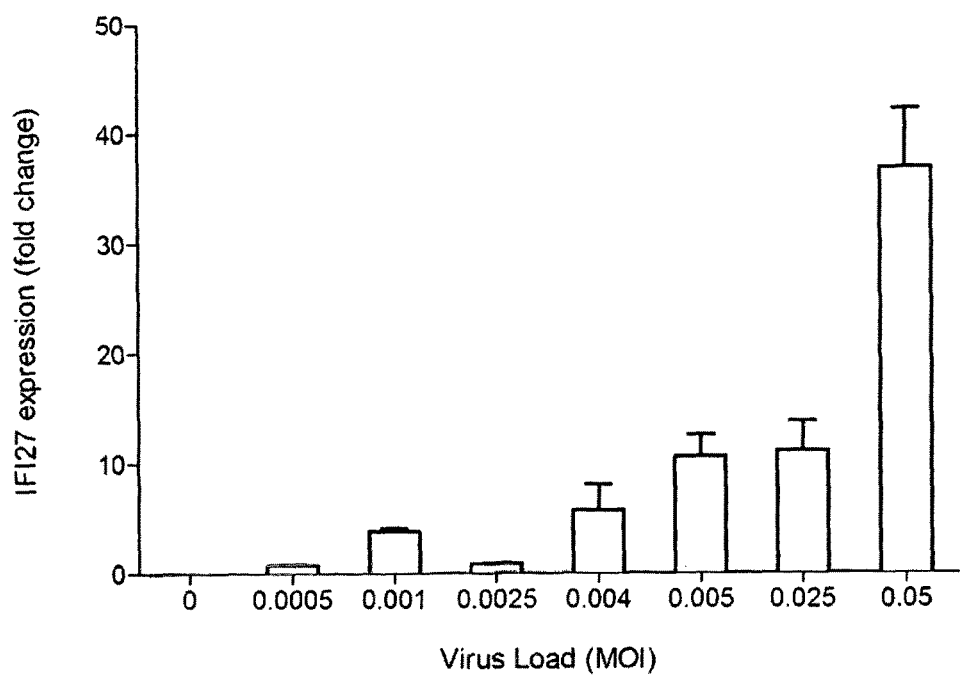
FIG. 7 shows IFI27 expression and increasing viral load. Peripheral blood mononuclear cells isolated from healthy volunteers were cultured with influenza virus (H1N12009). IFI27 expression was measured via quantitative PCR with each concentration of viral load (MOI denotes multiplicity of infection and represents the ratio of virus to total cells). Bar chart depicts mean fold change+/−SD and represents independent experiments' from three different subjects. SEQ ID NO:1
Figure 8:
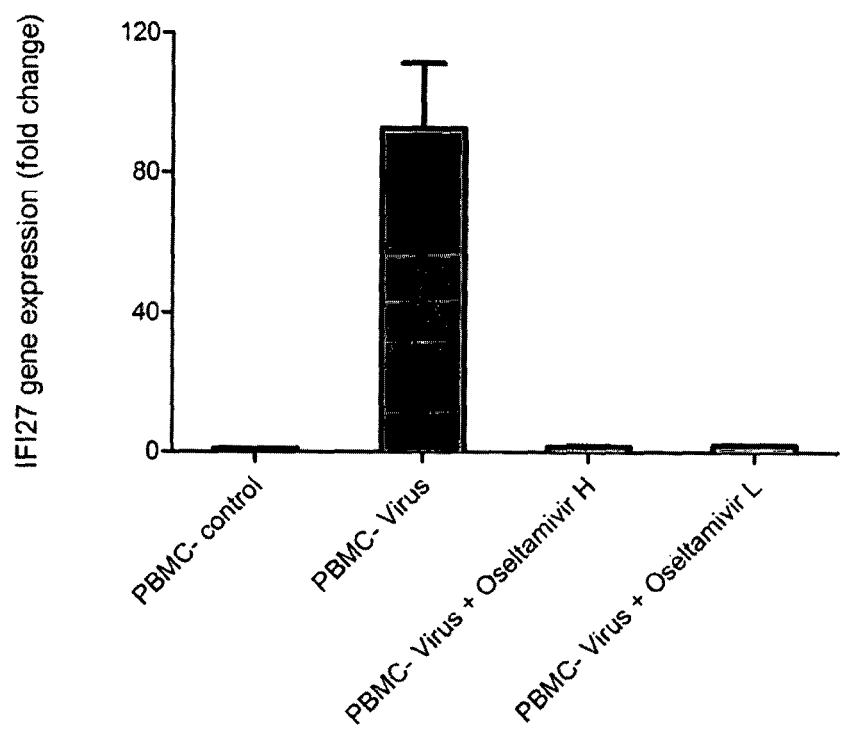
FIG. 8 shows IFI27 expression and antiviral agent. Peripheral blood mononuclear cells (PBMC) isolated from healthy volunteers were cultured with influenza virus (H1N12009) and was then subsequently treated with antiviral agent (oseltamivir). Oseltamivir H denotes high concentration (37 ng/µl). Oseltamivir L denotes low concentration (0.3 ng/µl). IFI27 expression was measured via quantitative PCR. Bar chart depicts mean fold change+/−SD and represents independent experiments from three different subjects.

In vitro experiments confirmed that viral load in peripheral blood correlated with IFI27 expression. Using PBMC isolated from healthy volunteers, it was found that influenza virus caused a dose-dependent increase in IF 127 gene expression (FIG. 7). The upregulation was abolished after the cells were treated with the anti-viral agent oseltamivir phosphate (FIG. 8).

Example 3: Mechanism of IFI27 Expression

Figure 9:
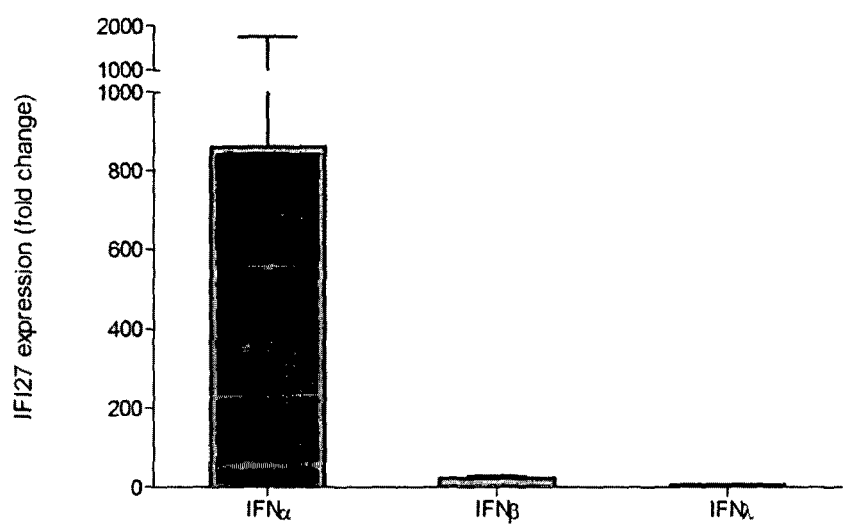
FIG. 9 shows IFI27 expression and activators of interferon pathway. IFI27 expression was measured by PCR after stimulation of peripheral blood mononuclear cells by IFN-alpha, IFN-beta, and IFN-lambda. Bar chart depicts mean fold change+/−SD.
Figure 10:
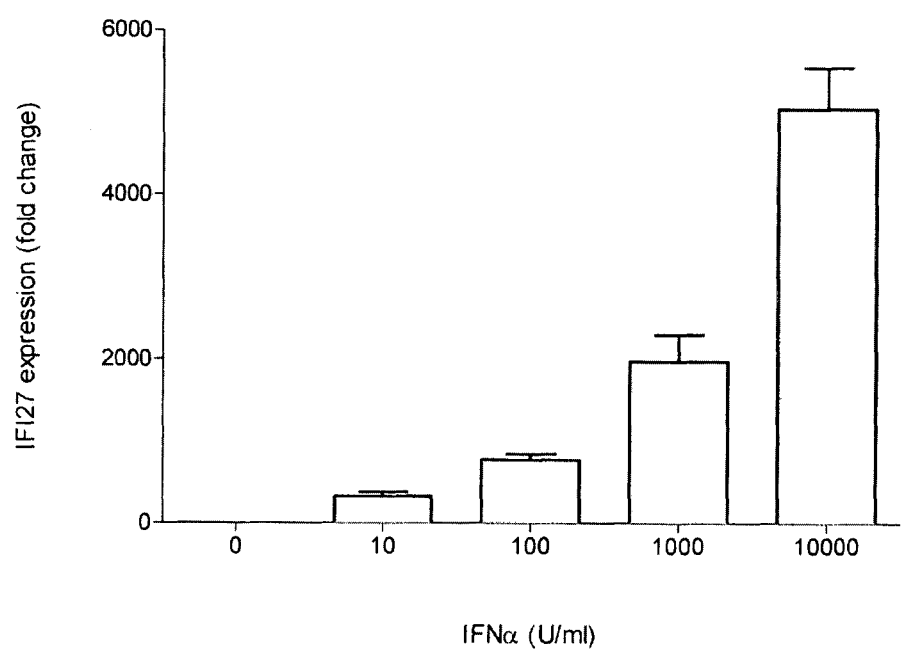
FIG. 10 shows IFI27 expression and interferon alpha. Peripheral blood mononuclear cells isolated from healthy volunteers were cultured with interferon-alpha (IFNα) at different concentrations. IFI27 expression was measured via quantitative PCR. Bar chart depicts mean fold change+/−SD and represents independent experiments from three different subjects.
Figure 11:
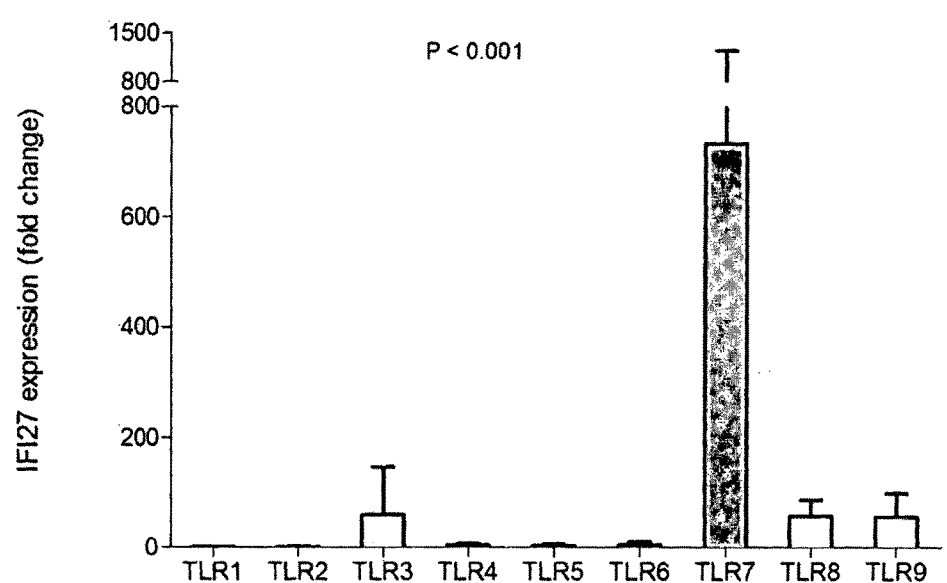
FIG. 11 shows IFI27 expression and toll-like receptor ligands. Peripheral blood mononuclear cells isolated from healthy volunteers were cultured with ligands against toll-like receptors. IFI27 expression was measured via quantitative PCR with each ligand. Independent experiments from different subjects were performed for each toll-like receptor (TLR) ligand including; TLR1, TLR2, TLR3, TLR5, TLR6, TLR8, TLR9 (n=2), TLR4 (n=4), TLR7 (n=10). Bar chart depicts mean fold change+/−SD. p value was calculated using Kruskal-Wallis test for comparison of multiple groups.

To delineate the mechanism of IFI27 expression, experiments were performed to stimulate the interferon pathway in peripheral blood cells using endogenous ligands (interferon-alpha, interferon-beta and interferon-lambda). It was observed that interferon alpha (IFNα) produced the greatest increase in IFI27 expression (FIG. 9) and this increase occurred in a dose-dependent manner (FIG. 10).

Because peripheral blood contains a heterogeneous mix of immune cells, steps were taken to identify the specific immune cell subset that produced the IFI27 signal. Since toll-like receptors (TLR) are the main activators of the IFNα pathway, the effects of applying different TLR ligands to blood cells were evaluated. Amongst all the TLR ligands, it was found that the TLR7 ligand produced the greatest IFI27 expression (FIG. 1). TLR7 is generally found mainly in plasmacytoid dendritic cells (pDCs) and B cells[9], and it was therefore hypothesized that pDCs or B cells were the possible source of IFI27 signal observed in peripheral blood.

Figure 12:
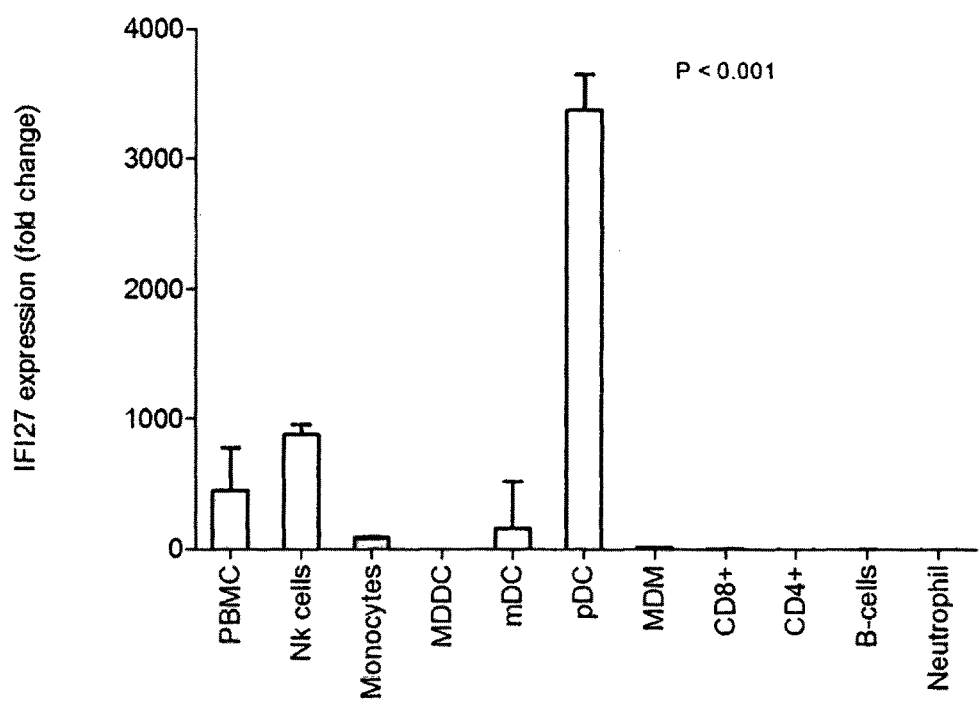
FIG. 12 shows IFI27 expression in different immune cell subset after stimulation by ligand on toll-like receptor 7. After stimulation by Gardiquimod (TLR7 ligand), IFI27 expression was measured via quantitative PCR in each immune cell subsets including CD4, CD8, neutrophils, B cells, monocytes, natural killer cells (NK cells), myeloid dendritic cells (mDC), plasmacytoid dendritic cells (pDC), monocytes derived macrophage (MDM) and monocytes derived dendritic cells (MDDC). PBMC denotes peripheral blood mononuclear cells. Bar chart depicts mean fold change+/−SD. p value was calculated using Kruskal-Wallis test for comparison of multiple groups.
Figure 13:
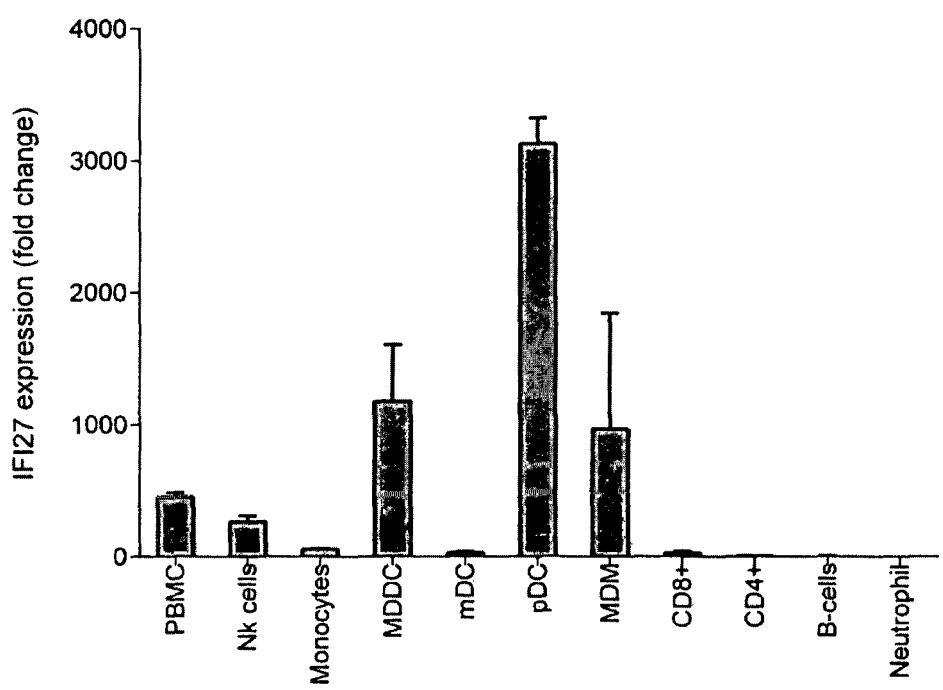
FIG. 13 shows IFI27 expression and viral antigen. IFI27 expression was measured via quantitative PCR with stimulation by viral antigen. Immune cell subsets include CD4, CD8, neutrophils, B cells, monocytes, natural killer cells (NK cells), myeloid dendritic cells (mDC), plasmacytoid dendritic cells (pDC), monocytes derived macrophage (MDM), and monocytes derived dendritic cells (MDDC). PBMC denotes peripheral blood mononuclear cells. Bar chart depicts mean fold change+/−SD.
Figure 14:
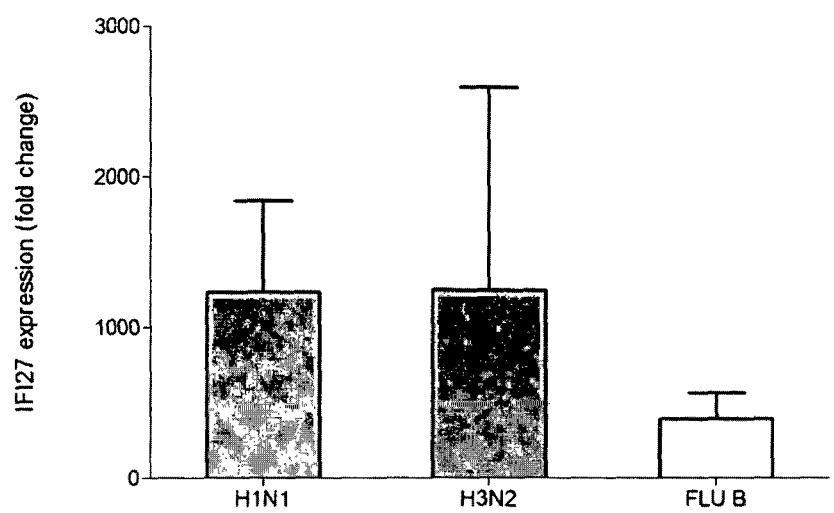
FIG. 14 shows IFI27 expression in plasmacytoid dendritic cells and influenza viruses. Plasmacytoid dendritic cells were cultured with influenza A viruses including H1N1 (California-2009), H3N2 (Victoria-2011), and influenza B virus. IFI27 gene expression was measured by quantitative PCR. Bar chart depicts mean fold change+/−SD. Each data point represents independent experiments from two different subjects.

To test the hypothesis, eight immune cell subsets (CD4, CD8, neutrophils, B cells, monocytes, natural killer cells, myeloid dendritic cells, and plasmacytoid dendritic cells) were purified from the whole blood of healthy volunteers. In addition, in vitro differentiated immune cells subsets from monocytes (monocyte derived macrophages and monocyte derived dendritic cells) were generated. These experiments showed that, compared to all other cell types, pDCs produced the greatest increase in IFI27 gene expression in response to TLR7 ligand (FIG. 12). Other immune cell subsets, including B cells, produced minimal or negligible IFI27 signals. Further experiments using viral antigen confirmed that pDC produced the greatest IFI27 upregulation (FIG. 13). Importantly, using influenza A viruses (H1N1 and H3N2) and influenza B virus, it was found all common seasonal influenza viral strains caused up-regulated IFI27 expression in pDCs (FIG. 14).

Figure 15:
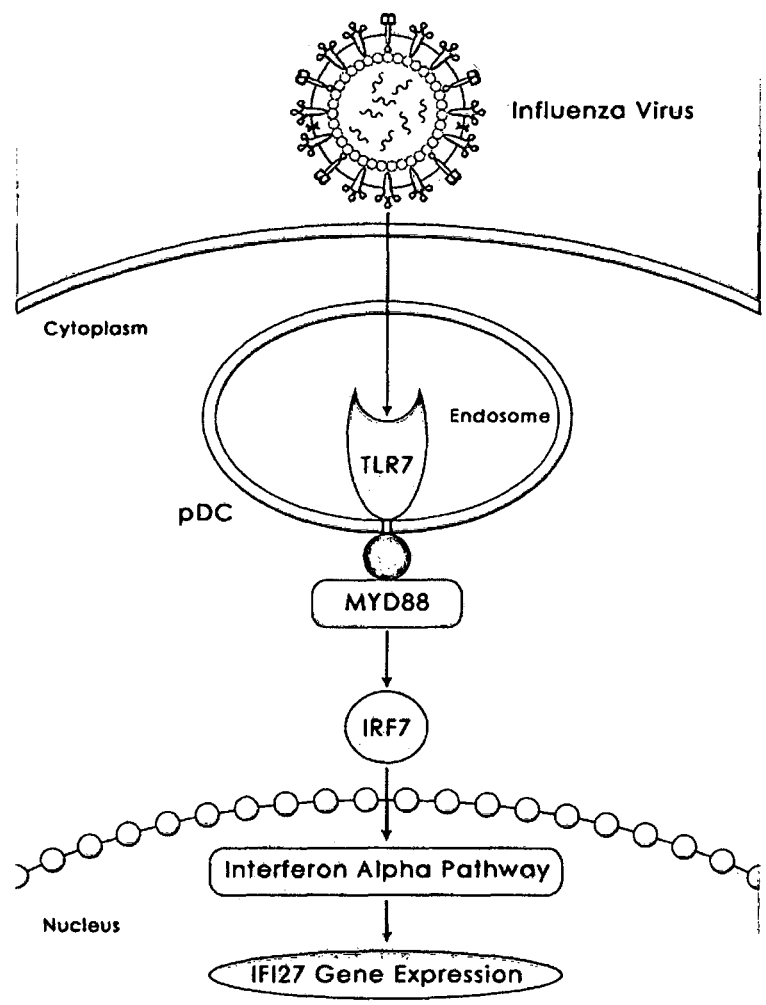
FIG. 15 shows a proposed mechanism for IFI27 gene expression. pDC denotes plasmacytoid dendritic cells. TLR7 denotes toll-like receptor 7. IFNα denotes interferon alpha. MyD88 denotes myeloid differentiation primary response gene. IRF7 denotes interferon regulatory factor 7.

Taken together, the above findings suggested that circulating pDCs gave rise to the IFI27 signals observed in the whole blood of infected patients. This expression can be mediated via TLR7 receptor, a highly specific endogenous receptor for single-stranded RNA virus[10]. Exposure to influenza virus may lead to activation of TLR7, which in turn results in a dose-dependent IFI27 upregulation via the IFNα pathway (production of IFN-a is dependent on the toll-interleukin-1 receptor domain-containing adaptor MyD88 that form a complex with the transcription factor IRF7 (FIG. 15).

Example 4: Time-Course of IFI27 Expression

Figure 16:
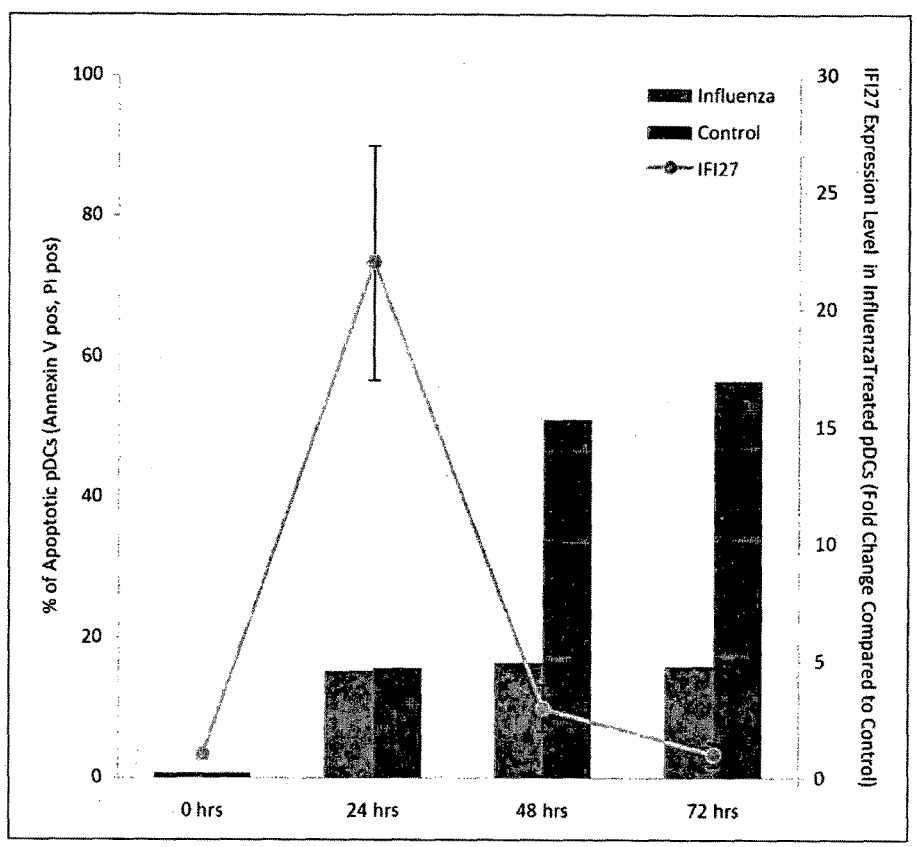
FIG. 16 shows a time-course of IFI27 expression in plasmacytoid dendritic cells (pDCs). Influenza virus was cultured with plasmacytoid dendritic cells. IFI27 gene expression was measured daily by quantitative PCR. Apoptotic cells were identified as both annexin V and propidium iodide positive (Annexin V pos, PI pos), as gated by flow cytometry. Bar chart depicts mean fold change+/−SD.

To investigate the time-course of IFI27 expression, a longitudinal analysis of IFI27 expression in pDCs was performed. pDCs were exposed to influenza virus and the IFI27 gene-expression measured daily over 4 days (FIG. 16). This experiment showed that pDCs rapidly increased IFI27 expression within 24 hours, followed by a decline at 48 and 72 hours. The decline in gene expression was not due to a decrease in the number of pDCs, since the number of surviving cells remains relatively constant at 48 and 72 hours, as demonstrated by apoptosis assay (FIG. 16). This observation demonstrated that IFI27 has fast upregulation occurring in the early phase of infection.

Example 5: IFI27 Expression in Bacterial Infection

Figure 17:
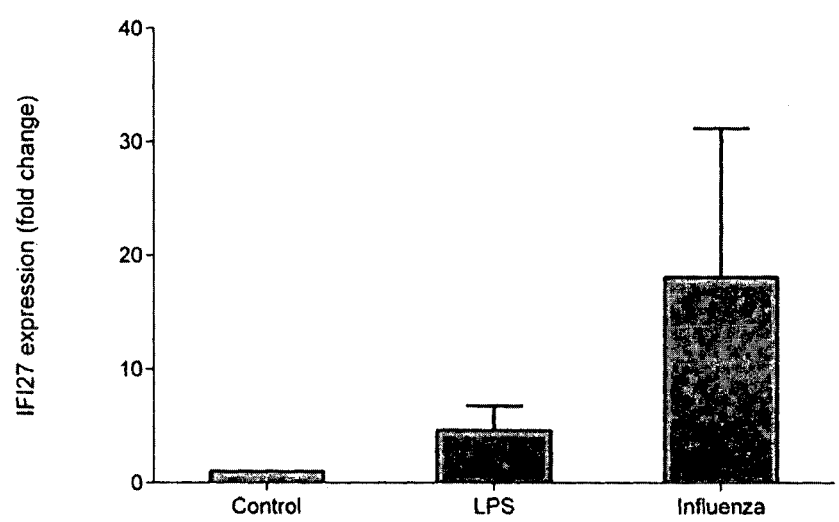
FIG. 17 shows IFI27 expression in response to bacterial and viral pathogens. IFI27 expression was measured via quantitative PCR after stimulation by viral (H1N1 influenza virus) and bacterial stimulation (LPS denotes lipopolysaccharide). Bar chart depicts mean fold change+/−SD.
Figure 18:
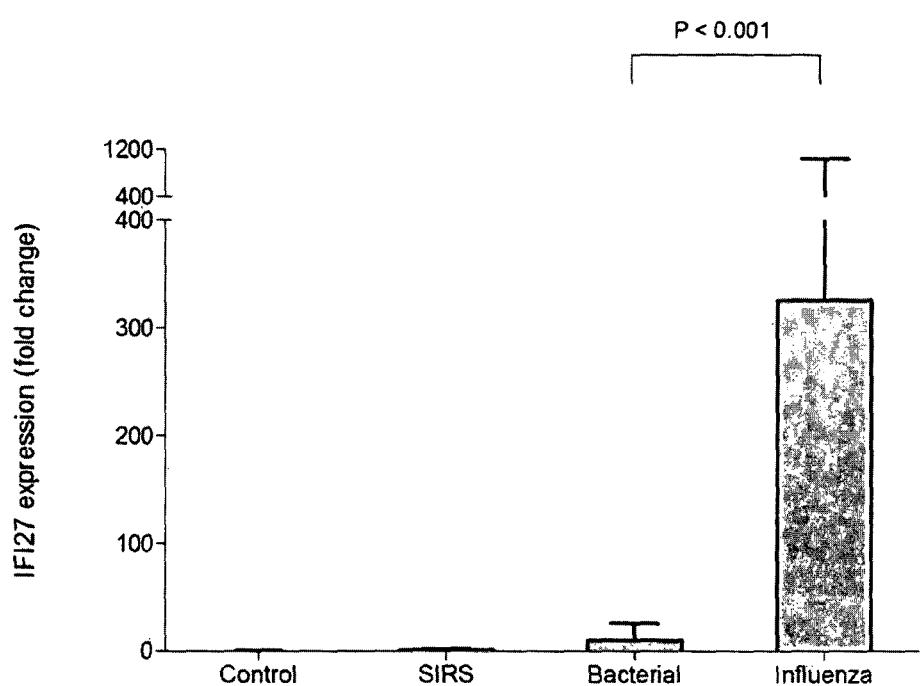
FIG. 18 shows IFI27 gene expression in different disease states. SIRS denotes systemic inflammatory response syndrome. Peripheral blood IFI27 gene expression was measured by quantitative PCR in individuals with influenza pneumonia (n=8), bacterial pneumonia (n=16), SIRS (n=12) and healthy controls (n=18). Bar chart depicts mean fold change+/−SD. p values were calculated using non-parametric Mann-Whitney U test.
Figure 19:
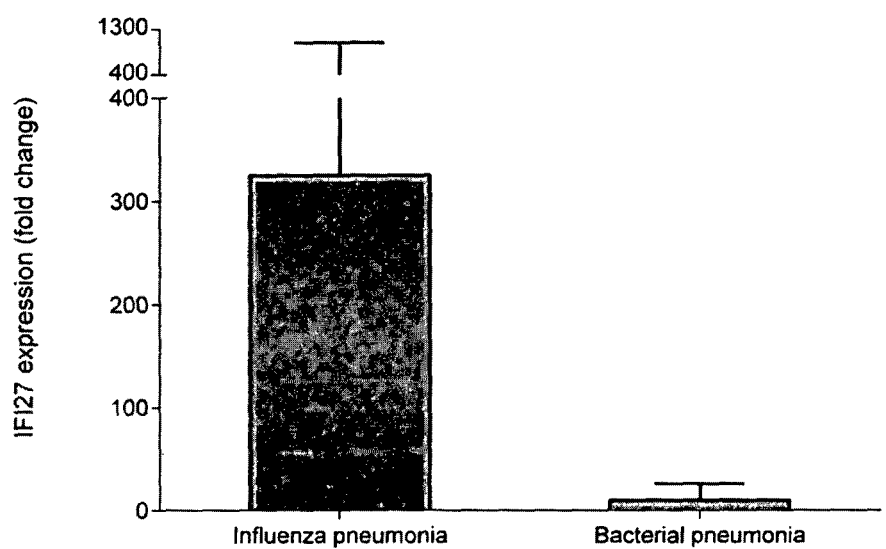
FIG. 19 shows IFI27 expression in bacterial and influenza pneumonia. IFI27 expression was measured via quantitative PCR in two cohorts of patients with severe influenza pneumonia (n=8) and bacterial pneumonia (n=16). Bar chart depicts mean fold change+/−SD.

Whether other pathogens (e.g. bacteria) could also increase IFI27 expression was also investigated. To this end, PBMC were cultured with lipopolysaccharide (LPS). It was found that LPS caused negligible IFI27 gene expression (FIG. 17). This was confirmed in a cohort of patients with bacterial pneumonia where IFI27 expression was significantly less compared to patients with influenza pneumonia (FIG. 18). This was further validated in an independent data set (GSE6269) consisting of both viral and bacterial pneumonia patients (n=37). Again, this analysis showed that IFI27 expression was significantly higher in influenza infection, compared to bacterial pneumonia (FIG. 19).

Example 6: IFI27 Expression in Systemic Inflammation

Figure 20:
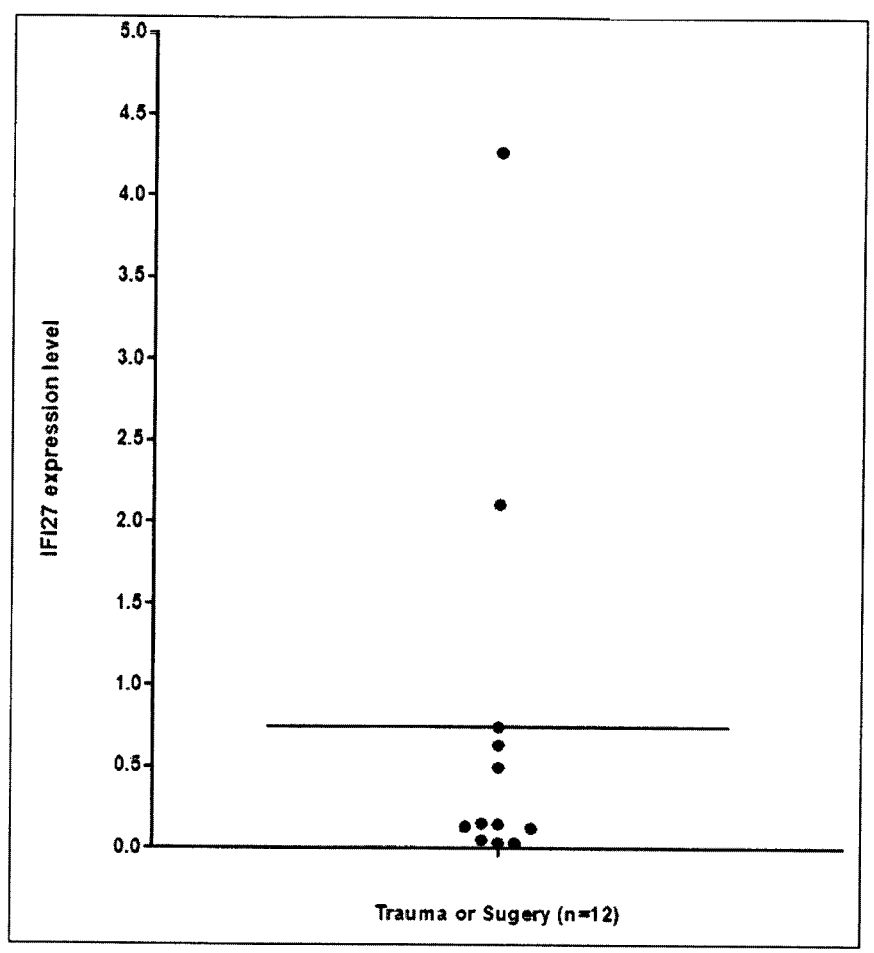
FIG. 20 shows IFI27 expression in trauma and surgery patients.
Figure 21:
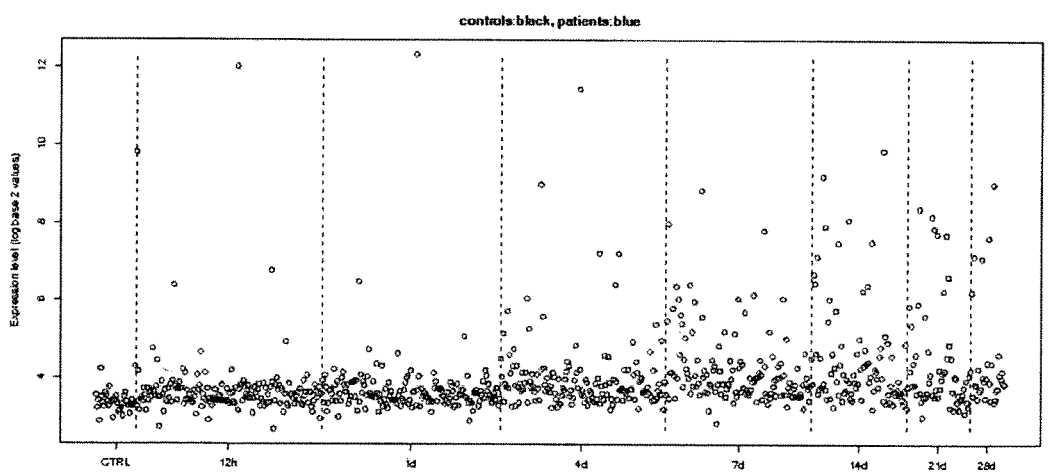
FIG. 21 shows IFI27 expression in a large cohort of trauma patients. Validation of biomarker using an independent cohort of trauma patients (n=167). Gene expression omnibus (GEO) provide microarray data for calculation of IFI27 expression (GSE11375). Gene expression data was recorded over 28 days. Each data point represents gene expression level of an individual patient.

Severe illnesses elicit a generalized systemic inflammatory response in the host, and whether severe illnesses could also increase IFI27 expression was investigated. In a cohort of patients with systemic inflammatory response syndrome (caused by trauma, pancreatitis and high risk surgery), it was found that IFI27 gene-expression was not significantly increased (FIG. 20). This was confirmed in an independent data set (GSE11375) of SIRS patients (n=167), where IFI27 expression was minimal (FIG. 21).

Example 7: Discussion

Influenza pandemics are characterized by a rapid dissemination of a new viral strain through a susceptible population. The exponential rise in infected individuals during an outbreak makes it logistically impossible to test and quarantine every suspected case. The public health response will quickly shift from outbreak containment to allocation of health care resources to the most critically ill. Therefore, the ability to rapidly triage a large number of infected individuals and identify those at high risk of deterioration is critical for pandemic management. To this end, IFI27 has been established as a reliable disease severity biomarker associated with influenza infection.

Data has demonstrated that IFI27 correlates with disease severity in three independent cohorts of severe disease from influenza infection. Further validation in other cohorts has confirmed that IFI27 is specific to influenza infection. Furthermore, it has been found that all common influenza viral strains (H1N1, H3N2, influenza B) results in increased IFI27 expression and significant IFI27 upregulation, which is also associated with hospitalization (>50 fold changes) or respiratory failure (>90 fold changes). Taken together, these findings demonstrate that IFI27 expression is a useful blood signature to identify individuals with progressive disease and has valuable clinical applications.

IFI27 has a favourable kinetic profile as a biomarker. IFI27 upregulation occurs rapidly within 24 hours of exposure to influenza virus. This feature can help clinicians minimize treatment delay in high risk patients. During the 2009 H1N1 influenza pandemic, an average delay of 5-7 days was commonly reported among patients with progressive disease[11-13]. IFI27 could help identify these patients prior to their clinical deterioration. Traditionally, risk stratification during a pandemic outbreak relies on known risk factors (e.g. age, pregnancy, obesity or immunosuppression). However, a disproportionally large number of infected patients during 2009 H1N1 influenza pandemic had no identifiable risk factors[14]. Conventional viral assays can identify causative viral strains. But they provide no information about the host response, the main determinant of disease progression. A host response biomarker such as IFI27 overcomes the above limitation by providing information on both diagnosis and host response. Notably, the present data shows that IFI27 outperforms all other known interferon-derived host response biomarkers (e.g. MxA, OAS) in reflecting disease severity.

A common limitation of host response biomarkers is their lack of specificity. For example, in avian flu (H5N1) infection, a high level of inflammatory cytokines (e.g. TNF-α, IL-6) is a marker of disease severity[15]. However, the same biomarkers are also elevated in many non-viral conditions, including bacterial sepsis, trauma and surgery. This lack of specificity occurs because these biomarkers are produced by a variety of immune cells (e.g. monocytes and lymphocytes). In contrast, IFI27 is more pathogen and cell specific. This specificity is likely due to the TLR7-IFNα pathway, which recognizes only single-stranded RNA (e.g. influenza virus)[10]. Importantly, this pathway is presently only known to exist in pDCs, and is absent in other immune cells, hence providing IFI27 with a superior diagnostic specificity unparalleled in the biomarker literature.

A unique challenge in combating influenza pandemic is the unpredictable change in the genetic make-up of the new viral strain. A host response biomarker such as IFI27 could potentially circumvent this challenge. Our data suggest that IFI27 expression is increased by all common influenza strains including pandemic H1N1, seasonal H3N2, and influenza B.

The IFI27 gene encodes a protein (ISG12) located in the inner mitochondria membrane of the cell[8]. Measuring cellular or serum IFI27 protein may provide an alternative diagnostic approach to detecting influenza infection. A geneexpression assay, on the other hand, provides a more rapid and cost-effective means to measure IFI27 expression. By obtaining 2.5 ml of peripheral blood sample, IFI27 expression level can be quickly assayed by conventional RT-PCR within hours, making it feasible to monitor activated pDCs in routine clinical practice.

The present invention has important therapeutic and clinical implications. Recent advances in immunology show that dendritic cells are at the centre stage of host response, with several dendritic cell subsets, including pDCs, coordinating multiple arms of the immune response against viral infection[17,18]. This complex dendritic cell network is essential for host defence; however, it could also be a source of immunopathology[19]. Emerging evidence shows that an abnormal pDC response can support viral propagation and is associated with lethal influenza infection[20-22]. To combat severe disease from viral infection, drugs targeting dendritic cells have recently been developed[23-24]. However, there is no currently available assay to identify which patients are suitable for pDC-directed therapy. However, herein is provided the first data that links a new biomarker with pDC response and clinical severity. Applied as a companion diagnostic, IFI27 expression may also help identify a subgroup of patients who could benefit from pDC-directed therapy.

REFERENCES

1. Campbell A, et al. Risk of severe outcomes among patients admitted to hospital with pandemic (H1N1) influenza. CMAJ. 2010; 182(4): 349-55.

2. Bermejo-Martin J, Lejarazu R, Pumarola T, Rello J, Almansa R, Ramirez P. Martin-Loeches I: Th1 and Th17 hypercytokinemia as early host response signature in severe pandemic influenza. Crit Care 2009; 13:R201.
3. Rasmussen U B, Wolf C & Mattei M-G et al. Identification of a new interferon a-inducible gene (p27) on human chromosome 14q32 and its expression in breast carcinoma. Cancer Res. 1993; 53: 4096-4101.
4. Bowcock A M, Shannon W & Du F et al. Insights into psoriasis and other inflammatory diseases from large-scale gene expression studies. Hum Mol Genet. 2001; 10: 1793-1805.
5. Suomela S, Li Cao L, Bowcock A. & Saarialho-Kere U. Interferon α-Inducible Protein 27 (IFI27) is Upregulated in Psoriatic Skin and Certain Epithelial Cancers. J. Invest. Dermatol. 2004; 122, 717-721.
6. Nzeusseu Toukap A, Galant C. Theate I, Maudoux A L, Lories R J, Houssiau F A, Lauwerys B R. Identification of distinct gene expression profiles in the synovium of patients with systemic lupus erythematosus. Arthritis Rheum. 2007; 56(5):1579-88.
7. Smidt, K C, et al., Biochim Biophys Acta. 2003; Jul. 30; 1638(3):227-34
8. Gjermandsen I M, Justesen J & Martensen P M. The interferon-induced gene ISG12 is regulated by various cytokines as the gene 6-16 in human cell lines. Cytokine. 2000; 12: 233-238.
9. Hornung V, Rothenfusser S. Britsch S. Krug A, Jahrsdorfer B, Giese T, et al. Quantitative expression of toll-like receptor 1-10 mRNA in cellular subsets of human peripheral blood mononuclear cells and sensitivity to CpG Oligodeoxynucleotides. J Immunol. 2002; 168: 4531-7.
10. Diebold S, Kaisho T, Hemmi H, Akira S, Sousa C. Innate antiviral response by means of TLR7-mediated recognition of single-stranded RNA. Science. 2004; 303: 1529-31.
11. Alonso-Tarres C, Cortes-Lletget C, Pintado S, Ricart A. Severe influenza A (H1N1)v in patients without any known risk factor. Crit Care. 2009; 13: 425.
12. To K, Hung I, Li I, Lee K, Koo C, Yan W, et al. Delayed clearance of viral load and marked cytokine activation in severe cases of pandemic H1N1 2009 influenza virus infection. Clin Infect Dis. 2010: 50: 850-9.
13. Perez-Padilla R, de la Rosa-Zamboni D, Ponce de Leon S, Hernandez M. Quinones-Falconi F, Bautista E, et al. Pneumonia and Respiratory Failure from Swine-Origin Influenza A (H1N1) in Mexico. N Engl J Med. 2009; 361: 680-9.
14. WHO. Clinical aspects of pandemic 2009 influenza A (H1N1) virus infection. N Engl J Med. 2010; 362: 1708-19.
15. WHO. Current concepts: avian influenza (H5N1) infections in humans. N Engl J Med. 2005; 353: 1374-85.
16. Rosebeck S, Leaman D. Mitochondrial localization and pro-apoptotic effects of the interferon-inducible protein ISG12a. Apoptosis. 2008; 13: 562-72.
17. Steinman R. Decisions about dendritic cells: past, present, and future. Annu Rev Immunol. 2012; 30: 1-22.
18. Satpathy A, Wu X, Albring J, Murphy K. Re(de)fining the dendritic cell lineage. Nature Immunology. 2012; 13: 1145-54.
19. Swiecki M, Collado M. Accumulation of plasmacytoid DC: roles in disease pathogenesis and targets for immunotherapy. Eur J Immunol. 2010; 40: 2085-130.
20. Soloff A, Weirback H, Ross T. Barratt-Boyes S. Plasmacytoid dendritic cell depletion leads to an enhanced mononuclear phagocyte response in lungs of mice with lethal influenza virus infection. Comparative Immunology, microbiology and infectious diseases. 2012; 35: 309-17.
21. Langlois R, Legge K. Plasmacytoid dendritic cells enhance mortality during lethal influenza infection by eliminating virus-specific CD8 T cells. J Immunol. 2010; 184: 4440-6.
22. Mecal M, Lewis G, Kunz S, Flavell R, Harker J, Zuniga E. Plasmacytoid dendritic cells are productively infected and activated through TLR-7 early after arenavirus infection. Cell Host & Microbes. 2012; 11: 617-30.
23. Guiduci C, Coffman R, Barrat F. Signalling pathways leading to IFN-a production in human plasmacytoid dendritic cell and the possible use of agonists or antagonists of TLR7 and TLR9 in clinical indications. J Intern Med. 2008; 265: 43-57.
24. Aldridge J, Moseley C, Boltz D, Negovetich N, Reynolds C, Franks J, et al. TNF/iNOS-producing dendritic cells are the necessary evil of lethal influenza virus infection. PNAS. 2009; 106: 5306-11.

The invention claimed is:

1. A method for determining a treatment course of action of influenza or viral pneumonia in a patient, the method comprising
   a) determining an expression level of interferon alpha inducible protein 27 (IFI27) gene product in a blood or plasmacytoid dendritic cell sample from said patient and comparing the determined level of IFI27 gene product to a standard level, wherein said standard level is selected from the group consisting of the level of IFI27 gene product in a healthy subject, the level of IFI27 gene product in a subject with influenza that is asymptomatic, and the level of IFI27 gene product in a subject infected with influenza virus who does not develop severe disease;
   b) identifying a patient with a level of IFI27 gene product of at least 40 to 60 times higher than said standard level; and
   c) admitting said patient with a level of IFI27 gene product of at least 40 to 60 times higher than said standard level to the hospital for treatment and not admitting a patient with a level of IFI27 gene product of less than 40 to 60 times than said standard level to the hospital.

2. The method of claim 1, wherein said treatment is an anti-viral agent.

3. The method of claim 1, wherein the standard level is prepared at the same time as determining the expression level of IFI27 gene product in the blood or plasmacytoid dendritic cell sample from said patient.

4. The method of claim 1, further comprising repeating steps a) and b) on a second blood or plasmacytoid dendritic cell sample obtained from the patient at a different time from said blood or plasmacytoid dendritic cell sample.

5. The method of claim 4, further comprising the step of identifying a patient with an increase or decrease of the expression level of IFI27 gene product in said second blood or plasmacytoid dendritic cell sample.

6. The method of claim 1, wherein the determining comprises contacting the blood or plasmacytoid dendritic cell sample with an agent capable of binding to an IFI27 gene product and detecting binding between the agent and the IFI27 gene product.

7. The method of claim 1, wherein the IFI27 gene product comprises the nucleic acid sequence of SEQ ID NO:1 or SEQ ID NO:2.

8. The method of claim 1, wherein the IFI27 gene product comprises the amino acid sequence of SEQ ID NO:3 or SEQ ID NO:4.

9. The method of claim 1, wherein said determining comprises polymerase chain reaction that utilizes one or more primers capable of amplifying at least a portion of a nucleic acid sequence selected from the sequences of (i) SEQ ID NO:1, (ii) SEQ ID NO:2, (iii) SEQ ID NO:5, and (iv) SEQ ID NO:6.

10. The method of claim 1, wherein said determining comprises a polymerase chain reaction utilizing one or both of the primer sequences of SEQ ID NO:7 (acctcatcagcagt-gaccagt) and SEQ ID NO:8 (acatcatcttggctgctatgg) or SEQ ID NO:9 (TGCCTCGGGCAGCCT) and SEQ ID NO:10 (TTGGTCAATCCGGAGAGTCC).

11. The method of claim 1 wherein the method comprises contacting the sample with one or more probe(s) capable of specifically binding to an IFI27 gene product, wherein the one or more probe(s) is a nucleic acid comprising a sequence complementary to at least a portion of the sequence shown in SEQ ID NO:1, a sequence complementary to at least a portion of the sequence shown in SEQ ID NO:2, a nucleic acid comprising a sequence complementary to at least a portion of the sequence shown in SEQ ID NO:5 or a sequence complementary to at least a portion of the sequence shown in SEQ ID NO:6.

* * * * *

SEQUENCE LISTING

```
<160> NUMBER OF SEQ ID NOS: 18

<210> SEQ ID NO 1
<211> LENGTH: 665
<212> TYPE: DNA
<213> ORGANISM: Homo sapiens

<400> SEQUENCE: 1
gggaacacat ccaagcttaa gacggtgagg tcagcttcac attctcagga actctccttc      60
tttgggtctg gctgaagttg aggatctctt actctctagg ccacggaatt aacccgagca     120
ggcatggagg cctctgctct caccctcatca gcagtgacca gtgtggccaa agtggtcagg    180
gtggcctctg gctctgccgt agttttgccc ctggccagga ttgctacagt tgtgattgga    240
ggagttgtgg ccatggcggc tgtgcccatg gtgctcagtg ccatgggctt cactgcggcg    300
ggaatcgcct cgtcctccat agcagccaag atgatgtccg cggcgccat tgccaatggg     360 ggtggagttg cctcgggcag ccttgtggct actctgcagt cactgggagc aactggactc    420
```

```
tccggattga ccaagttcat cctgggctcc attgggtctg ccattgcggc tgtcattgcg      480
aggttctact agctccctgc ccctcgccct gcagagaaga gaaccatgcc aggggagaag      540
gcacccagcc atcctgaccc agcgaggagc caactatccc aaatatacct ggggtgaaat      600
ataccaaatt ctgcatctcc agaggaaaat aagaaataaa gatgaattgt tgcaactctt      660
caaaa                                                                 665

<210> SEQ ID NO 2
<211> LENGTH: 656
<212> TYPE: DNA
<213> ORGANISM: Homo sapiens

<400> SEQUENCE: 2
gggaacacat ccaagcttaa gacggtgagg tcagcttcac attctcagga actctccttc       60
tttgggtctg gctgaagttg aggatctctt actctctagg ccacggaatt aacccgagca      120
ggcatggagg cctctgctct cacctcatca gcagtgacca gtgtggccaa agtggtcagg      180
gtggcctctg gctctgccgt agttttgccc ctggccagga ttgctacagt tgtgattgga      240
ggagttgtgg ctgtgcccat ggtgctcagt gccatgggct tcactgcggc gggaatcgcc      300
tcgtcctcca tagcagccaa gatgatgtcc gcggcggcca ttgccaatgg gggtggagtt      360
gcctcgggca gccttgtggc tactctgcag tcactgggag caactggact ctccggattg      420
accaagttca tcctgggctc cattgggtct gccattgcgg ctgtcattgc gaggttctac      480
tagctccctg ccctcgccct gcagagaag agaaccatgc caggggagaa ggcacccagc       540
catcctgacc cagcgaggag ccaactatcc caaatatacc tggggtgaaa taccaaat       600 tctgcatctc cagaggaaaa taagaaataa agatgaattg ttgcaactct tcaaaa         656

<210> SEQ ID NO 3
<211> LENGTH: 122
<212> TYPE: PRT
<213> ORGANISM: Homo sapiens

<400> SEQUENCE: 3

Met Glu Ala Ser Ala Leu Thr Ser Ser Ala Val Thr Ser Val Ala Lys
1               5                   10                  15

Val Val Arg Val Ala Ser Gly Ser Ala Val Val Leu Pro Leu Ala Arg
            20                  25                  30

Ile Ala Thr Val Val Ile Gly Gly Val Val Ala Met Ala Ala Val Pro
        35                  40                  45

Met Val Leu Ser Ala Met Gly Phe Thr Ala Ala Gly Ile Ala Ser Ser
    50                  55                  60

Ser Ile Ala Ala Lys Met Met Ser Ala Ala Ile Ala Asn Gly Gly
65                  70                  75                  80

Gly Val Ala Ser Gly Ser Leu Val Ala Thr Leu Gln Ser Leu Gly Ala
                85                  90                  95

Thr Gly Leu Ser Gly Leu Thr Lys Phe Ile Leu Gly Ser Ile Gly Ser
            100                 105                 110

Ala Ile Ala Ala Val Ile Ala Arg Phe Tyr
        115                 120

<210> SEQ ID NO 4
<211> LENGTH: 119
<212> TYPE: PRT
<213> ORGANISM: Homo sapiens

<400> SEQUENCE: 4
```

```
Met Glu Ala Ser Ala Leu Thr Ser Ser Ala Val Thr Ser Val Ala Lys
1               5                   10                  15

Val Val Arg Val Ala Ser Gly Ser Ala Val Val Leu Pro Leu Ala Arg
            20                  25                  30

Ile Ala Thr Val Val Ile Gly Gly Val Val Ala Val Pro Met Val Leu
            35                  40                  45

Ser Ala Met Gly Phe Thr Ala Ala Gly Ile Ala Ser Ser Ser Ile Ala
        50                  55                  60

Ala Lys Met Met Ser Ala Ala Ile Ala Asn Gly Gly Gly Val Ala
65              70                  75                  80

Ser Gly Ser Leu Val Ala Thr Leu Gln Ser Leu Gly Ala Thr Gly Leu
                85                  90                  95

Ser Gly Leu Thr Lys Phe Ile Leu Gly Ser Ile Gly Ser Ala Ile Ala
            100                 105                 110

Ala Val Ile Ala Arg Phe Tyr
            115
```

<210> SEQ ID NO 5
<211> LENGTH: 665
<212> TYPE: DNA
<213> ORGANISM: Artificial Sequence
<220> FEATURE:
<223> OTHER INFORMATION: Synthesised polynucleotide

<400> SEQUENCE: 5

| | | |
|---|---|---|
| ttttgaagag ttgcaacaat tcatctttat ttcttatttt cctctggaga tgcagaattt | 60 |
| ggtatatttc accccaggta tatttgggat agttggctcc tcgctgggtc aggatggctg | 120 |
| ggtgccttct cccctggcat ggttctcttc tctgcagggc gaggggcagg gagctagtag | 180 |
| aacctcgcaa tgacagccgc aatggcagac ccaatggagc ccaggatgaa cttggtcaat | 240 |
| ccggagagtc cagttgctcc cagtgactgc agagtagcca caaggctgcc cgaggcaact | 300 |
| ccacccccat tggcaatggc cgccgcggac atcatcttgg ctgctatgga ggacgaggcg | 360 |
| attcccgccg cagtgaagcc catggcactg agcaccatgg gcacagccgc catggccaca | 420 |
| actcctccaa tcacaactgt agcaatcctg gccaggggca aaactacggc agagccagag | 480 |
| gccaccctga ccactttggc cacactggtc actgctgatg aggtgagagc agaggcctcc | 540 |
| atgcctgctc gggttaattc cgtggcctag agagtaagag atcctcaact tcagccagac | 600 |
| ccaaagaagg agagttcctg agaatgtgaa gctgacctca ccgtcttaag cttggatgtg | 660 |
| ttccc | 665 |

<210> SEQ ID NO 6
<211> LENGTH: 656
<212> TYPE: DNA
<213> ORGANISM: Artificial Sequence
<220> FEATURE:
<223> OTHER INFORMATION: Synthesised polynucleotide

<400> SEQUENCE: 6

| | | |
|---|---|---|
| ttttgaagag ttgcaacaat tcatctttat ttcttatttt cctctggaga tgcagaattt | 60 |
| ggtatatttc accccaggta tatttgggat agttggctcc tcgctgggtc aggatggctg | 120 |
| ggtgccttct cccctggcat ggttctcttc tctgcagggc gaggggcagg gagctagtag | 180 |
| aacctcgcaa tgacagccgc aatggcagac ccaatggagc ccaggatgaa cttggtcaat | 240 |
| ccggagagtc cagttgctcc cagtgactgc agagtagcca caaggctgcc cgaggcaact | 300 |

```
ccaccccat  tggcaatggc  cgccgcggac  atcatcttgg  ctgctatgga  ggacgaggcg      360
attcccgccg  cagtgaagcc  catggcactg  agcaccatgg  gcacagccac  aactcctcca      420
atcacaactg  tagcaatcct  ggccagggc   aaaactacgg  cagagccaga  ggccaccctg      480
accactttgg  ccacactggt  cactgctgat  gaggtgagag  cagaggcctc  catgcctgct      540
cgggttaatt  ccgtggccta  gagagtaaga  gatcctcaac  ttcagccaga  cccaaagaag      600
gagagttcct  gagaatgtga  agctgacctc  accgtcttaa  gcttggatgt  gttccc          656

<210> SEQ ID NO 7
<211> LENGTH: 21
<212> TYPE: DNA
<213> ORGANISM: Artificial Sequence
<220> FEATURE:
<223> OTHER INFORMATION: Synthesised polynucleotide

<400> SEQUENCE: 7
acctcatcag cagtgaccag t                                                      21

<210> SEQ ID NO 8
<211> LENGTH: 21
<212> TYPE: DNA
<213> ORGANISM: Artificial Sequence
<220> FEATURE:
<223> OTHER INFORMATION: Synthesised polynucleotide

<400> SEQUENCE: 8
acatcatctt ggctgctatg g                                                      21

<210> SEQ ID NO 9
<211> LENGTH: 15
<212> TYPE: DNA
<213> ORGANISM: Artificial Sequence
<220> FEATURE:
<223> OTHER INFORMATION: Synthesised polynucleotide

<400> SEQUENCE: 9
tgcctcgggc agcct                                                             15

<210> SEQ ID NO 10
<211> LENGTH: 20
<212> TYPE: DNA
<213> ORGANISM: Artificial Sequence
<220> FEATURE:
<223> OTHER INFORMATION: Synthesised polynucleotide

<400> SEQUENCE: 10
ttggtcaatc cggagagtcc                                                        20

<210> SEQ ID NO 11
<211> LENGTH: 187
<212> TYPE: DNA
<213> ORGANISM: Homo sapiens

<400> SEQUENCE: 11
acctcatcag  cagtgaccag  tgtggccaaa  gtggtcaggg  tggcctctgg  ctctgccgta       60
gttttgcccc  tggccaggat  tgctacagtt  gtgattggag  gagttgtggc  tgtgcccatg      120
gtgctcagtg  ccatgggctt  cactgcggcg  ggaatcgcct  cgtcctccat  agcagccaag      180
atgatgt                                                                    187

<210> SEQ ID NO 12
<211> LENGTH: 1401
```

<212> TYPE: DNA
<213> ORGANISM: Homo sapiens

<400> SEQUENCE: 12

```
ggctgggact ggctgagcct ggcgggaggc ggggtccgag tcaccgcctg ccgccgcgcc      60
cccggtttct ataaattgag cccgcagcct cccgcttcgc tctctgctcc tcctgttcga     120
cagtcagccg catcttcttt tgcgtcgcca gccgagccac atcgctcaga caccatgggg    180
aaggtgaagg tcggagtcaa cggatttggt cgtattgggc gcctggtcac cagggctgct     240
tttaactctg gtaaagtgga tattgttgcc atcaatgacc ccttcattga cctcaactac     300
atggtttaca tgttccaata tgattccacc catggcaaat ccatggcac cgtcaaggct      360
gagaacggga agcttgtcat caatggaaat cccatcacca tcttccagga gcgagatccc     420
tccaaaatca gtggggcga tgctggcgct gagtacgtcg tggagtccac tggcgtcttc     480
accaccatgg agaaggctgg ggctcatttg caggggggag ccaaaagggt catcatctct     540
gccccctctg ctgatgcccc catgttcgtc atgggtgtga accatgagaa gtatgacaac     600
agcctcaaga tcatcagcaa tgcctcctgc accaccaact gcttagcacc cctggccaag     660
gtcatccatg acaactttgg tatcgtggaa ggactcatga ccacagtcca tgccatcact     720
gccacccaga agactgtgga tggcccctcc gggaaactgt ggcgtgatgg ccgcggggct     780
ctccagaaca tcatccctgc ctctactggc gctgccaagg ctgtgggcaa ggtcatccct    840
gagctgaacg ggaagctcac tggcatggcc ttccgtgtcc ccactgccaa cgtgtcagtg     900
gtggacctga cctgccgtct agaaaaacct gccaaatatg atgacatcaa gaaggtggtg     960
aagcaggcgt cggagggccc cctcaagggc atcctgggct acactgagca ccaggtggtc     1020
tcctctgact tcaacagcga cacccactcc tccacctttg acgctggggc tggcattgcc     1080
ctcaacgacc actttgtcaa gctcatttcc tggtatgaca acgaatttgg ctacagcaac     1140
agggtggtgg acctcatggc ccacatggcc tccaaggagt aagaccctg gaccaccagc      1200
cccagcaaga gcacaagagg aagagagaga ccctcactgc tggggagtcc ctgccacact     1260
cagtccccca ccacactgaa tctccctc tcacagttgc catgtagacc ccttgaagag     1320
gggagggggcc tagggagccg caccttgtca tgtaccatca ataaagtacc ctgtgctcaa     1380
ccaaaaaaaa aaaaaaaaaa a                                                1401
```

<210> SEQ ID NO 13
<211> LENGTH: 450
<212> TYPE: DNA
<213> ORGANISM: Homo sapiens

<400> SEQUENCE: 13

```
tagatttggt cgtattgggc gcctggtcac cagggctgct tttaactctg gtaaagtgga      60
tattgttgcc atcaatgacc ccttcattga cctcaactac atggtgagtg ctacatggtg     120
agccccaaag ctggtgtggg aggagccacc tggctgatgg gcagccctt catacctca      180
cgtattcccc caggtttaca tgttccaata tgattccacc catggcaaat ccatggcac      240
cgtcaaggct gagaacggga agcttgtcat caatggaaat cccatcacca tcttccagga    300
gtgagtggaa gacagaatgg aagaaatgtg ctttggggag gcaactagga tggtgtggct     360
cccttgggta tatggtaacc ttgtgtccct caatatggtc ctgtccccat ctccccccca     420
ccccatagg cgagatccct ccaaaatcaa                                         450
```

<210> SEQ ID NO 14

```
<211> LENGTH: 20
<212> TYPE: DNA
<213> ORGANISM: Artificial Sequence
<220> FEATURE:
<223> OTHER INFORMATION: Synthesised polynucleotide

<400> SEQUENCE: 14
acgcatttgg tcgtattggg                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthesised polynucleotide

<400> SEQUENCE: 15
tgattttgga gggatctcgc                                                  20

<210> SEQ ID NO 16
<211> LENGTH: 30
<212> TYPE: DNA
<213> ORGANISM: Artificial Sequence
<220> FEATURE:
<223> OTHER INFORMATION: Synthesised polynucleotide

<400> SEQUENCE: 16
caggaattca tatggaggcc tctgctctca                                       30

<210> SEQ ID NO 17
<211> LENGTH: 30
<212> TYPE: DNA
<213> ORGANISM: Artificial Sequence
<220> FEATURE:
<223> OTHER INFORMATION: Synthesised polynucleotide

<400> SEQUENCE: 17
cgcgaattca gctagtagaa cctcgcaatg                                       30

<210> SEQ ID NO 18
<211> LENGTH: 1425
<212> TYPE: DNA
<213> ORGANISM: Homo sapiens

<400> SEQUENCE: 18
gtgcgcagcg ggtgcatccc tgtccggatg ctgcgcctgc ggtagagcgg ccgccatgtt      60
gcaaccggga aggaaatgaa tgggcagccg ttaggaaagc ctgccggtga ctaaccctgc     120
gctcctgcct cgatgggtgg agtcgcgtgt ggcggggaag tcaggtggag cgaggctagc     180
tggcccgatt tctcctccgg gtgatgcttt tcctagatta ttctctgatt tggtcgtatt     240
gggcgcctgg tcaccagggc tgcttttaac tctggtaaag tggatattgt tgccatcaat     300 gacccccttca ttgacctcaa ctacatggtt tacatgttcc aatatgattc cacccatggc     360
aaattccatg gcaccgtcaa ggctgagaac gggaagcttg tcatcaatgg aaatcccatc     420
accatcttcc aggagcgaga tcctccaaa atcaagtggg gcgatgctgg cgctgagtac     480
gtcgtggagt ccactggcgt cttcaccacc atggagaagg ctggggctca tttgcagggg     540
ggagccaaaa gggtcatcat ctctgccccc tctgctgatg ccccatgtt cgtcatgggt     600 gtgaaccatg agaagtatga caacagcctc aagatcatca gcaatgcctc ctgcaccacc     660
aactgcttag cacccctggc caaggtcatc catgacaact tggtatcgt ggaaggactc     720 atgaccacag tccatgccat cactgccacc cagaagactg tggatggccc ctccgggaaa     780
```

```
ctgtggcgtg atggccgcgg ggctctccag aacatcatcc ctgcctctac tggcgctgcc    840
aaggctgtgg gcaaggtcat ccctgagctg aacgggaagc tcactggcat ggccttccgt    900
gtccccactg ccaacgtgtc agtggtggac ctgacctgcc gtctagaaaa acctgccaaa    960
tatgatgaca tcaagaaggt ggtgaagcag gcgtcggagg gccccctcaa gggcatcctg   1020
ggctacactg agcaccaggt ggtctcctct gacttcaaca gcgacaccca ctcctccacc   1080
tttgacgctg gggctggcat tgccctcaac gaccactttg tcaagctcat ttcctggtat   1140
gacaacgaat ttggctacag caacagggtg gtggacctca tggcccacat ggcctccaag   1200
gagtaagacc cctggaccac cagccccagc aagagcacaa gaggaagaga gagaccctca   1260
ctgctgggga gtccctgcca cactcagtcc cccaccacac tgaatctccc ctcctcacag   1320
ttgccatgta gaccccttga agaggggagg ggcctaggga gccgcacctt gtcatgtacc   1380
atcaataaag tacctgtgc tcaaccaaaa aaaaaaaaa aaaaa              1425
```